US007465537B2

(12) United States Patent
Raney et al.

(10) Patent No.: US 7,465,537 B2
(45) Date of Patent: Dec. 16, 2008

(54) COMPOUNDS AND METHODS FOR INHIBITING HEPATITIS C VIRUS REPLICATION

(75) Inventors: Kevin D. Raney, Little Rock, AR (US); Craig E. Cameron, State College, PA (US); Bhuvanesh Dave, Little Rock, AR (US); Joshua Sakon, Fayetteville, AR (US); Jeff Zhiqiang Lu, Towson, MD (US); Samuel G. Mackintosh, Little Rock, AR (US); Thomas A. Jennings, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 225 days.

(21) Appl. No.: 11/119,587

(22) Filed: May 1, 2005

(65) Prior Publication Data

US 2006/0246421 A1    Nov. 2, 2006

(51) Int. Cl.
*C12Q 1/68* (2006.01)
*C12N 4/48* (2006.01)
(52) U.S. Cl. .................... 435/5; 424/149.1; 530/350
(58) Field of Classification Search ........................ None
See application file for complete search history.

(56) References Cited

U.S. PATENT DOCUMENTS

| 5,331,573 | A | 7/1994 | Balaji et al. |
| 5,500,807 | A | 3/1996 | Lavin et al. |
| 7,208,309 | B2 * | 4/2007 | Kukolj et al. ............... 435/219 |
| 7,241,796 | B2 * | 7/2007 | Farmer et al. ............... 514/411 |

FOREIGN PATENT DOCUMENTS

WO    WO 01/21189 A1 *    3/2001

OTHER PUBLICATIONS

Lamarre et al. An NS3 protease inhibitor with antivirial effects in humans infected with hepatitis C virus, Nature 2003, vol. 426, p. 186-189, 314.*
Blanchard, E., Brand, D., Trassard, S., Goudeau, A., and Roingeard, P. (2002) Hepatitis C virus-like particle morphogenesis. *J. Virol.* 76, 4073-4079.
Blight, KJ, Kolykhalov AA, Rice CM (2000) Efficient initiation of HCV RNA replication in cell culture. *Science* 290: 1972-1974.
Bohm, H-J (1992) The Computer Program LUDI: A New Method for the De Novo Design of Enzyme Inhibitors. *J. Comp. Aid. Molec. Design* 6: 61-78.
Cho, HS, Ha NC, Kang LW, Chung KM, Back SH, Jang SK, Oh BH (1998) Crystal structure of RNA helicase from genotype 1b hepatitis C virus. A feasible mechanism of unwinding duplex RNA. *J. Biol Chem* 273: 15045-15052.
Cho, Y. G., Yang, S. H., and Sung, Y. C. (1998) In vivo assay for hepatitis C viral serine proteiase activity using a secreted protein. *J. Virol. Methods* 72, 109-115.

Choo, Q. L., Kuo, G., Weiner, A. J., Overby, L. R., Bradley, D. W., and Houghton, M. (1989) Isolation of a cDNA clone derived from a blood-borne non-A, non-B viral hepatitis genome. *Science* 244, 359-362.
Cristiano, R.J. et al. (1993) Hepatic gene therapy: efficient gene delivery and expression in primary hepatocytes utilizing a conjugated adenovirus-DNA complex. *Proc. Nat'l. Acad. Sci.* USA 90, 11548-11552.
Frick, DN, Rypma RS, Lam AM, Gu B (2004) The nonstructural protein 3 protease/helicase requires an intact protease domain to unwind duplex RNA efficiently. *J. Biol Chem* 279: 1269-1280.
Gallinari, P, Brennan D, Nardi C, Brunetti M, Tomei L, Steinkuhler C, De Francesco R (1998) Multiple enzymatic activities associated with recombinant NS3 protein of hepatitis C virus. *J. Virol* 72: 6758-6769.
Goodford, PJ (1985) A Computational Procedure for Determining Energetically Favorable Binding Sites on Biologically Important Macromolecules. *J. Med. Chem.* 28: 849-857.
Goodsell, DS and Olsen AJ (1990) Automated Docking of Substrates to Proteins by Simulated Annealing. *Proteins: Structure. Function and Genetics* 8: 195-202.
Goregaoker, S. P. and Culver, J. N. (2003) Oligomerization and activity of the helicase domain of the tobacco mosaic virus 126- and 183-kilodalton replicase proteins. *J. Virol.* 77, 3549-3556.
Ha, T, Rasnik I, Cheng W, Babcock HP, Gauss GH, Lohman TM, Chu S (2002) Initiation and re-intiation of DNA unwinding by the *Escherichia coli* Rep helicase. *Nature* 419: 638-41.
He, Y., Yan, W., Coito, C., Li, Y., Gale, M., Jr., and Katze, M. G. (2003) The regulation of hepatitis C virus (HCV) internal ribsome-entry site-mediated translation by HCV replicons and nonstructural proteins. *J. Gen. Virol.* 84, 535-543.

(Continued)

*Primary Examiner*—Bruce Campell
*Assistant Examiner*—Agnieszka Boesen
(74) *Attorney, Agent, or Firm*—Hugh McTarish

(57) ABSTRACT

The inventors have discovered that an ATPase-deficient dominant-negative mutant NS3 protein of hepatitis C virus inhibits activity of the wild-type NS3 protein and inhibits replication of hepatitis C virus (HCV). The solved crystal structure of a multi-enzyme NS3 complex on a DNA substrate is also provided. The inventors have tested a peptide matching the sequence of a portion of NS3 that interacts with another NS3 molecule for inhibiting HCV replication. The peptide inhibits HCV replication. Accordingly, the invention provides a method of inhibiting HCV replication in cells infected with HCV involving transforming the cells with a vector expressing a dominant-negative mutant NS3 gene. The invention also provides a method of inhibiting HCV replication in cells infected with HCV involving administering to the cells a dominant-negative mutant NS3 protein. The invention also provides peptides and agents that inhibit HCV replication and methods of identifying agents that inhibit HCV replication.

6 Claims, 14 Drawing Sheets

OTHER PUBLICATIONS

He, T-C, Zhou S, Da Costa LT, Yu J, Kinzler KW, and Vogelstein B (1998) A simplified system for generating recombinant adenovirus. *Proc. Natl. Acad. Sci. USA* 95: 2509-14.

Huang, L., EV Sineva, MRS Hargittai, SD Sharma, M Suthar, KD Raney, CE Cameron (2004) Purification and characterization of hepatitis C virus non-structural protein 5A expressed in *Escherichia coli*. *Prot. Exp. Purif.* 37:144-153.

Khu, Y. L., Koh, E., Lim, S. P., Tan, Y. H., Brenner, S., Lim, S. G., Hong, W. J., and Goh, P. Y. (2001) Mutations that affect dimer formation and helicase activity of the hepatitis C virus helicase. *J. Virol.* 75, 205-214.

Kim, DW, Gwack Y, Han JH, Choe J (1995) C-terminal domain of the hepatitis C virus NS3 protein contains an RNA helicase activity. *Biochem Biophys Res Commun* 215: 160-166.

Kim, JL, Morgenstern KA, Griffith JP, Dwyer MD, Thomson JA, Murcko MA, Lin C, Caron PR (1998) Hepatitis C virus NS3 RNA helicase domain with a bound oligonucleotide: the crystal structure provides insights into the mode of unwinding. *Structure* 6: 89-100.

Krieger, N., Lohmann, V., and Bartenschlager, R. (2001) Enhancement of hepatitis C virus RNA replication by cell culture-adaptive mutations. *J. Virol.* 75, 4614-4624.

Kuntz, ID (1992) Structure-based strategies for drug design and discovery. *Science* 257: 1078-1082.

Kuntz, ID et al. (1982) A Geometric Approach to Macromolecule-Ligand Interactions. *J. Mol. Biol.* 161: 269-288.

Levin, MK, Wang YH, Patel SS (2004) The functional interaction of the hepatitis C virus helicase molecules is responsible for unwinding processivity. *J Biol Chem* 279: 26005-26012.

Levin, MK, Patel SS (2002) Helicase from hepatitis C virus, energetics of DNA binding. *J Biol Chem* 277: 29377-29385.

Levin, M. K. and Patel, S. S. (1999) The helicase from hepatitis C virus is active as an oligomer. *J. Biol. Chem.* 274, 31839-31846.

Lin, C, Thomson JA, Rice CM (1995) A central region in the hepatitis C virus NS4A protein allows formation of an active NS3-NS4A serine proteinase complex in vivo and in vitro. *J. Virol* 69: 4373-4380.

Locatelli, GA, Spadari S, Maga G (2002) Hepatitis C virus NS3 ATPase/helicase: an ATP switch regulates the cooperativity among the different substrate binding sites. *Biochemistry* 41: 10332-10342.

Lohmann, V., Korner, F., Koch, J., Herian, U., Theilmann, L., and Bartenschlager, R. (1999) Replication of subgenomic hepatitis C virus RNAs in a hepatoma cell line. *Science* 285, 110-113.

Lucius, Al, Maluf NK, Fischer CJ, Lohman TM (2003) General methods for analysis of sequential "n-step" kinetic mechanisms: application to single turnover kinetics of helicase-catalyzed DNA unwinding. *Biophys J* 85: 2224-39.

Martin, YC (1992) 3D Database Searching in Drug Design. *J. Med. Chem.* 35: 2145-2154.

Miranker, A and Karplus M (1991) Functionality Maps of Binding Sites: A Multiple Copy Simultaneous Search Method. *Proteins: Structure. Function and Genetics* 11: 29-34.

Morris, PD, AK Byrd, AJ Tackett, CE Cameron, P Tanega, R Ott, E Fanning, and KD Raney (2002) Hepatitis C virus NS3 and simian virus 40 T antigen helicases displace streptavidin from 5'-biotinylated oligonucleotides but not from 3'-biotinylated oligonucleotides: evidence for directional bias in translocation on single-stranded DNA. *Biochemistry* 41:2372-2378.

Mottola, G, Cardinali G, Ceccacci A, Trozzi C, Bartholomew L, Torrisi MR, Pedrazzini E, Bonatti S, Migliaccio G (2002) Hepatitis C virus nonstructural proteins are localized in a modified endoplasmic reticulum of cells expressing viral subgenomic replicons. *Virology* 293: 31-43.

Navia, MA and Murcko MA (1992) The Use of Structural Information in Drug Design. *Current Opinions in Structural Biology* 2: 202-210.

Ng, P., Parks, R.J., and Graham, F.L. (2002) Preparation of helper-dependent adenoviral vectors, pp. 371-388 in *Gene Therapy Protocols*, J.R. Morgan ed., Humana Press, Totowa, NJ.

Pang, PS, Jankowsky E, Planet PJ, Pyle AM (2002) The hepatitis C viral NS3 protein is a processive DNA helicase with cofactor enhanced RNA unwinding. *EMBO J* 21: 1168-1176.

Piccininni, S., Varaklioti, A., Nardelli, M., Dave, B., Raney, K. D., and McCarthy, J. E. (2002) Modulation of the hepatitis C virus RNA-dependent RNA polymerase activity by the non-structural (NS) 3 helicase and the NS4B membrane protein. *J. Biol. Chem.* 277, 45670-45679.

Porter, D. J. (1998) Inhibition of the hepatitis C virus helicase-associated ATPase activity by the combination of ADP, NaF, $MgCl_2$, and poly(rU). *J. Biol. Chem.* 273, 7390-7396.

Porter, D. J. (1998) A kinetic analysis of the oligonucleotide-modiluted ATPase activity of the helicase domain of the NS3 protein from hepatitis C virus. *J. Biol. Chem.* 273, 14247-14253.

Porter, DJ, Preugschat F (2000) Strand-separating activity of hepatitis C virus helicase in the absence of ATP. *Biochemistry* 39: 5166-5173.

Qin, W, Luo H, Nomura T, Hayashi N, Yamashita T, Murakami S (2002) Oligomeric interaction of hepatitis C virus NS5B is critical for catalytic activity of RNA-dependent RNA polymerase. *J. Biol Chem* 277: 2132-2137.

Raney, K. D. and Benkovic, S. J. (1995) Bacteriophage T4 Dda helicase translocates in a unidirectional fashion on single-stranded DNA. *J. Biol. Chem.* 270, 22236-22242.

Reed, K. E., Grakoui, A., and Rice, C. M. (1995) Hepatitis C virus-encoded NS2-3 protease: cleavage-site mutagenesis and requirements for bimolecular cleavage. *J. Virol.* 69, 4127-4136.

Rosenberg, S. (2001) Recent advances in the molecular biology of hepatitis C virus. *J. Mol. Biol.* 313, 451-464.

Sandig, V., et al. (2000) Optimization of the helper-dependent adenovirus system for production and potency in vivo. *Proc. Nat'l Acad. Sci. USA* 97, 1002-1007.

Serebrov, V, Pyle AM (2004) Periodic cycles of RNA unwinding and pausing by hepatitis C virus NS3 helicase. *Nature* 430: 476-480.

Tackett, A. J., Wei, L., Cameron, C. E., and Raney, K. D. (2001) Unwinding of nucleic acids by HCV NS3 helicase is sensitive to the structure of the duplex. *Nucleic Acids Res.* 29, 565-572.

Tackett, A. J., Wei, L., Cameron, C. E., and Raney, K. D. (2005) Multiple full-length NS3 molecules are required for optimal unwinding of oligonucleotide DNA in vitro. *J. Biol. Chem.* 280:10797-806.

Tan, S. L., Pause, A., Shi, Y., and Sonenberg, N. (2002) Hepatitis C therapeutics: current status and emerging strategies. *Nat. Rev. Drug Discov.* 1, 867-881.

Thoren, PE, Persson D, Lincoln P, and Norden B (2005) Membrane destabilizing properties of cell-penetrating peptides. *Biophys. Chem.* 114: 169-179.

Thoren, PE, Persson D, Isakson P, Goksor M, Onfelt A, and Norden B (2003) Uptake of analogs of pentratin, Tat(48-60) and oligoarginine in live cells. *Biochem. Biophys. Res. Commun.* 307: 100-107.

Verlinde, CLMJ, and WGJ Hol (1994) Structure-based drug design: progress, results and challenges. *Structure* 2: 577-587.

Vriend, G (1990) What if: a molecular modeling and drug design program. *J Mol Graph* 8: 52-6, 29.

Wu, C.H., Walton, C.M., and Wu, G.Y. (2002) Targeted gene transfer to liver using protein-DNA complexes, pp. 15-23 in *Gene Therapy Protocols*, J.R. Morgan ed., Humana Press, Totowa, NJ.

Xu, Z., Choi, J., Yen, T.S., Lu, W., Strohecker, A., Govindarajan, S., Chien, D., Selby, M. J., and Ou, J. (2001) Synthesis of a novel hepatitis C virus protein by ribosomal frameshift. *EMBO J.* 20, 3840-3848.

Zhang, G., et al. (2002) Surgical procedures for intravascular delivery of plasmid DNA to organs. *Meth. Enzymol.* 346,125-133.

Barenschlager, R. The NS314A proteinase of the hepatitis C virus: untraveling structure and function of an unusual enzyme and a primer target for antiviral therapy. J of Viral Hepatitis, 6:165-181, especially p. 174, col. 2, year of publication 1999.

Tokita et al., The netire nucleotide sequences of three hepatitis C virus isolates in genetic groups 7-9 and comparison with those in the other eight genetic groups. J. Gen. Virol. 79:1847-1857, year of publication 1998.

Ali, M. and Manolios, N. Peptide delivery systems. Letters in Peptide Science 8:289-294, especially p. 291, year of publication 2002.

* cited by examiner

Fig. 4

SEQUENCE LISTING

```
<160> NUMBER OF SEQ ID NOS: 8

<210> SEQ ID NO 1
<211> LENGTH: 11
<212> TYPE: PRT
<213> ORGANISM: Artificial
<220> FEATURE:
<223> OTHER INFORMATION: NS3 oligomerization inhibitor peptide

<400> SEQUENCE: 1

His Ile Asp Ala His Phe Leu Ser Gln Thr Lys
1               5                   10

<210> SEQ ID NO 2
<211> LENGTH: 25
<212> TYPE: PRT
<213> ORGANISM: Artificial
<220> FEATURE:
<223> OTHER INFORMATION: NS3-oligomerization inhibitor peptide with cell
      entry peptide

<400> SEQUENCE: 2

His Ile Asp Ala His Phe Leu Ser Gln Thr Lys Gly Gly Gly Tyr Ala
1               5                   10                  15

Arg Ala Ala Ala Arg Gln Ala Arg Ala
            20                  25
```

```
<210> SEQ ID NO 3
<211> LENGTH: 631
<212> TYPE: PRT
<213> ORGANISM: Hepatitis C virus

<400> SEQUENCE: 3

Ala Pro Ile Thr Ala Tyr Ser Gln Gln Thr Arg Gly Leu Leu Gly Cys
  1               5                  10                  15

Ile Ile Thr Ser Leu Thr Gly Arg Asp Arg Asn Gln Val Glu Gly Glu
             20                  25                  30

Val Gln Val Val Ser Thr Ala Thr Gln Ser Phe Leu Ala Thr Cys Val
         35                  40                  45

Asn Gly Val Cys Trp Thr Val Tyr His Gly Ala Gly Ser Lys Thr Leu
     50                  55                  60

Ala Gly Pro Lys Gly Pro Ile Thr Gln Met Tyr Thr Asn Val Asp Gln
 65                  70                  75                  80

Asp Leu Val Gly Trp Gln Ala Pro Gly Ala Arg Ser Leu Thr Pro
                 85                  90                  95

Cys Thr Cys Gly Ser Ser Asp Leu Tyr Leu Val Thr Arg His Ala Asp
            100                 105                 110

Val Ile Pro Val Arg Arg Gly Asp Ser Arg Gly Ser Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ala Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ser Thr Thr Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Ser Thr Gly Glu Ile Pro Phe Tyr Gly Lys
            340                 345                 350

Ala Ile Pro Ile Glu Thr Ile Lys Gly Gly Arg His Leu Ile Phe Cys
        355                 360                 365

His Ser Lys Lys Lys Cys Asp Glu Leu Ala Ala Lys Leu Ser Gly Leu
```

```
              370                 375                 380
Gly Leu Asn Ala Val Ala Tyr Tyr Arg Gly Leu Asp Val Ser Val Ile
385                 390                 395                 400

Pro Thr Ser Gly Asp Val Ile Val Val Ala Thr Asp Ala Leu Met Thr
                405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
    450                 455                 460

Thr Gly Arg Gly Arg Met Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Ser Val Arg
            500                 505                 510

Leu Arg Ala Tyr Leu Asn Thr Pro Gly Leu Pro Val Cys Gln Asp His
        515                 520                 525

Leu Glu Phe Trp Glu Ser Val Phe Thr Gly Leu Thr His Ile Asp Ala
    530                 535                 540

His Phe Leu Ser Gln Thr Lys Gln Ala Gly Asp Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Val Thr Thr Thr His Pro Ile Thr Lys Tyr Ile Met Ala Cys Met Ser
    610                 615                 620

Ala Asp Leu Glu Val Val Thr
625                 630

<210> SEQ ID NO 4
<211> LENGTH: 11
<212> TYPE: PRT
<213> ORGANISM: Artificial
<220> FEATURE:
<223> OTHER INFORMATION: Cell entry peptide

<400> SEQUENCE: 4

Tyr Ala Arg Ala Ala Ala Arg Gln Ala Arg Ala
1               5                   10

<210> SEQ ID NO 5
<211> LENGTH: 7453
<212> TYPE: DNA
<213> ORGANISM: Artificial
<220> FEATURE:
<223> OTHER INFORMATION: pShuttle-CMV
<220> FEATURE:
<221> NAME/KEY: misc_feature
<222> LOCATION: (341)..(344)
<223> OTHER INFORMATION: n is a, c, g, or t
<220> FEATURE:
<221> NAME/KEY: misc_feature
<222> LOCATION: (1242)..(1245)
<223> OTHER INFORMATION: n is a, c, g, or t
```

<400> SEQUENCE: 5

```
catcatcaat aatatacctt attttggatt gaagccaata tgataatgag ggggtggagt      60
ttgtgacgtg gcgcggggcg tgggaacggg gcggtgacg tagtagtgtg gcggaagtgt     120
gatgttgcaa gtgtggcgga acacatgtaa gcgacggatg tggcaaaagt gacgttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa nnnntaatag taatcaatta     360
cggggtcatt agttcatagc ccatatatgg agttccgcgt tacataactt acggtaaatg     420
gcccgcctgg ctgaccgccc aacgaccccc gcccattgac gtcaataatg acgtatgttc     480
ccatagtaac gccaataggg actttccatt gacgtcaatg ggtggagtat ttacggtaaa     540
ctgcccactt ggcagtacat caagtgtatc atatgccaag tacgccccct attgacgtca     600
atgacggtaa atggcccgcc tggcattatg cccagtacat gaccttatgg gactttccta     660
cttggcagta catctacgta ttagtcatcg ctattaccat ggtgatgcgg ttttggcagt     720
acatcaatgg gcgtggatag cggtttgact cacggggatt ccaagtctc cacccccattg     780
acgtcaatgg gagtttgttt tggcaccaaa atcaacggga cttccaaaa tgtcgtaaca     840
actccgcccc attgacgcaa atgggcggta ggcgtgtacg gtgggaggtc tatataagca     900
gagctggttt agtgaaccgt cagatccgct agagatctgg taccgtcgac gcggccgctc     960
gagcctaagc ttctagataa gatatccgat ccaccggatc tagataactg atcataatca    1020
gccataccac atttgtagag gttttacttg ctttaaaaaa cctcccacac ctccccctga    1080
acctgaaaca taaaatgaat gcaattgttg ttgttaactt gtttattgca gcttataatg    1140
gttacaaata aagcaatagc atcacaaatt tcacaaataa agcatttttt tcactgcatt    1200
ctagttgtgg tttgtccaaa ctcatcaatg tatcttaacg cnnnntaagg gtgggaaaga    1260
atatataagg tgggggtctt atgtagtttt gtatctgttt tgcagcagcc gccgccgcca    1320
tgagcaccaa ctcgtttgat ggaagcattg tgagctcata tttgacaacg cgcatgcccc    1380
catgggccgg ggtgcgtcag aatgtgatgg gctccagcat tgatggtcgc cccgtcctgc    1440
ccgcaaactc tactaccttg acctacgaga ccgtgtctgg aacgccgttg gagactgcag    1500
cctccgccgc cgcttcagcc gctgcagcca ccgcccgcgg gattgtgact gactttgctt    1560
tcctgagccc gcttgcaagc agtgcagctt cccgttcatc cgcccgcgat gacaagttga    1620
cggctctttt ggcacaattg gattctttga cccgggaact taatgtcgtt tctcagcagc    1680
tgttggatct gcgccagcag gtttctgccc tgaaggcttc ctcccctccc aatgcggttt    1740
aaaacataaa taaaaaacca gactctgttt ggatttggat caagcaagtg tcttgctgtc    1800
tttatttagg ggttttgcgc gcgcggtagg cccgggacca gcggtctcgg tcgttgaggg    1860
tcctgtgtat ttttccagg acgtggtaaa ggtgactctg gatgttcaga tacatgggca    1920
taagcccgtc tctggggtgg aggtagcacc actgcagagc ttcatgctgc ggggtggtgt    1980
tgtagatgat ccagtcgtag caggagcgct gggcgtggtg cctaaaaatg tctttcagta    2040
gcaagctgat tgccaggggc aggcccttgg tgtaagtgtt tacaaagcgg ttaagctggg    2100
atgggtgcat acgtggggat atgagatgca tcttggactg tattttagg ttggctatgt    2160
tcccagccat atccctccgg ggattcatgt tgtgcagaac caccagcaca gtgtatccgg    2220
tgcacttggg aaatttgtca tgtagcttag aaggaaatgc gtggaagaac ttggagacgc    2280
ccttgtgacc tccaagattt tccatgcatt cgtccataat gatggcaatg ggcccacggg    2340
```

```
cggcggcctg ggcgaagata tttctgggat cactaacgtc atagttgtgt tccaggatga    2400
gatcgtcata ggccattttt acaaagcgcg ggcggagggt gccagactgc ggtataatgg    2460
ttccatccgg cccaggggcg tagttaccct cacagatttg catttcccac gctttgagtt    2520
cagatggggg gatcatgtct acctgcgggg cgatgaagaa aacggtttcc ggggtagggg    2580
agatcagctg ggaagaaagc aggttcctga gcagctgcga cttaccgcag ccggtgggcc    2640
cgtaaatcac acctattacc gggtgcaact ggtagttaag agagctgcag ctgccgtcat    2700
ccctgagcag gggggccact tcgttaagca tgtccctgac tcgcatgttt tccctgacca    2760
aatccgccag aaggcgctcg ccgcccagcg atagcagttc ttgcaaggaa gcaaagtttt    2820
tcaacggttt gagaccgtcc gccgtaggca tgcttttgag cgtttgacca agcagttcca    2880
ggcggtccca cagctcggtc acctgctcta cggcatctcg atccagcata tctcctcgtt    2940 tcgcggggttg gggcggcttt cgctgtacgg cagtagtcgg tgctcgtcca dacgggccag    3000
```

```
tatccacaga atcaggggat aacgcaggaa agaacatgtg agcaaaaggc cagcaaaagg    4740
ccaggaaccg taaaaaggcc gcgttgctgg cgttttttcca taggctccgc ccccctgacg    4800
agcatcacaa aaatcgacgc tcaagtcaga ggtggcgaaa cccgacagga ctataaagat    4860
accaggcgtt tcccccctgga agctccctcg tgcgctctcc tgttccgacc ctgccgctta    4920
ccggatacct gtccgccttt ctcccttcgg aagcgtggc gctttctcat agctcacgct    4980
gtaggtatct cagttcggtg taggtcgttc gctccaagct gggctgtgtg cacgaacccc    5040
ccgttcagcc cgaccgctgc gccttatccg gtaactatcg tcttgagtcc aacccggtaa    5100
gacacgactt atcgccactg gcagcagcca ctggtaacag gattagcaga gcgaggtatg    5160
taggcggtgc tacagagttc ttgaagtggt ggcctaacta cggctacact agaaggacag    5220
tatttggtat ctgcgctctg ctgaagccag ttaccttcgg aaaaagagtt ggtagctctt    5280
gatccggcaa acaaaccacc gctggtagcg gtggttttt tgtttgcaag cagcagatta    5340
cgcgcagaaa aaaaggatct caagaagatc ctttgatctt ttctacgggg tctgacgctc    5400
agtggaacga aaactcacgt taagggattt tggtcatgag attatcaaaa aggatcttca    5460
cctagatcct tttaaattaa aaatgaagtt ttaaatcaat ctaaagtata tatgagtaaa    5520
cttggtctga cagttaccaa tgcttaatca gtgaggcacc tatctcagcg atctgtctat    5580
ttcgttcatc catagttgcc tgactccccg tcgtgtagat aactacgata cgggagggct    5640
taccatctgg ccccagtgct gcaatgatac cgcgagaccc acgctcaccg gctccagatt    5700
tatcagcaat aaaccagcca gccggaaggg ccgagcgcag aagtggtcct gcaactttat    5760
ccgcctccat ccagtctatt aattgttgcc gggaagctag agtaagtagt tcgccagtta    5820
atagtttgcg caacgttgtt gccattgctg cagccatgag attatcaaaa aggatcttca    5880
cctagatcct tttcacgtag aaagccagtc cgcagaaacg gtgctgaccc cggatgaatg    5940
tcagctactg ggctatctgg acaagggaaa acgcaagcgc aaagagaaag caggtagctt    6000
gcagtgggct tacatggcga tagctagact gggcggtttt atggacagca agcgaaccgg    6060
aattgccagc tggggcgccc tctggtaagg ttgggaagcc ctgcaaagta actggatgg    6120 ctttcttgcc gccaaggatc tgatggcgca ggggatcaag ctctgatcaa gagacaggat    6180
gaggatcgtt tcgcatgatt gaacaagatg gattgcacgc aggttctccg gccgcttggg    6240
tggagaggct attcggctat gactgggcac aacagacaat cggctgctct gatgccgccg    6300
tgttccggct gtcagcgcag gggcgcccgg ttcttttttgt caagaccgac ctgtccggtg    6360
ccctgaatga actgcaagac gaggcagcgc ggctatcgtg gctggccacg acgggcgttc    6420
cttgcgcagc tgtgctcgac gttgtcactg aagcgggaag ggactggctg ctattgggcg    6480
aagtgccggg gcaggatctc ctgtcatctc accttgctcc tgccgagaaa gtatccatca    6540
tggctgatgc aatgcggcgg ctgcatacgc ttgatccggc tacctgccca ttcgaccacc    6600
aagcgaaaca tcgcatcgag cgagcacgta ctcggatgga gccggtcttt gtcgatcagg    6660
atgatctgga cgaagagcat caggggctcg cgccagccga actgttcgcc aggctcaagg    6720
cgagcatgcc cgacgcgag gatctcgtcg tgacccatgg cgatgcctgc ttgccgaata    6780
tcatggtgga aaatggccgc ttttctggat tcatcgactg tggccggctg ggtgtggcgg    6840
accgctatca ggacatagcg ttggctaccc gtgatattgc tgaagagctt ggcggcgaat    6900
gggctgaccg cttcctcgtg ctttacggta tcgccgctcc cgattcgcag cgcatcgcct    6960
tctatcgcct tcttgacgag ttcttctgaa ttttgttaaa attttttgtta aatcagctca    7020 ttttttaacc aataggccga aatcggcaac atcccttata aatcaaaaga atagaccgcg    7080
```

-continued

| | |
|---|---|
| ataggggttga gtgttgttcc agtttggaac aagagtccac tattaaagaa cgtggactcc | 7140 |
| aacgtcaaag ggcgaaaaac cgtctatcag ggcgatggcc cactacgtga accatcaccc | 7200 |
| aaatcaagtt ttttgcggtc gaggtgccgt aaagctctaa atcggaaccc taaagggagc | 7260 |
| ccccgattta gagcttgacg gggaaagccg cgaacgtgg cgagaaagga agggaagaaa | 7320 |
| gcgaaaggag cgggcgctag ggcgctggca agtgtagcgg tcacgctgcg cgtaaccacc | 7380 |
| acacccgcgc gcttaatgcg ccgctacagg gcgcgtccat tcgccattca ggatcgaatt | 7440 |
| aattcttaat taa | 7453 |

<210> SEQ ID NO 6
<211> LENGTH: 9605
<212> TYPE: DNA
<213> ORGANISM: Hepatitis C virus

<400> SEQUENCE: 6

| | |
|---|---|
| gccagccccc gattgggggc gacactccac catagatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tccttttcttg atcaacccgc tcaatgcct ggagatttgg gcgtgccccc | 240 |
| gcgagactgc tagccgagta tgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaacgt aacaccaacc gccgcccaca ggacgtcaag ttcccgggcg | 420 |
| gtggtcagat cgtcggtgga gtttacctgt tgccgcgcag gggccccagg ttgggtgtgc | 480 |
| gcgcgactag gaagacttcc gagcggtcgc aacctcgtgg aaggcgacaa cctatcccca | 540 |
| aggctcgcca gcccgagggt agggcctggg ctcagcccgg gtaccctggg cccctctatg | 600 |
| gcaatgaggg cttgggggtgg gcaggatggc tcctgtcacc ccgtggctct cggcctagtt | 660 |
| ggggccccac ggaccccgg cgtaggtcgc gcaatttggg taaggtcatc gatacccctca | 720 |
| cgtgcggctt cgccgatctc atggggtaca ttccgctcgt cggcgccccc ctaggggggcg | 780 |
| ctgccagggc cctggcgcat ggcgtccggg ttctggagga cggcgtgaac tatgcaacag | 840 |
| ggaatctgcc cggttgctcc ttttctatct tccttttggc tttgctgtcc tgtttgacca | 900 |
| tcccagcttc cgcttatgaa gtgcgcaacg tatccggagt gtaccatgtc acgaacgact | 960 |
| gctccaacgc aagcattgtg tatgaggcag cggacatgat catgcatacc cccgggtgcg | 1020 |
| tgccctgcgt tcgggagaac aactcctccc gctgctgggt agcgctcact cccacgctcg | 1080 |
| cggccaggaa cgctagcgtc cccactacga cgatacgacg ccatgtcgat ttgctcgttg | 1140 |
| gggcggctgc tctctgctcc gctatgtacg tgggagatct ctgcggatct gttttcctcg | 1200 |
| tcgcccagct gttcaccttc tcgcctcgcc ggcacgagac agtacaggac tgcaattgct | 1260 |
| caatatatcc cggccacgtg acaggtcacc gtatggcttg ggatatgatg atgaactggt | 1320 |
| cacctacagc agcccctagtg gtatcgcagt tactccggat cccacaagct gtcgtggata | 1380 |
| tggtggcggg ggcccattgg ggagtcctag cgggccttgc ctactattcc atggtgggga | 1440 |
| actgggctaa ggttctgatt gtgatgctac tctttgccgg cgttgacggg gaacctatg | 1500 |
| tgacaggggg gacgatggcc aaaaacaccc tcggattac gtccctctttt tcacccgggt | 1560 |
| catcccagaa aatccagctt gtaaacacca acggcagctg gcacatcaac aggactgccc | 1620 |
| tgaactgcaa tgactccctc aacactgggt tccttgctgc gctgttctac gtgcacaagt | 1680 |

```
tcaactcatc tggatgccca gagcgcatgg ccagctgcag ccccatcgac gcgttcgctc    1740
aggggtgggg gcccatcact tacaatgagt cacacagctc ggaccagagg ccttattgtt    1800
ggcactacgc accccggccg tgcggtatcg tacccgcggc gcaggtgtgt ggtccagtgt    1860
actgcttcac cccaagccct gtcgtggtgg ggacgaccga ccggttcggc gtccctacgt    1920
acagttgggg ggagaatgag acggacgtgc tgcttcttaa caacacgcgg ccgccgcaag    1980
gcaactggtt tggctgtaca tggatgaata gcactgggtt caccaagacg tgcggggggcc    2040
ccccgtgtaa catcgggggg atcggcaata aaaccttgac ctgccccacg gactgcttcc    2100
ggaagcaccc cgaggccact tacaccaagt gtggttcggg gccttggttg acacccagat    2160
gcttggtcca ctaccatac aggctttggc actaccctg cactgtcaac tttaccatct    2220
tcaaggttag gatgtacgtg gggggagtgg agcacaggct cgaagccgca tgcaattgga    2280
ctcgaggaga gcgttgtaac ctggaggaca gggacagatc agagcttagc ccgctgctgc    2340
tgtctacaac ggagtggcag gtattgccct gttccttcac cacctaccg gctctgtcca    2400
ctggtttgat ccatctccat cagaacgtcg tggacgtaca atacctgtac ggtatagggt    2460
cggcggttgt ctcctttgca atcaaatggg agtatgtcct gttgctcttc cttcttctgg    2520
cggacgcgcg cgtctgtgcc tgcttgtgga tgatgctgct gatagctcaa gctgaggccg    2580
ccctagagaa cctggtggtc ctcaacgcgg catccgtggc cggggcgcat ggcattctct    2640
ccttcctcgt gttcttctgt gctgcctggt acatcaaggg caggctggtc cctggggcgg    2700
catatgccct ctacggcgta tggccgctac tcctgctcct gctggcgtta ccaccacgag    2760
catacgccat ggaccgggag atggcagcat cgtgcggagg cgcggttttc gtaggtctga    2820
tactcttgac cttgtcaccg cactataagc tgttcctcgc taggctcata tggtggttac    2880
aatatttat caccagggcc gaggcacact tgcaagtgtg gatcccccc ctcaacgttc    2940
gggggggccg cgatgccgtc atcctcctca cgtgcgcgat ccaccagag ctaatcttta    3000
ccatcaccaa aatcttgctc gccatactcg gtccactcat ggtgctccag gctggtataa    3060
ccaaagtgcc gtacttcgtg cgcgcacacg ggctcattcg tgcatgcatg ctggtgcgga    3120
aggttgctgg gggtcattat gtccaaatgg ctctcatgaa gttggccgca ctgacaggta    3180
cgtacgttta tgaccatctc accccactgc gggactgggc ccacgcgggc ctacgagacc    3240
ttgcggtggc agttgagccc gtcgtcttct ctgatatgga gaccaaggtt atcacctggg    3300
gggcagacac cgcggcgtgt ggggacatca tcttgggcct gcccgtctcc gcccgcaggg    3360
ggagggagat acatctggga ccggcagaca gccttgaagg gcaggggtgg cgactcctcg    3420
cgcctattac ggcctactcc aacagacgc gaggcctact tggctgcatc atcactagcc    3480
tcacaggccg ggacaggaac caggtcgagg gggaggtcca agtggtctcc accgcaacac    3540
aatctttcct ggcgacctgc gtcaatggcg tgtgttggac tgtctatcat ggtgccggct    3600
caaagaccct tgccggccca aagggcccaa tcacccaaat gtacaccaat gtggaccagg    3660
acctcgtcgg ctggcaagcg ccccccgggg cgcgttcctt gacaccatgc acctgcggca    3720
gctcggacct ttacttggtc acgaggcatg ccgatgtcat tccggtgcgc cggcggggcg    3780
acagcagggg gagcctactc tcccccaggc ccgtctccta cttgaagggc tcttcgggcg    3840
gtccactgct ctgcccctcg gggcacgctg tgggcatctt tcgggctgcc gtgtgcaccc    3900
gaggggttgc gaaggcggtg gactttgtac ccgtcgagtc tatggaaacc actatgcggt    3960
ccccggtctt cacggacaac tcgtcccctc cggccgtacc gcagacattc caggtggccc    4020
atctacacgc ccctactggt agcggcaaga gcactaaggt gccggctgcg tatgcagccc    4080
```

```
aagggtataa ggtgcttgtc ctgaacccgt ccgtcgccgc caccctaggt ttcggggcgt    4140
atatgtctaa ggcacatggt atcgaccta acatcagaac cggggtaagg accatcacca    4200
cgggtgcccc catcacgtac tccacctatg gcaagtttct tgccgacggt ggttgctctg    4260
ggggcgccta tgacatcata atatgtgatg agtgccactc aactgactcg accactatcc    4320
tgggcatcgg cacagtcctg gaccaagcgg agacggctgg agcgcgactc gtcgtgctcg    4380
ccaccgctac gcctccggga tcggtcaccg tgccacatcc aaacatcgag gaggtggctc    4440
tgtccagcac tggagaaatc cccttttatg gcaaagccat ccccatcgag accatcaagg    4500
gggggaggca cctcatttc tgccattcca agaagaaatg tgatgagctc gccgcgaagc    4560
tgtccggcct cggactcaat gctgtagcat attaccgggg ccttgatgta tccgtcatac    4620
caactagcgg agacgtcatt gtcgtagcaa cggacgctct aatgacgggc tttaccggcg    4680
atttcgactc agtgatcgac tgcaatacat gtgtcaccca gacagtcgac ttcagcctgg    4740
acccgacctt caccattgag acgacgaccg tgccacaaga cgcggtgtca cgctcgcagc    4800
ggcgaggcag gactggtagg ggcaggatgg gcatttacag gtttgtgact ccaggagaac    4860
ggccctcggg catgttcgat tcctcggttc tgtgcgagtg ctatgacgcg ggctgtgctt    4920
ggtacgagct cacgcccgcc gagacctcag ttaggttgcg ggcttaccta aacacaccag    4980
ggttgcccgt ctgccaggac catctggagt tctgggagag cgtctttaca ggcctcaccc    5040
acatagacgc ccatttcttg tcccagacta agcaggcagg agacaacttc ccctacctgg    5100
tagcatacca ggctacggtg tgcgccaggg ctcaggctcc acctccatcg tgggaccaaa    5160
tgtggaagtg tctcatacgg ctaaagccta cgctgcacgg gccaacgccc ctgctgtata    5220
ggctgggagc cgttcaaaac gaggttacta ccacacaccc cataaccaaa tacatcatgg    5280
catgcatgtc ggctgacctg gaggtcgtca cgagcacctg ggtgctggta ggcggagtcc    5340
tagcagctct ggccgcgtat tgcctgacaa caggcagcgt ggtcattgtg gcaggatca    5400 tcttgtccgg aaagccggcc atcattcccg acagggaagt cctttaccgg gagttcgatg    5460
agatggaaga gtgcgcctca cacctccctt acatcgaaca gggaatgcag ctcgccgaac    5520
aattcaaaca gaaggcaatc gggttgctgc aaacagccac caagcaagcg gaggctgctg    5580
ctcccgtggt ggaatccaag tggcggaccc tcgaagcctt ctgggcgaag catatgtgga    5640
atttcatcag cgggatacaa tattagcag gcttgtccac tctgctggc aaccccgcga    5700 tagcatcact gatggcattc acagcctcta tcaccagccc gctcaccacc caacataccc    5760
tcctgtttaa catcctgggg ggatgggtgg ccgcccaact tgctcctccc agcgctgctt    5820
ctgctttcgt aggcgccggc atcgctggag cggctgttgg cagcataggc cttgggaagg    5880
tgcttgtgga tattttggca ggttatggag caggggtggc aggcgcgctc gtggccttta    5940
aggtcatgag cggcgagatg cccctccaccg aggacctggt taacctactc cctgctatcc    6000
tctcccctgg cgccctagtc gtcggggtcg tgtgcgcagc gatactgcgt cggcacgtgg    6060
gcccagggga gggggctgtg cagtggatga accggctgat agcgttcgct tcgcggggta    6120
accacgtctc ccccacgcac tatgtgcctg agagcgacgc tgcagcacgt gtcactcaga    6180
tcctctctag tcttaccatc actcagctgc tgaagaggct tcaccagtgg atcaacgagg    6240
actgctccac gccatgctcc ggctcgtggc taagagatgt ttgggattgg atatgcacgg    6300
tgttgactga tttcaagacc tggctccagt ccaagctcct gccgcgattg ccgggagtcc    6360
ccttcttctc atgtcaacgt gggtacaagg gagtctggcg gggcgacggc atcatgcaaa    6420
```

-continued

```
ccacctgccc atgtggagca cagatcaccg gacatgtgaa aaacggttcc atgaggatcg    6480
tggggcctag gacctgtagt aacacgtggc atggaacatt ccccattaac gcgtacacca    6540
cgggcccctg cacgccctcc ccggcgccaa attattctag ggcgctgtgg cgggtggctg    6600
ctgaggagta cgtggaggtt acgcgggtgg gggatttcca ctacgtgacg ggcatgacca    6660
ctgacaacgt aaagtgcccg tgtcaggttc cggcccccga attcttcaca gaagtggatg    6720
gggtgcggtt gcacaggtac gctccagcgt gcaaacccct cctacgggag gaggtcacat    6780
tcctggtcgg gctcaatcaa tacctggttg ggtcacagct cccatgcgag cccgaaccgg    6840
acgtagcagt gctcacttcc atgctcaccg accccctccca cattacgcgc gagacggcta    6900
agcgtaggct ggccagggga tctcccccct ccttggccag ctcatcagct agccagctgt    6960
ctgcgccttc cttgaaggca acatgcacta cccgtcatga ctccccggac gctgacctca    7020
tcgaggccaa cctcctgtgg cggcaggaga tgggcgggaa catcacccgc gtggagtcag    7080
aaaataaggt agtaattttg gactctttcg agccgctcca agcggaggag gatgagaggg    7140
aagtatccgt tccggcggag atcctgcgga ggtccaggaa attccctcga gcgatgccca    7200
tatgggcacg cccggattac aaccctccac tgttagagtc ctggaaggac ccggactacg    7260
tccctccagt ggtacacggg tgtccattgc cgcctgccaa ggcccctccg ataccacctc    7320
cacggaggaa gaggacggtt gtcctgtcag aatctaccgt gtcttctgcc ttggcggagc    7380
tcgccacaaa gaccttcggc agctccgaat cgtcggccgt cgacagcggc acggcaacgg    7440
cctctcctga ccagccctcc gacgacgcg acgcgggatc cgacgttgag tcgtactcct    7500
ccatgccccc ccttgagggg gagccggggg atcccgatct cagcgacggg tcttggtcta    7560
ccgtaagcga ggaggctagt gaggacgtcg tctgctgctc gatgtcctac acatggacag    7620
gcgccctgat cacgccatgc gctgcggagg aaaccaagct gcccatcaat gcactgagca    7680
actctttgct ccgtcaccac aacttggtct atgctacaac atctcgcagc gcaagcctgc    7740
ggcagaagaa ggtcacccttt gacagactgc aggtcctgga cgaccactac cgggacgtgc    7800
tcaaggagat gaaggcgaag gcgtccacag ttaaggctaa acttctatcc gtggaggaag    7860
cctgtaagct gacgccccca cattcggcca gatctaaatt tggctatggg gcaaaggacg    7920
tccggaacct atccagcaag gccgttaacc acatccgctc cgtgtggaag gacttgctgg    7980
aagacactga gacaccaatt gacaccacca tcatggcaaa aaatgaggtt ttctgcgtcc    8040
aaccagagaa ggggggccgc aagccagctc gccttatcgt attcccagat ttggggggttc    8100
gtgtgtgcga gaaaatggcc ctttacgatg tggtctccac cctccctcag gccgtgatgg    8160
gctcttcata cggattccaa tactctcctg gacagcgggt cgagttcctg gtgaatgcct    8220
ggaaagcgaa gaaatgccct atgggcttcg catatgacac ccgctgtttt gactcaacgg    8280
tcactgagaa tgacatccgt gttgaggagt caatctacca atgttgtgac ttggccccgc    8340
aagccagaca ggccataagg tcgctcacag agcggcttta tcgggggc ccctgactca    8400
attctaaagg gcagaactgc ggctatcgcc ggtgccgcgc gagcggtgta ctgacgacca    8460
gctgcggtaa taccctcaca tgttacttga aggccgctgc ggcctgtcga gctgcgaagc    8520
tccaggactg cacgatgctc gtatgcggag acgaccttgt cgttatctgt gaaagcgcgg    8580
ggacccaaga ggacgaggcg agcctacggg ccttcacgga ggctatgact agatactctg    8640
cccccctgg ggaccgccc aaaccagaat acgacttgga gttgataaca tcatgctcct    8700
ccaatgtgtc agtcgcgcac gatgcatctg caaaagggt gtactatctc acccgtgacc    8760
ccaccacccc ccttgcgcgg gctgcgtggg agacagctag acacactcca gtcaattcct    8820
```

| | | | | | |
|---|---|---|---|---|---|
| ggctaggcaa | catcatcatg | tatgcgccca | ccttgtgggc | aaggatgatc | ctgatgactc | 8880 |
| atttcttctc | catccttcta | gctcaggaac | aacttgaaaa | agccctagat | tgtcagatct | 8940 |
| acggggcctg | ttactccatt | gagccacttg | acctacctca | gatcattcaa | cgactccatg | 9000 |
| gccttagcgc | attttcactc | catagttact | ctccaggtga | gatcaatagg | gtggcttcat | 9060 |
| gcctcaggaa | acttgggta | ccgcccttgc | gagtctggag | acatcgggcc | agaagtgtcc | 9120 |
| gcgctaggct | actgtcccag | gggggaggg | ctgccacttg | tggcaagtac | ctcttcaact | 9180 |
| gggcagtaag | gaccaagctc | aaactcactc | caatcccggc | tgcgtcccag | ttggatttat | 9240 |
| ccagctggtt | cgttgctggt | tacagcgggg | gagacatata | tcacagcctg | tctcgtgccc | 9300 |
| gaccccgctg | gttcatgtgg | tgcctactcc | tactttctgt | aggggtaggc | atctatctac | 9360 |
| tccccaaccg | atgaacgggg | agctaaacac | tccaggccaa | taggccatcc | tgttttttc | 9420 |
| ccttttttt | tttctttttt | tttttttttt | tttttttttt | tttttttct | ccttttttt | 9480 |
| tcctctttt | ttccttttct | ttcctttggt | ggctccatct | tagccctagt | cacggctagc | 9540 |
| tgtgaaaggt | ccgtgagccg | cttgactgca | gagagtgctg | atactggcct | ctctgcagat | 9600 |
| caagt | | | | | | 9605 |

<210> SEQ ID NO 7
<211> LENGTH: 33450
<212> TYPE: DNA
<213> ORGANISM: Artificial
<220> FEATURE:
<223> OTHER INFORMATION: pAdEasy vector
<220> FEATURE:
<221> NAME/KEY: misc_feature
<222> LOCATION: (3661)..(3663)
<223> OTHER INFORMATION: n is a, c, g, or t
<220> FEATURE:
<221> NAME/KEY: misc_feature
<222> LOCATION: (3690)..(3692)
<223> OTHER INFORMATION: n is a, c, g, or t
<220> FEATURE:
<221> NAME/KEY: misc_feature
<222> LOCATION: (31177)..(31177)
<223> OTHER INFORMATION: n is a, c, g, or t
<220> FEATURE:
<221> NAME/KEY: misc_feature
<222> LOCATION: (32866)..(32866)
<223> OTHER INFORMATION: n is a, c, g, or t

<400> SEQUENCE: 7

| | | | | | |
|---|---|---|---|---|---|
| ttaattaaca | tgcatggatc | ctcgtctcga | cgatgcccct | gagagccttc | aacccagtca | 60 |
| gctccttccg | gtgggcgcgg | ggcatgacta | tcgtcgccgc | acttatgact | gtcttcttta | 120 |
| tcatgcaact | cgtaggacag | gtgccggcag | cgctctgggt | cattttcggc | gaggaccgct | 180 |
| ttcgctggag | cgcgacgatg | atcggcctgt | cgcttgcggt | attcggaatc | ttgcacgccc | 240 |
| tcgctcaagc | cttcgtcact | ggtcccgcca | ccaaacgttt | cggcgagaag | caggccatta | 300 |
| tcgccggcat | ggcggccgac | gcgctgggct | acgtcttgct | ggcgttcgcg | acgcgaggct | 360 |
| ggatggcctt | ccccattatg | attcttctcg | cttccggcgg | catcgggatg | cccgcgttgc | 420 |
| aggccatgct | gtccaggcag | gtagatgacg | accatcaggg | acagcttcaa | ggatcgctcg | 480 |
| cggctcttac | cagcctaact | tcgatcactg | gaccgctgat | cgtcacgcg | atttatgccg | 540 |
| cctcggcgag | cacatggaac | gggttggcat | ggattgtagg | cgccgcccta | taccttgtct | 600 |
| gcctccccgc | gttgcgtcgc | ggtgcatgga | gccgggccac | ctcgacctga | atggaagccg | 660 |
| gcggcacctc | gctaacggat | tcaccactcc | aagaattgga | gccaatcaat | tcttgcggag | 720 |

```
aactgtgaat gcgcaaacca acccttggca gaacatatcc atcgcgtccg ccatctccag    780
cagccgcacg cggcgcatct cgggcagcgt tgggtcctgg ccacgggtgc gcatgatcgt    840
gctcctgtcg ttgaggaccc ggctaggctg gcggggttgc cttactggtt agcagaatga    900
atcaccgata cgcgagcgaa cgtgaagcga ctgctgctgc aaaacgtctg cgacctgagc    960
aacaacatga atggtcttcg gtttccgtgt ttcgtaaagt ctggaaacgc ggaagtcagc   1020
gccctgcacc attatgttcc ggatctgcat cgcaggatgc tgctggctac cctgtggaac   1080
acctacatct gtattaacga agcgctggca ttgaccctga gtgattttc tctggtcccg    1140
ccgcatccat accgccagtt gtttaccctc acaacgttcc agtaaccggg catgttcatc   1200
atcagtaacc cgtatcgtga gcatcctctc tcgtttcatc ggtatcatta cccccatgaa   1260
cagaaattcc cccttacacg gaggcatcaa gtgaccaaac aggaaaaaac cgcccttaac   1320
atggcccgct ttatcagaag ccagacatta acgcttctgg agaaactcaa cgagctggac   1380
gcggatgaac aggcagacat ctgtgaatcg cttcacgacc acgctgatga gctttaccgc   1440
agctgcctcg cgcgtttcgg tgatgacggt gaaaacctct gacacatgca gctcccggag   1500
acggtcacag cttgtctgta gcggatgcc gggagcagca agcccgtca gggcgcgtca     1560
gcgggtgttg gcgggtgtcg gggcgcagcc atgacccagt cacgtagcga tagcggagtg   1620
tatactggct taactatgcg gcatcagagc agattgtact gagagtgcac catatgcggt   1680
gtgaaatacc gcacagatgc gtaaggagaa ataccgcat caggcgctct ccgcttcct     1740
cgctcactga ctcgctgcgc tcggtcgttc ggctgcggcg agcggtatca gctcactcaa   1800
aggcggtaat acggttatcc acagaatcag gggataacgc aggaaagaac atgtgagcaa   1860
aaggccagca aaaggccagg aaccgtaaaa aggccgcgtt gctggcgttt ttccataggc   1920
tccgcccccc tgacgagcat cacaaaaatc gacgctcaag tcagaggtgg cgaaacccga   1980
caggactata aagataccag gcgtttcccc ctggaagctc cctcgtgcgc tctcctgttc   2040
cgaccctgcc gcttaccgga tacctgtccg cctttctccc ttcgggaagc gtggcgcttt   2100
ctcaatgctc acgctgtagg tatctcagtt cggtgtaggt cgttcgctcc aagctgggct   2160
gtgtgcacga accccccgtt cagcccgacc gctgcgcctt atccggtaac tatcgtcttg   2220
agtccaaccc ggtaagacac gacttatcgc cactggcagc agccactggt aacaggatta   2280
gcagagcgag gtatgtaggc ggtgctacag agttcttgaa gtggtggcct aactacggct   2340
acactagaag gacagtattt ggtatctgcg ctctgctgaa gccagttacc ttcggaaaaa   2400
gagttggtag ctcttgatcc ggcaaacaaa ccaccgctgg tagcggtggt ttttttgttt   2460
gcaagcagca gattacgcgc agaaaaaaag gatctcaaga agatcctttg atcttttcta   2520
cggggtctga cgctcagtgg aacgaaaact cacgttaagg gattttggtc atgagattat   2580
caaaaaggat cttcacctag atccttttaa attaaaaatg aagttttaaa tcaatctaaa   2640
gtatatatga gtaaacttgg tctgacagtt accaatgctt aatcagtgag gcacctatct   2700
cagcgatctg tctatttcgt tcatccatag ttgcctgact ccccgtcgtg tagataacta   2760
cgatacggga gggcttacca tctggcccca gtgctgcaat gataccgcga gacccacgct   2820
caccggctcc agatttatca gcaataaacc agccagccgg aagggccgag cgcagaagtg   2880
gtcctgcaac tttatccgcc tccatccagt ctattaattg ttgccgggaa gctagagtaa   2940
gtagttcgcc agttaatagt ttgcgcaacg ttgttgccat tgctgcaggc atcgtggtgt   3000
cacgctcgtc gtttggtatg gcttcattca gctccggttc ccaacgatca aggcgagtta   3060
catgatcccc catgttgtgc aaaaaagcgg ttagctcctt cggtcctccg atcgttgtca   3120
```

```
gaagtaagtt ggccgcagtg ttatcactca tggttatggc agcactgcat aattctctta    3180
ctgtcatgcc atccgtaaga tgcttttctg tgactggtga gtactcaacc aagtcattct    3240
gagaatagtg tatgcggcga ccgagttgct cttgcccggc gtcaacacgg gataataccg    3300
cgccacatag cagaacttta aaagtgctca tcattggaaa acgttcttcg gggcgaaaac    3360
tctcaaggat cttaccgctg ttgagatcca gttcgatgta acccactcgt gcacccaact    3420
gatcttcagc atcttttact ttcaccagcg tttctgggtg agcaaaaaca ggaaggcaaa    3480
atgccgcaaa aaagggaata agggcgacac ggaaatgttg aatactcata ctcttccttt    3540
ttcaatatta ttgaagcatt tatcagggtt attgtctcat gagcggatac atatttgaat    3600
gtatttagaa aaataaacaa ataggggttc cgcgcacatt tccccgaaaa gtgccacctg    3660
nnngaattcg aatctagtat cgattcgaan nncttaaggg tgggaaagaa tatataaggt    3720
gggggtctta tgtagttttg tatctgtttt gcagcagccg ccgccgccat gagcaccaac    3780
tcgtttgatg gaagcattgt gagctcatat ttgacaacgc gcatgccccc atgggccggg    3840
gtgcgtcaga atgtgatggg ctccagcatt gatggtcgcc ccgtcctgcc cgcaaactct    3900
actaccttga cctacgagac cgtgtctgga acgccgttgg agactgcagc ctccgccgcc    3960
gcttcagccg ctgcagccac cgcccgcggg attgtgactg actttgcttt cctgagcccg    4020
cttgcaagca gtgcagcttc ccgttcatcc gcccgcgatg acaagttgac ggctcttttg    4080
gcacaattgg attctttgac ccgggaactt aatgtcgttt ctcagcagct gttggatctg    4140
cgccagcagg tttctgccct gaaggcttcc tcccctccca atgcggttta aaacataaat    4200
aaaaaaccag actctgtttg gatttggatc aagcaagtgt cttgctgtct ttatttaggg    4260
gttttgcgcg cgcggtaggc ccgggaccag cggtctcggt cgttgagggt cctgtgtatt    4320
ttttccagga cgtggtaaag gtgactctgg atgttcagat acatgggcat aagcccgtct    4380
ctggggtgga ggtagcacca ctgcagagct tcatgctgcg gggtggtgtt gtagatgatc    4440
cagtcgtagc aggagcgctg ggcgtggtgc ctaaaaatgt cttcagtag caagctgatt    4500 gccaggggca ggcccttggt gtaagtgttt acaaagcggt taagctggga tgggtgcata    4560
cgtggggata tgagatgcat cttggactgt attttaggt tggctatgtt cccagccata    4620
tccctccggg gattcatgtt gtgcagaacc accagcacag tgtatccggt gcacttggga    4680
aatttgtcat gtagcttaga aggaaatgcg tggaagaact tggagacgcc cttgtgacct    4740
ccaagatttt ccatgcattc gtccataatg atggcaatgg gcccacgggc ggcggcctgg    4800
gcgaagatat ttctgggatc actaacgtca tagttgtgtt ccaggatgag atcgtcatag    4860 gccatttta caaagcgcgg gcggagggtg ccagactgcg gtataatggt tccatccggc    4920
ccaggggcgt agttaccctc acagatttgc atttcccacg ctttgagttc agatgggggg    4980
atcatgtcta cctgcgggc gatgaagaaa acggtttccg gggtagggga gatcagctgg    5040
gaagaaagca ggttcctgag cagctgcgac ttaccgcagc cggtgggccc gtaaatcaca    5100
cctattaccg ggtgcaactg gtagttaaga gagctcagc tgccgtcatc cctgagcagg    5160
ggggccactt cgttaagcat gtccctgact cgcatgtttt cctgaccaa atccgccaga    5220 aggcgctcgc cgcccagcga tagcagttct tgcaaggaag caagttttt caacggtttg    5280 agaccgtccg ccgtaggcat gcttttgagc gtttgaccaa gcagttccag gcggtcccac    5340
agctcggtca cctgctctac ggcatctcga tccagcatat ctcctcgttt cgcgggttgg    5400
ggcggctttc gctgtacggc agtagtcggt gctcgtccag acgggccagg gtcatgtctt    5460
```

-continued

```
tccacgggcg cagggtcctc gtcagcgtag tctgggtcac ggtgaagggg tgcgctccgg    5520
gctgcgcgct ggccagggtg cgcttgaggc tggtcctgct ggtgctgaag cgctgccggt    5580
cttcgccctg cgcgtcggcc aggtagcatt tgaccatggt gtcatagtcc agcccctccg    5640
cggcgtggcc cttggcgcgc agcttgccct tggaggaggc cgcacgagg gggcagtgca     5700 gacttttgag ggcgtagagc ttgggcgcga gaaataccga ttccggggag taggcatccg    5760
cgccgcaggc cccgcagacg gtctcgcatt ccacgagcca ggtgagctct ggccgttcgg    5820
ggtcaaaaac caggtttccc ccatgctttt tgatgcgttt cttacctctg gtttccatga    5880
gccggtgtcc acgctcggtg acgaaaaggc tgtccgtgtc cccgtataca acttgagag     5940 gcctgtcctc gagcggtgtt ccgcggtcct cctcgtatag aaactcggac cactctgaga    6000
caaaggctcg cgtccaggcc agcacgaagg aggctaagtg ggaggggtag cggtcgttgt    6060
ccactagggg gtccactcgc tccagggtgt gaagacacat gtcgccctct cggcatcaa     6120 ggaaggtgat tggtttgtag gtgtaggcca cgtgaccggg tgttcctgaa gggggctat     6180 aaaaggggt gggggcgcgt tcgtcctcac tctcttccgc atcgctgtct gcgagggcca    6240
gctgttgggg tgagtactcc ctctgaaaag cgggcatgac ttctgcgcta agattgtcag    6300
tttccaaaaa cgaggaggat ttgatattca cctggcccgc ggtgatgcct ttgagggtgg    6360
ccgcatccat ctggtcagaa aagacaatct ttttgttgtc aagcttggtg gcaaacgacc    6420
cgtagagggc gttggacagc aacttggcga tggagcgcag ggtttggttt ttgtcgcgat    6480
cggcgcgctc cttggccgcg atgtttagct gcacgtattc gcgcgcaacg caccgccatt    6540
cgggaaagac ggtggtgcgc tcgtcgggca ccaggtgcac gcgccaaccg cggttgtgca    6600
gggtgacaag gtcaacgctg gtggctacct ctccgcgtag gcgctcgttg gtccagcaga    6660
ggcggccgcc cttgcgcgag cagaatggcg gtaggggtc tagctgcgtc tcgtccgggg    6720
ggtctgcgtc cacggtaaag accccgggca gcaggcgcgc gtcgaagtag tctatcttgc    6780
atccttgcaa gtctagcgcc tgctgccatg cgcgggcggc aagcgcgcgc tcgtatgggt    6840
tgagtggggg accccatggc atgggtggg tgagcgcgga ggcgtacatg ccgcaaatgt     6900
cgtaaacgta gaggggctct ctgagtattc caagatatgt agggtagcat cttccaccgc    6960
ggatgctggc gcgcacgtaa tcgtatagtt cgtgcgaggg agcgaggagg tcgggaccga    7020
ggttgctacg ggcgggctgc tctgctcgga agactatctg cctgaagatg gcatgtgagt    7080
tggatgatat ggttggacgc tggaagacgt tgaagctggc gtctgtgaga cctaccgcgt    7140
cacgcacgaa ggaggcgtag gagtcgcgca gcttgttgac cagctcggcg gtgacctgca    7200
cgtctagggc gcagtagtcc agggtttcct tgatgatgtc atacttatcc tgtcccttt     7260 ttttccacag ctcgcggttg aggacaaact cttcgcggtt tttccagtac tcttggatcg    7320
gaaacccgtc ggcctccgaa cggtaagagc ctagcatgta gaactggttg acggcctggt    7380
aggcgcagca tccttttct acgggtagcg cgtatgcctg cgcggccttc cggagcgagg    7440
tgtgggtgag cgcaaaggtg tccctgacca tgactttgag gtactggtat tgaagtcag     7500 tgtcgtcgca tccgccctgc tcccagagca aaaagtccgt gcgcttttg gaacgcggat     7560 ttggcagggc gaaggtgaca tcgttgaaga gtatctttcc cgcgcgaggc ataaagttgc    7620
gtgtgatgcg gaagggtccc ggcacctcgg aacggttgtt aattacctgg gcggcgagca    7680
cgatctcgtc aaagccgttg atgttgtggc ccacaatgta aagttccaag aagcgcggga    7740
tgcccttgat ggaaggcaat ttttttaagtt cctcgtaggt gagctcttca ggggagctga    7800
gcccgtgctc tgaaagggcc cagtctgcaa gatgagggtt ggaagcgacg aatgagctcc    7860
```

```
acaggtcacg ggccattagc atttgcaggt ggtcgcgaaa ggtcctaaac tggcgaccta    7920
tggccatttt ttctggggtg atgcagtaga aggtaagcgg gtcttgttcc cagcggtccc    7980
atccaaggtt cgcggctagg tctcgcgcgg cagtcactag aggctcatct ccgccgaact    8040
tcatgaccag catgaagggc acgagctgct tcccaaaggc ccccatccaa gtataggtct    8100
ctacatcgta ggtgacaaag agacgctcgg tgcgaggatg cgagccgatc gggaagaact    8160
ggatctcccg ccaccaattg gaggagtggc tattgatgtg gtgaaagtag aagtccctgc    8220
gacgggccga acactcgtgc tggcttttgt aaaaacgtgc gcagtactgg cagcggtgca    8280
cgggctgtac atcctgcacg aggttgacct gacgaccgcg cacaaggaag cagagtggga    8340
atttgagccc ctcgcctggc gggtttggct ggtggtcttc tacttcggct gcttgtcctt    8400
gaccgtctgg ctgctcgagg ggagttacgg tggatcggac caccacgccg cgcgagccca    8460
aagtccagat gtccgcgcgc ggcggtcgga gcttgatgac aacatcgcgc agatgggagc    8520
tgtccatggt ctggagctcc cgcggcgtca ggtcaggcgg gagctcctgc aggtttacct    8580
cgcatagacg ggtcagggcg cgggctagat ccaggtgata cctaatttcc aggggctggt    8640
tggtggcggc gtcgatggct tgcaagaggc cgcatccccg cggcgcgact acggtaccgc    8700
gcggcgggcg gtgggccgcg ggggtgtcct tggatgatgc atctaaaagc ggtgacgcgg    8760
gcgagccccc ggaggtaggg ggggctccgg acccgccggg agaggggggca ggggcacgtc    8820
ggcgccgcgc gcgggcagga gctggtgctg cgcgcgtagg ttgctggcga acgcgacgac    8880
gcggcggttg atctcctgaa tctggcgcct ctgcgtgaag acgacgggcc cggtgagctt    8940
gagcctgaaa gagagttcga cagaatcaat ttcggtgtcg ttgacggcgg cctggcgcaa    9000
aatctcctgc acgtctcctg agttgtcttg ataggcgatc tcggccatga actgctcgat    9060
ctcttcctcc tggagatctc cgcgtccggc tcgctccacg gtggcggcga ggtcgttgga    9120
aatgcgggcc atgagctgcg agaaggcgtt gaggcctccc tcgttccaga cgcggctgta    9180
gaccacgccc ccttcggcat cgcgggcgcg catgaccacc tgcgcgagat tgagctccac    9240
gtgccgggcg aagacggcgt agtttcgcag gcgctgaaag aggtagttga gggtggtggc    9300
ggtgtgttct gccacgaaga agtacataac ccagcgtcgc aacgtggatt cgttgatatc    9360
ccccaaggcc tcaaggcgct ccatggcctc gtagaagtcc acggcgaagt tgaaaaactg    9420
ggagttgcgc gccgacacgg ttaactcctc ctccagaaga cggatgagct cggcgacagt    9480
gtcgcgcacc tcgcgctcaa aggctacagg ggcctcttct tcttcttcaa tctcctcttc    9540
cataagggcc tccccttctt cttcttctgg cggcggtggg ggagggggga cacggcggcg    9600
acgacgcgc accgggaggc ggtcgacaaa gcgctcgatc atctccccgc ggcgacggcg    9660
catggtctcg gtgacggcgc ggccgttctc gcggggcgc agttggaaga cgccgcccgt    9720
catgtcccgg ttatgggttg gcgggggggct gccatgcggc agggatacgg cgctaacgat    9780
gcatctcaac aattgttgtg taggtactcc gccgccgagg gacctgagcg agtccgcatc    9840
gaccggatcg gaaaacctct cgagaaaggc gtctaaccag tcacagtcgc aaggtaggct    9900
gagcaccgtg gcgggcggca gcgggcggcg gtcggggttg tttctggcgg aggtgctgct    9960
gatgatgtaa ttaaagtagg cggtcttgag acggcggatg gtcgacagaa gcaccatgtc   10020
cttgggtccg gcctgctgaa tgcgcaggcg gtcgccatg cccaggctt cgttttgaca   10080
tcggcgcagg tctttgtagt agtcttgcat gagcctttct accggcactt cttcttctcc   10140
ttcctcttgt cctgcatctc ttgcatctat cgctgcggcg gcggcggagt ttggccgtag   10200
```

```
gtggcgccct cttcctccca tgcgtgtgac cccgaagccc ctcatcggct gaagcagggc    10260
taggtcggcg acaacgcgct cggctaatat ggcctgctgc acctgcgtga gggtagactg    10320
gaagtcatcc atgtccacaa agcggtggta tgcgcccgtg ttgatggtgt aagtgcagtt    10380
ggccataacg gaccagttaa cggtctggtg acccggctgc gagagctcgg tgtacctgag    10440
acgcgagtaa gccctcgagt caaatacgta gtcgttgcaa gtccgcacca ggtactggta    10500
tcccaccaaa aagtgcggcg gcggctgcg gtagaggggc cagcgtaggg tggccggggc     10560
tccgggggcg agatcttcca acataaggcg atgatatccg tagatgtacc tggacatcca    10620
ggtgatgccg gcggcggtgg tggaggcgcg cggaaagtcg cggacgcggt tccagatgtt    10680
gcgcagcggc aaaaagtgct ccatggtcgg gacgctctgg ccggtcaggc gcgcgcaatc    10740
gttgacgctc taccgtgcaa aaggagagcc tgtaagcggg cactcttccg tggtctggtg    10800
gataaattcg caagggtatc atggcggacg accgggttc gagccccgta tccggccgtc      10860
cgccgtgatc catgcggtta ccgcccgcgt gtcgaaccca ggtgtgcgac gtcagacaac    10920
gggggagtgc tccttttggc ttccttccag gcgcggcggc tgctgcgcta gcttttttgg    10980
ccactggccg cgcgcagcgt aagcggttag gctggaaagc gaaagcatta agtggctcgc    11040
tccctgtagc cggagggtta ttttccaagg gttgagtcgc gggacccccg gttcgagtct    11100
cggaccggcc ggactgcggc gaacgggggt ttgcctcccc gtcatgcaag ccccgcttg     11160 caaattcctc cggaaacagg gacgagcccc tttttgctt ttcccagatg catccggtgc     11220
tgcggcagat gcgccccct cctcagcagc ggcaagagca agagcagcgg cagacatgca     11280
gggcaccctc ccctcctcct accgcgtcag gaggggcgac atccgcggtt gacgcggcag    11340
cagatggtga ttacgaaccc ccgcggcgcc gggcccggca ctacctggac ttggaggagg    11400
gcgagggcct ggcgcggcta ggagcgccct ctcctgagcg gtacccaagg gtgcagctga    11460
agcgtgatac gcgtgaggcg tacgtgccgc ggcagaacct gtttcgcgac cgcgagggag    11520
aggagcccga ggagatgcgg gatcgaaagt tccacgcagg gcgcgagctg cggcatggcc    11580
tgaatcgcga gcggttgctg cgcgaggagg actttgagcc cgacgcgcga accgggatta    11640
gtcccgcgcg cgcacacgtg gcggccgccg acctggtaac cgcatacgag cagacggtga    11700
accaggagat taactttcaa aaaagcttta acaaccacgt gcgtacgctt gtggcgcgcg    11760
aggaggtggc tataggactg atgcatctgt gggactttgt aagcgcgctg gagcaaaacc    11820
caaatagcaa gccgctcatg gcgcagctgt tccttatagt gcagcacagc agggacaacg    11880
aggcattcag ggatgcgctg ctaaacatag tagagcccga gggccgctgg ctgctcgatt    11940
tgataaacat cctgcagagc atagtggtgc aggagcgcag cttgagcctg gctgacaagg    12000
tggccgccat caactattcc atgcttagcc tgggcaagtt ttacgcccgc aagatatacc    12060
atacccctta cgttcccata gacaaggagg taaagatcga ggggttctac atgcgcatgg    12120
cgctgaaggt gcttaccttg agcgacgacc tgggcgttta tcgcaacgag cgcatccaca    12180
aggccgtgag cgtgagccgg cggcgcgagc tcagcgaccg cgagctgatg cacagcctgc    12240
aaagggccct ggctggcacg ggcagcgcg atagagaggc cgagtcctac tttgacgcgg    12300
gcgctgacct gcgctgggcc ccaagccgac gcgccctgga ggcagctggg gccggacctg    12360
ggctggcggt ggcacccgcg cgcgctgca acgtcggcgg cgtggaggaa tatgacgagg    12420
acgatgagta cgagccagag gacggcgagt actaagcggt gatgtttctg atcagatgat    12480
gcaagacgca acggacccgg cggtgcgggc ggcgctgcag agccagccgt ccggccttaa    12540
ctccacggac gactggcgcc aggtcatgga ccgcatcatg tcgctgactg cgcgcaatcc    12600
```

```
tgacgcgttc cggcagcagc cgcaggccaa ccggctctcc gcaattctgg aagcggtggt    12660
cccggcgcgc gcaaaccccca cgcacgagaa ggtgctggcg atcgtaaacg cgctggccga    12720
aaacagggcc atccggcccg acgaggcggg cctggtctac gacgcgctgc ttcagcgcgt    12780
ggctcgttac aacagcggca acgtgcagac caacctggac cggctggtgg gggatgtgcg    12840
cgaggccgtg gcgcagcgtg agcgcgcgca gcagcagggc aacctgggct ccatggttgc    12900
actaaacgcc ttcctgagta cacagcccgc caacgtgccg cggggacagg aggactacac    12960
caactttgtg agcgcactgc ggctaatggt gactgagaca ccgcaaagtg aggtgtacca    13020
gtctgggcca gactattttt tccagaccag tagacaaggc ctgcagaccg taaacctgag    13080
ccaggctttc aaaaacttgc aggggctgtg ggggtgcgg gctcccacag gcgaccgcgc    13140
gaccgtgtct agcttgctga cgcccaactc gcgcctgttg ctgctgctaa tagcgccctt    13200
cacggacagt ggcagcgtgt cccgggacac atacctaggt cacttgctga cactgtaccg    13260
cgaggccata ggtcaggcgc atgtggacga gcatactttc caggagatta caagtgtcag    13320
ccgcgcgctg gggcaggagg acacgggcag cctggaggca accctaaaact acctgctgac    13380 caaccggcgg cagaagatcc cctcgttgca cagtttaaac agcgaggagg agcgcatttt    13440
gcgctacgtg cagcagagcg tgagccttaa cctgatgcgc gacggggtaa cgcccagcgt    13500
ggcgctggac atgaccgcgc gcaacatgga accgggcatg tatgcctcaa accggccgtt    13560
tatcaaccgc ctaatggact acttgcatcg cgcggccgcc gtgaacccccg agtatttcac    13620 caatgccatc ttgaacccgc actggctacc gccccctggt ttctacaccg ggggattcga    13680
ggtgcccgag ggtaacgatg gattcctctg gacgacata acgacagcg tgtttttcccc    13740 gcaaccgcag accctgctag agttgcaaca gcgcgagcag gcagaggcgg cgctgcgaaa    13800
ggaaagcttc cgcaggccaa gcagcttgtc cgatctaggc gctgcggccc cgcggtcaga    13860
tgctagtagc ccatttccaa gcttgatagg gtctcttacc agcactcgca ccacccgccc    13920
gcgcctgctg ggcgaggagg agtacctaaa caactcgctg ctgcagccgc agcgcgaaaa    13980
aaacctgcct ccggcatttc ccaacaacgg gatagagagc ctagtggaca agatgagtag    14040
atggaagacg tacgcgcagg agcacaggga cgtgccaggc ccgcgcccgc ccacccgtcg    14100
tcaaaggcac gaccgtcagc ggggtctggt gtgggaggac gatgactcgg cagacgacag    14160
cagcgtcctg gatttgggag ggagtggcaa cccgtttgcg caccttcgcc ccaggctggg    14220
gagaatgttt taaaaaaaaa aaagcatgat gcaaaataaa aaactcacca aggccatggc    14280
accgagcgtt ggttttcttg tattccccctt agtatgcggc gcgcggcgat gtatgaggaa    14340
ggtcctcctc cctcctacga gagtgtggtg agcgcggcgc cagtggcggc ggcgctgggt    14400
tctcccttcg atgctcccct ggacccgccg tttgtgcctc cgcggtacct gcggcctacc    14460 gggggagaa acagcatccg ttactctgag ttggcacccc tattcgacac cacccgtgtg    14520
tacctggtgg acaacaagtc aacggatgtg gcatccctga actaccagaa cgaccacagc    14580
aactttctga ccacggtcat tcaaaacaat gactacagcc gggggaggc aagcacacag    14640 accatcaatc ttgacgaccg gtcgcactgg ggcggcgacc tgaaaaccat cctgcatacc    14700
aacatgccaa atgtgaacga gttcatgttt accaataagt ttaaggcgcg ggtgatggtg    14760
tcgcgcttgc ctactaagga caatcaggtg gagctgaaat acgagtgggt ggagttcacg    14820
ctgcccgagg gcaactactc cgagaccatg accatagacc ttatgaacaa cgcgatcgtg    14880
gagcactact tgaaagtggg cagacagaac gggttctgg aaaagcgacat cggggtaaag    14940
```

```
tttgacaccc gcaacttcag actggggttt gacccgtca ctggtcttgt catgcctggg    15000
gtatatacaa acgaagcctt ccatccagac atcattttgc tgccaggatg cggggtggac    15060
ttcacccaca gccgcctgag caacttgttg ggcatccgca agcggcaacc cttccaggag    15120
ggctttagga tcacctacga tgatctggag ggtggtaaca ttcccgcact gttggatgtg    15180
gacgcctacc aggcgagctt gaaagatgac accgaacagg cgggggtgg cgcaggcggc    15240
agcaacagca gtggcagcgg cgcggaagag aactccaacg cggcagccgc ggcaatgcag    15300
ccggtggagg acatgaacga tcatgccatt cgcggcgaca cctttgccac acgggctgag    15360
gagaagcgcg ctgaggccga agcagcggcc gaagctgccg ccccgctgc gcaacccgag    15420
gtcgagaagc tcagaagaa accggtgatc aaacccctga cagaggacag caagaaacgc    15480
agttacaacc taataagcaa tgacagcacc ttcacccagt accgcagctg gtaccttgca    15540
tacaactacg gcgaccctca gaccggaatc cgctcatgga ccctgctttg cactcctgac    15600
gtaacctgcg gctcggagca ggtctactgg tcgttgccag acatgatgca agaccccgtg    15660
accttccgct ccacgcgcca gatcagcaac tttccggtgg tgggcgccga gctgttgccc    15720
gtgcactcca agagcttcta caacgaccag gccgtctact cccaactcat ccgccagttt    15780
acctctctga cccacgtgtt caatcgcttt cccgagaacc agattttggc gcgcccgcca    15840
gccccccacca tcaccaccgt cagtgaaaac gttcctgctc tcacagatca cgggacgcta    15900
ccgctgcgca acagcatcgg aggagtccag cgagtgacca ttactgacgc cagacgccgc    15960
acctgccccct acgtttacaa ggccctgggc atagtctcgc cgcgcgtcct atcgagccgc    16020
acttttttgag caagcatgtc catccttata tcgcccagca ataacacagg ctggggcctg    16080
cgcttcccaa gcaagatgtt tggcggggcc aagaagcgct ccgaccaaca cccagtgcgc    16140
gtgcgcgggc actaccgcgc gccctgggc gcgcacaaac gcggccgcac tgggcgcacc    16200
accgtcgatg acgccatcga cgcggtggtg gaggaggcgc gcaactacac gcccacgccg    16260
ccaccagtgt ccacagtgga cgcggccatt cagaccgtgg tgcgcggagc ccggcgctat    16320
gctaaaatga agagacggcg gaggcgcgta gcacgtcgcc accgccgccg acccggcact    16380
gccgcccaac gcgcggcggc ggccctgctt aaccgcgcac gtcgcaccgg ccgacgggcg    16440
gccatgcggg ccgctcgaag gctggccgcg ggtattgtca ctgtgccccc caggtccagg    16500
cgacgagcgg ccgccgcagc agccgcggcc attagtgcta tgactcaggg tcgcagggc    16560
aacgtgtatt gggtgcgcga ctcggttagc ggcctgcgcg tgcccgtgcg cacccgcccc    16620
ccgcgcaact agattgcaag aaaaaactac ttagactcgt actgttgtat gtatccagcg    16680
gcggcggcgc gcaacgaagc tatgtccaag cgcaaaatca agaagagat gctccaggtc    16740
atcgcgccgg agatctatgg cccccgaag aaggaagagc aggattacaa gccccgaaag    16800
ctaaagcggg tcaaaagaa aagaaagat gatgatgatg aacttgacga cgaggtggaa    16860
ctgctgcacg ctaccgcgcc caggcgacgg gtacagtgga aggtcgacg cgtaaaacgt    16920
gttttgcgac ccggcaccac cgtagtcttt acgcccggtg agcgctccac ccgcacctac    16980
aagcgcgtgt atgatgaggt gtacggcgac gaggacctgc ttgagcaggc caacgagcgc    17040
ctcgggagt ttgcctacgg aaagcggcat aaggacatgc tggcgttgcc gctggacgag    17100
ggcaacccaa cacctagcct aaagcccgta acactgcagc aggtgctgcc cgcgcttgca    17160
ccgtccgaag aaaagcgcgg cctaaagcgc gagtctggtg acttggcacc caccgtgcag    17220
ctgatggtac caagcgcca gcgactggaa gatgtcttgg aaaaaatgac cgtgaacct    17280
gggctggagc ccgaggtccg cgtgcggcca atcaagcagg tggcgccggg actgggcgtg    17340
```

```
cagaccgtgg acgttcagat acccactacc agtagcacca gtattgccac cgccacagag   17400
ggcatggaga cacaaacgtc cccggttgcc tcagcggtgg cggatgccgc ggtgcaggcg   17460
gtcgctgcgg ccgcgtccaa gacctctacg gaggtgcaaa cggacccgtg gatgtttcgc   17520
gtttcagccc cccggcgccc gcgcggttcg aggaagtacg gcgccgccag cgcgctactg   17580
cccgaatatg ccctacatcc ttccattgcg cctaccccg gctatcgtgg ctacacctac    17640
cgccccagaa gacgagcaac tacccgacgc cgaaccacca ctggaacccg ccgccgccgt   17700
cgccgtcgcc agcccgtgct ggccccgatt tccgtgcgca gggtggctcg cgaaggaggc   17760
aggaccctgg tgctgccaac agcgcgctac cacccagca tcgtttaaaa gccggtcttt    17820
gtggttcttg cagatatggc cctcacctgc cgcctccgtt tcccggtgcc gggattccga   17880
ggaagaatgc accgtaggag gggcatggcc ggccacggcc tgacgggcgg catgcgtcgt   17940
gcgcaccacc ggcggcggcg cgcgtcgcac cgtcgcatgc gcggcggtat cctgcccctc   18000
cttattccac tgatcgccgc ggcgattggc gccgtgcccg gaattgcatc cgtggccttg   18060
caggcgcaga gacactgatt aaaaacaagt tgcatgtgga aaaatcaaaa taaaaagtct   18120
ggactctcac gctcgcttgg tcctgtaact attttgtaga atggaagaca tcaactttgc   18180
gtctctggcc ccgcgacacg gctcgcgccc gttcatggga aactggcaag atatcggcac   18240
cagcaatatg agcggtggcg ccttcagctg gggctcgctg tggagcggca ttaaaaattt   18300
cggttccacc gttaagaact atggcagcaa ggcctggaac agcagcacag gccagatgct   18360
gagggataag ttgaaagagc aaaatttcca acaaaaggtg gtagatggcc tggcctctgg   18420
cattagcggg gtggtggacc tggccaacca ggcagtgcaa aataagatta acagtaagct   18480
tgatccccgc cctcccgtag aggagcctcc accggccgtg gagacagtgt ctccagaggg   18540
gcgtggcgaa aagcgtccgc gccccgacag ggaagaaact ctggtgacgc aaatagacga   18600
gcctccctcg tacgaggagg cactaaagca aggcctgccc accacccgtc ccatcgcgcc   18660
catggctacc ggagtgctgg gccagcacac accggtaacg ctggacctgc ctcccccgc   18720 cgacacccag cagaaacctg tgctgccagg cccgaccgcc gttgttgtaa cccgtcctag   18780
ccgcgcgtcc ctgcgccgcg ccgccagcgg tccgcgatcg ttgcggcccg tagccagtgg   18840
caactggcaa agcacactga acagcatcgt gggtctgggg gtgcaatccc tgaagcgccg   18900
acgatgcttc tgaatagcta acgtgtcgta tgtgtgtcat gtatgcgtcc atgtcgccgc   18960
cagaggagct gctgagccgc cgcgcgcccg ctttccaaga tggctacccc ttcgatgatg   19020
ccgcagtggt cttacatgca catctcgggc caggacgcct cggagtacct gagccccggg   19080
ctggtgcagt ttgcccgcgc caccgagacg tacttcagcc tgaataacaa gtttagaaac   19140
cccacggtgg cgcctacgca cgacgtgacc acagaccggt cccagcgttt gacgctgcgg   19200
ttcatccctg tggaccgtga ggatactgcg tactcgtaca aggcgcggtt caccctagct   19260
gtgggtgata accgtgtgct ggacatggct tccacgtact ttgacatccg cggcgtgctg   19320
gacaggggcc ctactttaa gccctactct ggcactgcct acaacgccct ggctcccaag   19380
ggtgccccaa atccttgcga atgggatgaa gctgctactg ctcttgaaat aaacctagaa   19440
gaagaggacg atgacaacga agacgaagta gacgagcaag ctgagcagca aaaaactcac   19500
gtatttgggc aggcgcctta ttctggtata aatattacaa aggagggtat tcaaataggt   19560
gtcgaaggtc aaacacctaa atatgccgat aaaacatttc aacctgaacc tcaaatagga   19620
gaatctcagt ggtacgaaac tgaaattaat catgcagctg ggagagtcct taaaaagact   19680
```

-continued

```
accccaatga aaccatgtta cggttcatat gcaaaaccca caaatgaaaa tggagggcaa    19740
ggcattcttg taaagcaaca aaatggaaag ctagaaagtc aagtggaaat gcaattttc     19800
tcaactactg aggcgaccgc aggcaatggt gataacttga ctcctaaagt ggtattgtac    19860
agtgaagatg tagatataga aaccccagac actcatattt cttacatgcc cactattaag    19920
gaaggtaact cacgagaact aatgggccaa caatctatgc ccaacaggcc taattacatt    19980
gcttttaggg acaattttat tggtctaatg tattacaaca gcacgggtaa tatgggtgtt    20040
ctggcgggcc aagcatcgca gttgaatgct gttgtagatt tgcaagacag aaacacagag    20100
ctttcatacc agcttttgct tgattccatt ggtgatagaa ccaggtactt ttctatgtgg    20160
aatcaggctg ttgacagcta tgatccagat gttagaatta ttgaaaatca tggaactgaa    20220
gatgaacttc caaattactg ctttccactg ggaggtgtga ttaatacaga gactcttacc    20280
aaggtaaaac ctaaaacagg tcaggaaaat ggatgggaaa agatgctac agaattttca     20340
gataaaaatg aaataagagt tggaaataat tttgccatgg aaatcaatct aaatgccaac    20400
ctgtggagaa atttcctgta ctccaacata gcgctgtatt tgcccgacaa gctaaagtac    20460
agtccttcca acgtaaaaat ttctgataac ccaaacacct acgactacat gaacaagcga    20520
gtggtggctc ccgggttagt ggactgctac attaaccttg gagcacgctg gtcccttgac    20580
tatatggaca acgtcaaccc atttaaccac caccgcaatg ctggcctgcg ctaccgctca    20640
atgttgctgg gcaatggtcg ctatgtgccc ttccacatcc aggtgcctca gaagttcttt    20700
gccattaaaa acctccttct cctgccgggc tcatacacct acgagtggaa cttcaggaag    20760
gatgttaaca tggttctgca gagctcccta ggaaatgacc taagggttga cggagccagc    20820
attaagtttg atagcatttg cctttacgcc accttcttcc ccatggccca caacaccgcc    20880
tccacgcttg aggccatgct tagaaacgac accaacgacc agtcctttaa cgactatctc    20940
tccgccgcca acatgctcta ccctatatccc gccaacgcta ccaacgtgcc catatccatc    21000
ccctcccgca actgggcggc tttccgcggc tgggccttca cgcgccttaa gactaaggaa    21060
accccatcac tgggctcggg ctacgaccct tattacaccct actctggctc tatccctac    21120
ctagatggaa ccttttacct caaccacacc tttaagaagg tggccattac ctttgactct    21180
tctgtcagct ggcctggcaa tgaccgcctg cttaccccca acgagtttga aattaagcgc    21240
tcagttgacg gggagggtta caacgttgcc cagtgtaaca tgaccaaaga ctggttcctg    21300
gtacaaatgc tagctaacta caacattggc taccagggct tctatatccc agagagctac    21360
aaggaccgca tgtactcctt cttagaaac ttccagccca tgagccgtca ggtggtggat    21420
gatactaaat acaaggacta ccaacaggtg ggcatcctac accaacacaa caactctgga    21480
tttgttggct accttgcccc caccatgcgc gaaggacagg cctaccctgc taacttcccc    21540
tatccgctta taggcaagac cgcagttgac agcattaccc agaaaaagtt tctttgcgat    21600
cgcacccttt ggcgcatccc attctccagt aactttatgt ccatgggcgc actcacagac    21660
ctgggccaaa accttctcta cgccaactcc gcccacgcgc tagacatgac ttttgaggtg    21720
gatcccatgg acgagcccac ccttctttat gttttgtttg aagtctttga cgtggtccgt    21780
gtgcaccggc cgcaccgcgg cgtcatcgaa accgtgtacc tgcgcacgcc cttctcggcc    21840
ggcaacgcca caacataaag aagcaagcaa catcaacaac agctgccgcc atgggctcca    21900
gtgagcagga actgaaagcc attgtcaaag atcttggttg tgggccatat ttttgggca     21960
cctatgacaa gcgcttttcca ggcttttgttt ctccacacaa gctcgcctgc gccatagtca    22020
atacggccgg tcgcgagact gggggcgtac actggatggc cttttgcctgg aacccgcact    22080
```

```
caaaaacatg ctacctcttt gagcccttg gcttttctga ccagcgactc aagcaggttt    22140
accagtttga gtacgagtca ctcctgcgcc gtagcgccat tgcttcttcc cccgaccgct    22200
gtataacgct ggaaaagtcc acccaaagcg tacaggggcc caactcggcc gcctgtggac    22260
tattctgctg catgtttctc cacgcctttg ccaactggcc ccaaactccc atggatcaca    22320
accccaccat gaaccttatt accggggtac ccaactccat gctcaacagt ccccaggtac    22380
agcccaccct gcgtcgcaac caggaacagc tctacagctt cctggagcgc cactcgccct    22440
acttccgcag ccacagtgcg cagattagga gcgccacttc tttttgtcac ttgaaaaaca    22500
tgtaaaaata atgtactaga gacactttca ataaaggcaa atgcttttat ttgtacactc    22560
tcgggtgatt atttaccccc acccttgccg tctgcgccgt ttaaaaatca aggggttct     22620
gccgcgcatc gctatgcgcc actggcaggg acacgttgcg atactggtgt ttagtgctcc    22680
acttaaactc aggcacaacc atccgcggca gctcggtgaa gttttcactc cacaggctgc    22740
gcaccatcac caacgcgttt agcaggtcgg gcgccgatat cttgaagtcg cagttgggc     22800
ctccgcctg cgcgcgcgag ttgcgataca cagggttgca gcactggaac actatcagcg     22860
ccgggtggtg cacgctggcc agcacgctct tgtcggagat cagatccgcg tccaggtcct    22920
ccgcgttgct cagggcgaac ggagtcaact ttggtagctg ccttcccaaa aagggcgcgt    22980
gcccaggctt tgagttgcac tcgcaccgta gtggcatcaa aaggtgaccg tgcccggtct    23040
gggcgttagg atacagcgcc tgcataaaag ccttgatctg cttaaaagcc acctgagcct    23100
ttgcgccttc agagaagaac atgccgcaag acttgccgga aaactgattg gccggacagg    23160
ccgcgtcgtg cacgcagcac cttgcgtcgg tgttggagat ctgcaccaca tttcggcccc    23220
accggttctt cacgatcttg gccttgctag actgctcctt cagcgcgcgc tgcccgtttt    23280
cgctcgtcac atccatttca atcacgtgct ccttatttat cataatgctt ccgtgtagac    23340
acttaagctc gccttcgatc tcagcgcagc ggtgcagcca caacgcgcag cccgtgggct    23400
cgtgatgctt gtaggtcacc tctgcaaacg actgcaggta cgcctgcagg aatcgcccca    23460
tcatcgtcac aaaggtcttg ttgctggtga aggtcagctg caacccgcgg tgctcctcgt    23520
tcagccaggt cttgcatacg gccgccagag cttccacttg gtcaggcagt agtttgaagt    23580
tcgcctttag atcgttatcc acgtggtact tgtccatcag cgcgcgcgca gcctccatgc    23640
ccttctccca cgcagacacg atcggcacac tcagcgggtt catcaccgta atttcacttt    23700
ccgcttcgct gggctcttcc tcttcctctt gcgtccgcat accacgcgcc actgggtcgt    23760
cttcattcag ccgccgcact gtgcgcttac ctccttgcc atgcttgatt agcaccggtg     23820
ggttgctgaa acccaccatt tgtagcgcca catcttctct ttcttcctcg ctgtccacga    23880
ttacctctgg tgatggcggg cgctcgggct tgggagaagg gcgcttcttt ttcttcttgg    23940
gcgcaatggc caaatccgcc gccgaggtcg atggccgcgg gctgggtgtg cgcggcacca    24000
gcgcgtcttg tgatgagtct tcctcgtcct cggactcgat acgccgcctc atccgctttt    24060
ttggggggcgc ccggggaggc ggcggcgacg gggacgggga cgacgtcc tccatggttg      24120
ggggacgtcg cgccgcaccg cgtccgcgct cggggtggt ttcgcgctgc tcctcttccc     24180
gactggccat ttccttctcc tataggcaga aaaagatcat ggagtcagtc gagaagaagg    24240
acagcctaac cgcccctct gagttcgcca ccaccgcctc caccgatgcc gccaacgcgc     24300
ctaccacctt ccccgtcgag gcaccccgc ttgaggagga ggaagtgatt atcgagcagg     24360
acccaggttt tgtaagcgaa gacgacgagg accgctcagt accaacagag gataaaaagc    24420
```

```
aagaccagga caacgcagag gcaaacgagg aacaagtcgg gcgggggggac gaaaggcatg    24480 gcgactacct agatgtggga gacgacgtgc tgttgaagca tctgcagcgc cagtgcgcca    24540
ttatctgcga cgcgttgcaa gagcgcagcg atgtgcccct cgccatagcg gatgtcagcc    24600
ttgcctacga acgccaccta ttctcaccgc gcgtaccccc caaacgccaa gaaaacggca    24660
catgcgagcc caacccgcgc ctcaacttct accccgtatt tgccgtgcca gaggtgcttg    24720
ccacctatca catctttttc caaaactgca agataccccc atcctgccgt gccaaccgca    24780
gccgagcgga caagcagctg gccttgcggc agggcgctgt catacctgat atcgcctcgc    24840
tcaacgaagt gccaaaaatc tttgagggtc ttggacgcga cgagaagcgc gcggcaaacg    24900
ctctgcaaca ggaaaacagc gaaaatgaaa gtcactctgg agtgttggtg gaactcgagg    24960
gtgacaacgc gcgcctagcc gtactaaaac gcagcatcga ggtcacccac tttgcctacc    25020
cggcacttaa cctaccccccc aaggtcatga gcacagtcat gagtgagctg atcgtgcgcc    25080
gtgcgcagcc cctggagagg gatgcaaatt tgcaagaaca aacagaggag ggcctacccg    25140
cagttggcga cgagcagcta gcgcgctggc ttcaaacgcg cgagcctgcc gacttggagg    25200
agcgacgcaa actaatgatg gccgcagtgc tcgttaccgt ggagcttgag tgcatgcagc    25260
ggttctttgc tgacccggag atgcagcgca agctagagga aacattgcac tacacctttc    25320
gacagggcta cgtacgccag gcctgcaaga tctccaacgt ggagctctgc aacctggtct    25380
cctaccttgg aattttgcac gaaaaccgcc ttgggcaaaa cgtgcttcat tccacgctca    25440
agggcgaggc gcgccgcgac tacgtccgcg actgcgttta cttatttcta tgctacacct    25500
ggcagacggc catgggcgtt tggcagcagt gcttggagga gtgcaacctc aaggagctgc    25560
agaaactgct aaagcaaaac ttgaaggacc tatggacggc cttcaacgag cgctccgtgg    25620
ccgcgcacct ggcggacatc attttccccg aacgcctgct taaaaccctg caacagggtc    25680
tgccagactt caccagtcaa agcatgttgc agaactttag gaactttatc ctagagcgct    25740
caggaatctt gcccgccacc tgctgtgcac ttcctagcga ctttgtgccc attaagtacc    25800
gcgaatgccc tccgccgctt tggggccact gctaccttct gcagctagcc aactaccttg    25860
cctaccactc tgacataatg gaagacgtga gcggtgacgg tctactggag tgtcactgtc    25920
gctgcaacct atgcacccccg caccgctccc tggtttgcaa ttcgcagctg cttaacgaaa    25980
gtcaaattat cggtaccttt gagctgcagg gtccctcgcc tgacgaaaag tccgcggctc    26040
cggggttgaa actcactccg gggctgtgga cgtcggctta ccttcgcaaa tttgtacctg    26100
aggactacca cgcccacgag attaggttct acgaagacca atcccgcccg ccaaatgcgg    26160
agcttaccgc ctgcgtcatt acccagggcc acattcttgg ccaattgcaa gccatcaaca    26220
aagcccgcca agagtttctg ctacgaaagg acgggggggt ttacttggac ccccagtccg    26280
gcgaggagct caacccaatc cccccgccgc cgcagcccta tcagcagcag ccgcgggccc    26340
ttgcttccca ggatggcacc caaaagaag ctgcagctgc cgccgccacc cacggacgag    26400
gaggaatact gggacagtca ggcagaggag gttttggacg aggaggagga ggacatgatg    26460
gaagactggg agagcctaga cgaggaagct tccgaggtcg aagaggtgtc agacgaaaca    26520
ccgtcaccct cggtcgcatt cccctcgccg gcgccccaga aatcggcaac cggttccagc    26580
atggctacaa cctccgctcc tcaggcgccg ccggcactgc ccgttcgccg acccaaccgt    26640
agatgggaca ccactggaac cagggccggt aagtccaagc agccgccgcc gttagcccaa    26700
gagcaacaac agcgccaagg ctaccgctca tggcgcgggc acaagaacgc catagttgct    26760
tgcttgcaag actgtggggg caacatctcc ttcgcccgcc gctttcttct ctaccatcac    26820
```

```
ggcgtggcct tccccgtaa catcctgcat tactaccgtc atctctacag cccatactgc   26880
accggcggca gcggcagcgg cagcaacagc agcggccaca cagaagcaaa ggcgaccgga   26940
tagcaagact ctgacaaagc ccaagaaatc cacagcggcg gcagcagcag gaggaggagc   27000
gctgcgtctg gcgcccaacg aacccgtatc gacccgcgag cttagaaaca ggattttttcc  27060 cactctgtat gctatatttc aacagagcag gggccaagaa caagagctga aaataaaaaa   27120
caggtctctg cgatccctca cccgcagctg cctgtatcac aaaagcgaag atcagcttcg   27180
gcgcacgctg gaagacgcgg aggctctctt cagtaaatac tgcgcgctga ctcttaagga   27240
ctagtttcgc gcccttttctc aaatttaagc gcgaaaacta cgtcatctcc agcggccaca  27300
cccggcgcca gcacctgtcg tcagcgccat tatgagcaag gaaattccca cgccctacat   27360
gtggagttac cagccacaaa tgggacttgc ggctggagct gcccaagact actcaacccg   27420
aataaactac atgagcgcgg accccacat gatatcccgg gtcaacgaa tccgcgccca    27480 ccgaaaccga attctcttgg aacaggcggc tattaccacc acacctcgta ataaccttaa   27540
tccccgtagt tggcccgctg ccctggtgta ccaggaaagt cccgctccca ccactgtggt   27600
acttcccaga gacgcccagg ccgaagttca gatgactaac tcaggggcgc agcttgcggg   27660
cggctttcgt cacagggtgc ggtcgcccgg gcagggtata actcacctga caatcagagg   27720
gcgaggtatt cagctcaacg acgagtcggt gagctcctcg cttggtctcc gtccggacgg   27780
gacatttcag atcggcggcg ccggccgtcc ttcattcacg cctcgtcagg caatcctaac   27840
tctgcagacc tcgtcctctg agccgcgctc tggaggcatt ggaactctgc aatttattga   27900
ggagtttgtg ccatcggtct actttaaccc cttctcggga cctcccggcc actatccgga   27960
tcaatttatt cctaactttg acgcggtaaa ggactcggcg gacggctacg actgaatgtt   28020
aagtggagag gcagagcaac tgcgcctgaa acacctggtc cactgtcgcc gccacaagtg   28080 cttttgcccgc gactccggtg agttttgcta ctttgaattg cccgaggatc atatcgaggg   28140
cccggcgcac ggcgtccggc ttaccgccca gggagagctt gcccgtagcc tgattcggga   28200
gtttacccag cgcccctgc tagttgagcg ggacagggga ccctgtgttc tcactgtgat   28260
ttgcaactgt cctaaccttg gattacatca agatcctcta gttataacta gagtacccgg   28320
ggatcttatt ccctttaact aataaaaaaa aataataaag catcacttac ttaaaatcag   28380
ttagcaaatt tctgtccagt ttattcagca gcacctcctt gccctcctcc cagctctggt   28440
attgcagctt cctcctggct gcaaactttc tccacaatct aaatggaatg tcagtttcct   28500
cctgttcctg tccatccgca cccactatct tcatgttgtt gcagatgaag cgcgcaagac   28560
cgtctgaaga taccttcaac cccgtgtatc catatgacac ggaaaccggt cctccaactg   28620
tgccttttct tactcctccc tttgtatccc ccaatgggtt tcaagagagt cccctgggg    28680 tactctcttt gcgcctatcc gaacctctag ttacctccaa tggcatgctt gcgctcaaaa   28740
tgggcaacgg cctctctctg gacgaggccg gcaaccttac ctcccaaaat gtaaccactg   28800
tgagcccacc tctcaaaaaa accaagtcaa acataaacct ggaaatatct gcacccctca   28860
cagttacctc agaagcccta actgtggctg ccgccgcacc tctaatggtc gcgggcaaca   28920
cactcaccat gcaatcacag gccccgctaa ccgtgcacga ctccaaactt agcattgcca   28980
cccaaggacc cctcacagtg tcagaaggaa agctagccct gcaaacatca ggccccctca   29040
ccaccaccga tagcagtacc cttactatca ctgcctcacc ccctctaact actgccactg   29100
gtagcttggg cattgacttg aaagagccca tttatacaca aaatggaaaa ctaggactaa   29160
```

```
agtacggggc tcctttgcat gtaacagacg acctaaacac tttgaccgta gcaactggtc   29220
caggtgtgac tattaataat acttccttgc aaactaaagt tactggagcc ttgggttttg   29280
attcacaagg caatatgcaa cttaatgtag caggaggact aaggattgat tctcaaaaca   29340
gacgccttat acttgatgtt agttatccgt ttgatgctca aaaccaacta aatctaagac   29400
taggacaggg ccctcttttt ataaactcag cccacaactt ggatattaac tacaacaaag   29460
gcctttactt gtttacagct tcaaacaatt ccaaaaagct tgaggttaac ctaagcactg   29520
ccaaggggtt gatgtttgac gctacagcca tagccattaa tgcaggagat gggcttgaat   29580
ttggttcacc taatgcacca aacacaaatc ccctcaaaac aaaaattggc catggcctag   29640
aatttgattc aaacaaggct atggttccta aactaggaac tggccttagt tttgacagca   29700
caggtgccat tacagtagga aacaaaaata atgataagct aactttgtgg accacaccag   29760
ctccatctcc taactgtaga ctaaatgcag agaaagatgc taaactcact ttggtcttaa   29820
caaaatgtgg cagtcaaata cttgctacag tttcagtttt ggctgttaaa ggcagtttgg   29880
ctccaatatc tggaacagtt caaagtgctc atcttattat aagatttgac gaaaatggag   29940
tgctactaaa caattccttc ctggacccag aatattggaa ctttagaaat ggagatctta   30000
ctgaaggcac agcctataca aacgctgttg gatttatgcc taacctatca gcttatccaa   30060
aatctcacgg taaaactgcc aaaagtaaca ttgtcagtca agtttactta aacgagacaa   30120
aaactaaacc tgtaacacta accattacac taaacggtac acaggaaaca ggagacacaa   30180
ctccaagtgc atactctatg tcatttttcat gggactggtc tggccacaac tacattaatg   30240
aaatatttgc cacatcctct tacacttttt catacattgc caagaataa agaatcgttt   30300 gtgttatgtt tcaacgtgtt tattttttcaa ttgcagaaaa tttcaagtca tttttcattc   30360
agtagtatag ccccaccacc acatagctta tacagatcac cgtaccttaa tcaaactcac   30420
agaaccctag tattcaacct gccacctccc tcccaacaca cagagtacac agtcctttct   30480
ccccggctgg ccttaaaaag catcatatca tgggtaacag acatattctt aggtgttata   30540
ttccacacgg tttcctgtcg agccaaacgc tcatcaagtg atattaataa actccccggg   30600
cagctcactt aagttcatgt cgctgtccag ctgctgagcc acaggctgct gtccaacttg   30660
cggttgctta acgggcggcg aaggagaagt ccacgcctac atggggggag agtcataatc   30720
gtgcatcagg atagggcggt ggtgctgcag cagcgcgcga taaactgct gccgccgccg   30780 ctccgtcctg caggaataca acatggcagt ggtctcctca gcgatgattc gcaccgcccg   30840
cagcataagg cgcttgtcct ccgggcacag cagcgcaccc tgatctcact taaatcagca   30900
cagtaactgc agcacagcac cacaatattg ttcaaaatcc cacagtgcaa ggcgctgtat   30960
ccaaagctca tggcggggac cacagaaccc acgtggccat cataccacaa gcgcaggtag   31020
attaagtggc gacccctcat aaacacgctg gacataaaca ttacctcttt tggcatgttg   31080
taattcacca cctcccggta ccatataaac ctctgattaa acatggcgcc atccaccacc   31140
atcctaaacc agctggccaa aacctgcccc gccgggntat acactgcagg gaaccgggac   31200
ttggacaatg acaagtggga gagcccagga ctcgtaacca tggatcatca tgctcgtcat   31260
gatatcaatg ttggcacaac acaggcacac gtgcatacac ttcctcagga ttacaagctc   31320
ctcccgcgtt agaaccatat cccagggaac aaccccattcc tgaatcagcg taaatcccac   31380
actgcaggga agacctcgca cgtaactcac gttgtgcatt gtcaaagtgt tacattcggg   31440
cagcagcgga tgatcctcca gtatggtagc gcgggtttct gtctcaaaag gaggtagacg   31500
atccctactg tacggagtgc gccgagacaa ccgagatcgt gttggtcgta gtgtcatgcc   31560
```

```
aaatggaacg ccggacgtag tcatatttcc tgaagcaaaa ccaggtgcgg gcgtgacaaa    31620
cagatctgcg tctccggtct cgccgcttag atcgctctgt gtagtagttg tagtatatcc    31680
actctctcaa agcatccagg cgcccctgg cttcgggttc tatgtaaact ccttcatgcg     31740
ccgctgccct gataacatcc accaccgcag aataagccac acccagccaa cctacacatt    31800
cgttctgcga gtcacacacg ggaggagcgg gaagagctgg aagaaccatg ttttttttt    31860 tattccaaaa gattatccaa aacctcaaaa tgaagatcta ttaagtgaac gcgctccct    31920 ccggtggcgt ggtcaaactc tacagccaaa gaacagataa tggcatttgt aagatgttgc    31980
acaatggctt ccaaaaggca aacggccctc acgtccaagt ggacgtaaag gctaaaccct    32040
tcagggtgaa tctcctctat aaacattcca gcaccttcaa ccatgcccaa ataattctca    32100
tctcgccacc ttctcaatat atctctaagc aaatcccgaa tatttaagtc cgggccattg    32160
taaaaatttt ggctccagag cgccctccac cttcagcctc aagcagcgaa tcatgattgc    32220
aaaaattcag gttcctcaca gacctgtata agattcaaaa gcggaacatt aacaaaaata    32280
ccgcgatccc gtaggtccct tcgcagggcc agctgaacat aatcgtgcag gtctgcacgg    32340
accagcgcgg ccacttcccc gccaggaacc atgacaaaag aacccacact gattatgaca    32400
cgcatactcg gagctatgct aaccagcgta gccccgatgt aagcttgttg catgggcggc    32460
gatataaaat gcaaggtgct gctcaaaaaa tcaggcaaag cctcgcgcaa aaagaaagc    32520 acatcgtagt catgctcatg cagataaagg caggtaagct ccggaaccac cacagaaaaa    32580
gacaccattt ttctctcaaa catgtctgcg ggtttctgca taaacacaaa ataaataac    32640 aaaaaaacat ttaaacatta gaagcctgtc ttacaacagg aaaaacaacc cttataagca    32700
taagacggac tacggccatg ccggcgtgac cgtaaaaaaa ctggtcaccg tgattaaaaa    32760
gcaccaccga cagctcctcg gtcagtccgg agtcataatg taagactcgg taaacacatc    32820
aggttgattc acatcggtca gtgttaaaaa gcgaccgaaa tagccngggg gaatacaata    32880
cccgcaggcg tagagacaac attacagccc ccataggagg tataacaaaa ttaataggag    32940
agaaaaacac ataaacacct gaaaaaccct cctgcctagg caaatagca ccctcccgct    33000 ccagaacaac atacagcgct tccacagcgg cagccataac agtcagcctt accagtaaaa    33060
aagaaaacct attaaaaaaa caccactcga cacggcacca gctcaatcag tcacagtgta    33120
aaaaagggcc aagtgcagag cgagtatata taggactaaa aaatgacggt aacggttaaa    33180
gtccacaaaa aacacccaga aaaccgcacg cgaacctacg cccagaaacg aaagccaaaa    33240
aacccacaac ttcctcaaat cgtcacttcc gttttcccac gttacgtcac ttcccatttt    33300
aagaaaacta caattcccaa cacatacaag ttactccgcc ctaaaaccta cgtcacccgc    33360
cccgttccca cgccccgcgc cacgtcacaa actccacccc ctcattatca tattggcttc    33420
aatccaaaat aaggtatatt attgatgatg                                    33450
```

<210> SEQ ID NO 8
<211> LENGTH: 3010
<212> TYPE: PRT
<213> ORGANISM: Hepatitis C virus

<400> SEQUENCE: 8

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

-continued

```
Gly Val Tyr Leu Leu Pro Arg Arg Gly Pro Arg Leu Gly Val Arg Ala
             35                  40                  45
Thr Arg Lys Thr Ser Glu Arg Ser Gln Pro Arg Gly Arg Arg Gln Pro
         50                  55                  60
Ile Pro Lys Ala Arg Gln Pro Glu Gly Arg Ala Trp Ala Gln Pro Gly
 65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
            130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Ile Pro Ala Ser Ala Tyr
                180                 185                 190
Glu Val Arg Asn Val Ser Gly Val Tyr His Val Thr Asn Asp Cys Ser
            195                 200                 205
Asn Ala Ser Ile Val Tyr Glu Ala Ala Asp Met Ile Met His Thr Pro
            210                 215                 220
Gly Cys Val Pro Cys Val Arg Glu Asn Asn Ser Ser Arg Cys Trp Val
225                 230                 235                 240
Ala Leu Thr Pro Thr Leu Ala Ala Arg Asn Ala Ser Val Pro Thr Thr
                245                 250                 255
Thr Ile Arg Arg His Val Asp Leu Leu Val Gly Ala Ala Ala Leu Cys
            260                 265                 270
Ser Ala Met Tyr Val Gly Asp Leu Cys Gly Ser Val Phe Leu Val Ala
            275                 280                 285
Gln Leu Phe Thr Phe Ser Pro Arg Arg His Glu Thr Val Gln Asp Cys
            290                 295                 300
Asn Cys Ser Ile Tyr Pro Gly His Val Thr Gly His Arg Met Ala Trp
305                 310                 315                 320
Asp Met Met Met Asn Trp Ser Pro Thr Ala Ala Leu Val Val Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Val Gly Asn Trp
            355                 360                 365
Ala Lys Val Leu Ile Val Met Leu Leu Phe Ala Gly Val Asp Gly Gly
        370                 375                 380
Thr Tyr Val Thr Gly Gly Thr Met Ala Lys Asn Thr Leu Gly Ile Thr
385                 390                 395                 400
Ser Leu Phe Ser Pro Gly Ser Ser Gln Lys Ile Gln Leu Val Asn Thr
                405                 410                 415
Asn Gly Ser Trp His Ile Asn Arg Thr Ala Leu Asn Cys Asn Asp Ser
            420                 425                 430
Leu Asn Thr Gly Phe Leu Ala Ala Leu Phe Tyr Val His Lys Phe Asn
        435                 440                 445
Ser Ser Gly Cys Pro Glu Arg Met Ala Ser Cys Ser Pro Ile Asp Ala
```

-continued

```
            450                 455                 460
Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
                500                 505                 510

Pro Val Val Gly Thr Thr Asp Arg Phe Gly Val Pro Thr Tyr Ser
                515                 520                 525

Trp Gly Glu Asn Glu Thr Asp Val Leu Leu Asn Asn Thr Arg Pro
530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Ile Gly Asn
                565                 570                 575

Lys Thr Leu Thr Cys Pro Thr Asp Cys Phe Arg Lys His Pro Glu Ala
                580                 585                 590

Thr Tyr Thr Lys Cys Gly Ser Gly Pro Trp Leu Thr Pro Arg Cys Leu
                595                 600                 605

Val His Tyr Pro Tyr Arg Leu Trp His Tyr Pro Cys Thr Val Asn Phe
                610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
                660                 665                 670

Gln Val Leu Pro Cys Ser Phe Thr Thr Leu Pro Ala Leu Ser Thr Gly
                675                 680                 685

Leu Ile His Leu His Gln Asn Val Val Asp Val Gln Tyr Leu Tyr Gly
                690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
                740                 745                 750

Val Leu Asn Ala Ala Ser Val Ala Gly Ala His Gly Ile Leu Ser Phe
                755                 760                 765

Leu Val Phe Phe Cys Ala Ala Trp Tyr Ile Lys Gly Arg Leu Val Pro
                770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Ile Leu Thr Leu Ser
                820                 825                 830

Pro His Tyr Lys Leu Phe Leu Ala Arg Leu Ile Trp Trp Leu Gln Tyr
                835                 840                 845

Phe Ile Thr Arg Ala Glu Ala His Leu Gln Val Trp Ile Pro Pro Leu
850                 855                 860

Asn Val Arg Gly Gly Arg Asp Ala Val Ile Leu Leu Thr Cys Ala Ile
865                 870                 875                 880
```

```
His Pro Glu Leu Ile Phe Thr Ile Thr Lys Ile Leu Leu Ala Ile Leu
                885                 890                 895

Gly Pro Leu Met Val Leu Gln Ala Gly Ile Thr Lys Val Pro Tyr Phe
                900                 905                 910

Val Arg Ala His Gly Leu Ile Arg Ala Cys Met Leu Val Arg Lys Val
                915                 920                 925

Ala Gly Gly His Tyr Val Gln Met Ala Leu Met Lys Leu Ala Ala Leu
                930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Asp Met Glu Thr Lys Val Ile Thr Trp Gly Ala Asp Thr Ala Ala
                980                 985                 990

Cys Gly Asp Ile Ile Leu Gly Leu Pro Val Ser Ala Arg Arg Gly Arg
                995                 1000                1005

Glu Ile His Leu Gly Pro Ala Asp Ser Leu Glu Gly Gln Gly Trp
                1010            1015            1020

Arg Leu Leu Ala Pro Ile Thr Ala Tyr Ser Gln Gln Thr Arg Gly
                1025            1030            1035

Leu Leu Gly Cys Ile Ile Thr Ser Leu Thr Gly Arg Asp Arg Asn
                1040            1045            1050

Gln Val Glu Gly Glu Val Gln Val Val Ser Thr Ala Thr Gln Ser
                1055            1060            1065

Phe Leu Ala Thr Cys Val Asn Gly Val Cys Trp Thr Val Tyr His
                1070            1075            1080

Gly Ala Gly Ser Lys Thr Leu Ala Gly Pro Lys Gly Pro Ile Thr
                1085            1090            1095

Gln Met Tyr Thr Asn Val Asp Gln Asp Leu Val Gly Trp Gln Ala
                1100            1105            1110

Pro Pro Gly Ala Arg Ser Leu Thr Pro Cys Thr Cys Gly Ser Ser
                1115            1120            1125

Asp Leu Tyr Leu Val Thr Arg His Ala Asp Val Ile Pro Val Arg
                1130            1135            1140

Arg Arg Gly Asp Ser Arg Gly Ser Leu Leu Ser Pro Arg Pro Val
                1145            1150            1155

Ser Tyr Leu Lys Gly Ser Ser Gly Gly Pro Leu Leu Cys Pro Ser
                1160            1165            1170

Gly His Ala Val Gly Ile Phe Arg Ala Ala Val Cys Thr Arg Gly
                1175            1180            1185

Val Ala Lys Ala Val Asp Phe Val Pro Val Glu Ser Met Glu Thr
                1190            1195            1200

Thr Met Arg Ser Pro Val Phe Thr Asp Asn Ser Ser Pro Pro Ala
                1205            1210            1215

Val Pro Gln Thr Phe Gln Val Ala His Leu His Ala Pro Thr Gly
                1220            1225            1230

Ser Gly Lys Ser Thr Lys Val Pro Ala Ala Tyr Ala Ala Gln Gly
                1235            1240            1245

Tyr Lys Val Leu Val Leu Asn Pro Ser Val Ala Ala Thr Leu Gly
                1250            1255            1260

Phe Gly Ala Tyr Met Ser Lys Ala His Gly Ile Asp Pro Asn Ile
                1265            1270            1275
```

-continued

| | | | | | | | | | | |
|---|---|---|---|---|---|---|---|---|---|---|
| Arg | Thr | Gly | Val | Arg | Thr | Ile | Thr | Thr | Gly | Ala | Pro | Ile | Thr | Tyr |
| 1280 | | | | | 1285 | | | | | 1290 | | | | |

Arg Thr Gly Val Arg Thr Ile Thr Thr Gly Ala Pro Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys His Ser Thr Asp Ser
1310                1315                1320

Thr Thr Ile Leu Gly Ile Gly Thr Val Leu Asp Gln Ala Glu Thr
1325                1330                1335

Ala Gly Ala Arg Leu Val Val Leu Ala Thr Ala Thr Pro Pro Gly
1340                1345                1350

Ser Val Thr Val Pro His Pro Asn Ile Glu Glu Val Ala Leu Ser
1355                1360                1365

Ser Thr Gly Glu Ile Pro Phe Tyr Gly Lys Ala Ile Pro Ile Glu
1370                1375                1380

Thr Ile Lys Gly Gly Arg His Leu Ile Phe Cys His Ser Lys Lys
1385                1390                1395

Lys Cys Asp Glu Leu Ala Ala Lys Leu Ser Gly Leu Gly Leu Asn
1400                1405                1410

Ala Val Ala Tyr Tyr Arg Gly Leu Asp Val Ser Val Ile Pro Thr
1415                1420                1425

Ser Gly Asp Val Ile Val Val Ala Thr Asp Ala Leu Met Thr Gly
1430                1435                1440

Phe Thr Gly Asp Phe Asp Ser Val Ile Asp Cys Asn Thr Cys Val
1445                1450                1455

Thr Gln Thr Val Asp Phe Ser Leu Asp Pro Thr Phe Thr Ile Glu
1460                1465                1470

Thr Thr Thr Val Pro Gln Asp Ala Val Ser Arg Ser Gln Arg Arg
1475                1480                1485

Gly Arg Thr Gly Arg Gly Arg Met Gly Ile Tyr Arg Phe Val Thr
1490                1495                1500

Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Ser Val Arg Leu Arg Ala Tyr Leu Asn Thr Pro Gly Leu
1535                1540                1545

Pro Val Cys Gln Asp His Leu Glu Phe Trp Glu Ser Val Phe Thr
1550                1555                1560

Gly Leu Thr His Ile Asp Ala His Phe Leu Ser Gln Thr Lys Gln
1565                1570                1575

Ala Gly Asp Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Thr Thr
1625                1630                1635

His Pro Ile Thr Lys Tyr Ile Met Ala Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Thr Thr Gly Ser Val Val Ile Val

-continued

```
            1670                1675                1680
Gly Arg Ile Ile Leu Ser Gly Lys Pro Ala Ile Pro Asp Arg
        1685                1690                1695
Glu Val Leu Tyr Arg Glu Phe Asp Glu Met Glu Cys Ala Ser
    1700                1705                1710
His Leu Pro Tyr Ile Glu Gln Gly Met Gln Leu Ala Glu Gln Phe
    1715                1720                1725
Lys Gln Lys Ala Ile Gly Leu Leu Gln Thr Ala Thr Lys Gln Ala
    1730                1735                1740
Glu Ala Ala Pro Val Val Glu Ser Lys Trp Arg Thr Leu Glu
    1745                1750                1755
Ala Phe Trp Ala Lys His Met Trp Asn Phe Ile Ser Gly Ile Gln
    1760                1765                1770
Tyr Leu Ala Gly Leu Ser Thr Leu Pro Gly Asn Pro Ala Ile Ala
    1775                1780                1785
Ser Leu Met Ala Phe Thr Ala Ser Ile Thr Ser Pro Leu Thr Thr
    1790                1795                1800
Gln His Thr Leu Leu Phe Asn Ile Leu Gly Gly Trp Val Ala Ala
    1805                1810                1815
Gln Leu Ala Pro Pro Ser Ala Ala Ser Ala Phe Val Gly Ala Gly
    1820                1825                1830
Ile Ala Gly Ala Ala Val Gly Ser Ile Gly Leu Gly Lys Val Leu
    1835                1840                1845
Val Asp Ile Leu Ala Gly Tyr Gly Ala Gly Val Ala Gly Ala Leu
    1850                1855                1860
Val Ala Phe Lys Val Met Ser Gly Glu Met Pro Ser Thr Glu Asp
    1865                1870                1875
Leu Val Asn Leu Leu Pro Ala Ile Leu Ser Pro Gly Ala Leu Val
    1880                1885                1890
Val Gly Val Val Cys Ala Ala Ile Leu Arg Arg His Val Gly Pro
    1895                1900                1905
Gly Glu Gly Ala Val Gln Trp Met Asn Arg Leu Ile Ala Phe Ala
    1910                1915                1920
Ser Arg Gly Asn His Val Ser Pro Thr His Tyr Val Pro Glu Ser
    1925                1930                1935
Asp Ala Ala Ala Arg Val Thr Gln Ile Leu Ser Ser Leu Thr Ile
    1940                1945                1950
Thr Gln Leu Leu Lys Arg Leu His Gln Trp Ile Asn Glu Asp Cys
    1955                1960                1965
Ser Thr Pro Cys Ser Gly Ser Trp Leu Arg Asp Val Trp Asp Trp
    1970                1975                1980
Ile Cys Thr Val Leu Thr Asp Phe Lys Thr Trp Leu Gln Ser Lys
    1985                1990                1995
Leu Leu Pro Arg Leu Pro Gly Val Pro Phe Phe Ser Cys Gln Arg
    2000                2005                2010
Gly Tyr Lys Gly Val Trp Arg Gly Asp Gly Ile Met Gln Thr Thr
    2015                2020                2025
Cys Pro Cys Gly Ala Gln Ile Thr Gly His Val Lys Asn Gly Ser
    2030                2035                2040
Met Arg Ile Val Gly Pro Arg Thr Cys Ser Asn Thr Trp His Gly
    2045                2050                2055
Thr Phe Pro Ile Asn Ala Tyr Thr Thr Gly Pro Cys Thr Pro Ser
    2060                2065                2070
```

```
Pro Ala Pro Asn Tyr Ser Arg Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Glu Val Thr Phe Leu
    2135                2140                2145

Val Gly Leu Asn Gln Tyr Leu Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Thr Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Thr Arg His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Glu Pro Leu Gln Ala Glu Asp Glu Arg Glu Val
    2255                2260                2265

Ser Val Pro Ala Glu Ile Leu Arg Arg Ser Arg Lys Phe Pro Arg
    2270                2275                2280

Ala Met Pro Ile Trp Ala Arg Pro Asp Tyr Asn Pro Pro Leu Leu
    2285                2290                2295

Glu Ser Trp Lys Asp Pro Asp Tyr Val Pro Pro Val Val His Gly
    2300                2305                2310

Cys Pro Leu Pro Pro Ala Lys Ala Pro Pro Ile Pro Pro Pro Arg
    2315                2320                2325

Arg Lys Arg Thr Val Val Leu Ser Glu Ser Thr Val Ser Ser Ala
    2330                2335                2340

Leu Ala Glu Leu Ala Thr Lys Thr Phe Gly Ser Ser Glu Ser Ser
    2345                2350                2355

Ala Val Asp Ser Gly Thr Ala Thr Ala Ser Pro Asp Gln Pro Ser
    2360                2365                2370

Asp Asp Gly Asp Ala Gly Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Glu Glu Ala Ser Glu Asp Val Val Cys
    2405                2410                2415

Cys Ser Met Ser Tyr Thr Trp Thr Gly Ala Leu Ile Thr Pro Cys
    2420                2425                2430

Ala Ala Glu Glu Thr Lys Leu Pro Ile Asn Ala Leu Ser Asn Ser
    2435                2440                2445

Leu Leu Arg His His Asn Leu Val Tyr Ala Thr Thr Ser Arg Ser
    2450                2455                2460
```

-continued

```
Ala Ser Leu Arg Gln Lys Lys Val Thr Phe Asp Arg Leu Gln Val
2465            2470                2475

Leu Asp Asp His Tyr Arg Asp Val Leu Lys Glu Met Lys Ala Lys
2480            2485                2490

Ala Ser Thr Val Lys Ala Lys Leu Leu Ser Val Glu Glu Ala Cys
2495            2500                2505

Lys Leu Thr Pro Pro His Ser Ala Arg Ser Lys Phe Gly Tyr Gly
2510            2515                2520

Ala Lys Asp Val Arg Asn Leu Ser Ser Lys Ala Val Asn His Ile
2525            2530                2535

Arg Ser Val Trp Lys Asp Leu Leu Glu Asp Thr Glu Thr Pro Ile
2540            2545                2550

Asp Thr Thr Ile Met Ala Lys Asn Glu Val Phe Cys Val Gln Pro
2555            2560                2565

Glu Lys Gly Gly Arg Lys Pro Ala Arg Leu Ile Val Phe Pro Asp
2570            2575                2580

Leu Gly Val Arg Val Cys Glu Lys Met Ala Leu Tyr Asp Val Val
2585            2590                2595

Ser Thr Leu Pro Gln Ala Val Met Gly Ser Ser Tyr Gly Phe Gln
2600            2605                2610

Tyr Ser Pro Gly Gln Arg Val Glu Phe Leu Val Asn Ala Trp Lys
2615            2620                2625

Ala Lys Lys Cys Pro Met Gly Phe Ala Tyr Asp Thr Arg Cys Phe
2630            2635                2640

Asp Ser Thr Val Thr Glu Asn Asp Ile Arg Val Glu Glu Ser Ile
2645            2650                2655

Tyr Gln Cys Cys Asp Leu Ala Pro Glu Ala Arg Gln Ala Ile Arg
2660            2665                2670

Ser Leu Thr Glu Arg Leu Tyr Ile Gly Gly Pro Leu Thr Asn Ser
2675            2680                2685

Lys Gly Gln Asn Cys Gly Tyr Arg Arg Cys Arg Ala Ser Gly Val
2690            2695                2700

Leu Thr Thr Ser Cys Gly Asn Thr Leu Thr Cys Tyr Leu Lys Ala
2705            2710                2715

Ala Ala Ala Cys Arg Ala Ala Lys Leu Gln Asp Cys Thr Met Leu
2720            2725                2730

Val Cys Gly Asp Asp Leu Val Val Ile Cys Glu Ser Ala Gly Thr
2735            2740                2745

Gln Glu Asp Glu Ala Ser Leu Arg Ala Phe Thr Glu Ala Met Thr
2750            2755                2760

Arg Tyr Ser Ala Pro Pro Gly Asp Pro Pro Lys Pro Glu Tyr Asp
2765            2770                2775

Leu Glu Leu Ile Thr Ser Cys Ser Ser Asn Val Ser Val Ala His
2780            2785                2790

Asp Ala Ser Gly Lys Arg Val Tyr Tyr Leu Thr Arg Asp Pro Thr
2795            2800                2805

Thr Pro Leu Ala Arg Ala Ala Trp Glu Thr Ala Arg His Thr Pro
2810            2815                2820

Val Asn Ser Trp Leu Gly Asn Ile Ile Met Tyr Ala Pro Thr Leu
2825            2830                2835

Trp Ala Arg Met Ile Leu Met Thr His Phe Phe Ser Ile Leu Leu
2840            2845                2850

Ala Gln Glu Gln Leu Glu Lys Ala Leu Asp Cys Gln Ile Tyr Gly
```

-continued

```
    2855                2860                2865

Ala Cys  Tyr Ser Ile Glu Pro  Leu Asp Leu Pro Gln  Ile Ile Gln
    2870                2875                2880

Arg Leu  His Gly Leu Ser Ala  Phe Ser Leu His Ser  Tyr Ser Pro
    2885                2890                2895

Gly Glu  Ile Asn Arg Val Ala  Ser Cys Leu Arg Lys  Leu Gly Val
    2900                2905                2910

Pro Pro  Leu Arg Val Trp Arg  His Arg Ala Arg Ser  Val Arg Ala
    2915                2920                2925

Arg Leu  Leu Ser Gln Gly Gly  Arg Ala Ala Thr Cys  Gly Lys Tyr
    2930                2935                2940

Leu Phe  Asn Trp Ala Val Arg  Thr Lys Leu Lys Leu  Thr Pro Ile
    2945                2950                2955

Pro Ala  Ala Ser Gln Leu Asp  Leu Ser Ser Trp Phe  Val Ala Gly
    2960                2965                2970

Tyr Ser  Gly Gly Asp Ile Tyr  His Ser Leu Ser Arg  Ala Arg Pro
    2975                2980                2985

Arg Trp  Phe Met Trp Cys Leu  Leu Leu Leu Ser Val  Gly Val Gly
    2990                2995                3000

Ile Tyr  Leu Leu Pro Asn Arg
    3005                3010
```

COMPOUNDS AND METHODS FOR INHIBITING HEPATITIS C VIRUS REPLICATION

STATEMENT OF GOVERNMENT SUPPORT

Development of this invention was supported by grants P20 RR15569, P20 RR016460, and R01 AI060563 from the National Institutes of Health and funding from U.S. Department of Agriculture. The United States government has certain rights in this invention.

COMPACT DISC

This specification is accompanied by an original compact disc and one identical copy, the contents of which are incorporated by reference. The compact discs each contain the files 110-001US1.txt (96 kb sequence listing file) and Table-2-RTF.doc (845 kb file of Table 2).

BACKGROUND

An estimated 3% of the world's population is seropositive for hepatitis C virus (HCV) (1, 2, 3). Approximately 70% of seropositive individuals develop a chronic infection. Infection with HCV predisposes victims to liver pathology, including fibrosis, cirrhosis, and hepatocellular carcinoma (18). Most seropositive persons eventually develop hepatocellular carcinoma (4), and therefore HCV infection is also the leading cause of liver failure and the need for liver transplants in the U.S. (3,5).

HCV is a 9.6 kb positive strand RNA virus of the Flaviviradae family, genus Hepacivirus (6). The RNA comprises a 5' UTR (untranslated region) of approximately 340 nucleotides that includes an internal ribosome entry sequence (IRES), a single open reading frame (ORF) of approximately 9000 nucleotides and a 3' UTR of approximately 230 nucleotides. The internal ribosome entry sequence mediates initiation of viral RNA. The single open reading frame is translated into a polyprotein of approximately 3000 amino acid residues. This is cleaved by proteases to produce at least three structural proteins (core, E1, and E2) and six non-structural proteins (NS2, NS3, NS4a, NS4b, NS5a, and NS5b) (3).

The core protein forms a capsid, and E1 and E2 interact with plasma membranes of hepatocytes. NS2 is a zinc metalloprotease that cleaves the polyprotein at the NS2-NS3 junction between Leu1026 and Ala1027 (7). NS3 is a bifunctional enzyme, with its N terminus a serine protease that cleaves the rest of the polyprotein in conjunction with its cofactor, NS4a. The C terminus of NS3 is a helicase that is responsible for unwinding and separating putative double-stranded replication intermediates in the HCV life cycle (3,8). The roles of NS4b and NS5a have not been well defined, although it is postulated that NS5a may act as an interferon antagonist. NS5b is an RNA-dependent RNA polymerase that can copy the positive and negative strands of RNA.

Recently another ORF of HCV has been identified, which encodes protein F of unknown function (9).

NS3 is a helicase. Helicases are enzymes that unwind dsDNA and dsRNA in various biological processes, including replication, recombination, and repair. Helicases act by converting the chemical energy of ATP hydrolysis to the mechanical energy of unwinding. NS3 is a 67 kDa, 3'-to-5' RNA-DNA helicase, of the SFII superfamily, and is thought to unwind dsRNA and other secondary structures during HCV replication (11). The oligomeric state of NS3 has been a subject of debate, since it has been shown to be a monomer (12-14), dimer (15), and oligomer (16) in the literature.

The current treatments for HCV infection are alpha interferon (IFN-α) in combination with ribavirin or a polyethylene glycol-modified form of IFN-α. But sustained responses are only observed in about half of the treated patients, and effectiveness varies depending on the HCV genotype (Blight, K. J. et al. 2002. *J. Virol.* 76:13001). Thus, improved treatments for HCV infection are needed. Treatments for HCV infection would include methods of inhibiting HCV replication. Thus, compounds and methods for inhibiting HCV replication are needed. Methods of identifying compounds that inhibit HCV replication are also needed.

SUMMARY

The inventors have discovered that a mutant NS3 gene functions in a dominant-negative manner in inhibiting wild-type NS3 activity and inhibiting HCV replication. That is, the inventors have discovered that expressing an ATPase-deficient NS3 protein from a nucleic acid vector in a cell infected with wild-type HCV replicon partially or completely inhibits replication of the wild-type HCV replicon in the cell. Thus, the mutant NS3 acts in a dominant negative manner. This shows that NS3 protein is an oligomer, and incorporating mutant ATPase-deficient monomers of NS3 in the oligomer with wild-type NS3 monomers inhibits or inactivates the oligomeric enzyme complex. NS3 activity is necessary for replication of HCV, and the inventors have demonstrated that expressing a dominant-negative mutant NS3 gene in cells harboring HCV partially or completely inhibits HCV replication. These data also indicate that administering dominant-negative mutant NS3 protein to cells harboring HCV will inhibit replication of HCV.

The crystal structure of a complex containing a 16-nt DNA complexed with 3 molecules of NS3 helicase is also solved. The crystal structure shows that two NS3 molecules simultaneously bind the DNA and interact with each other. Domain 2 of one molecule and domain 3 of the other molecule interact. The residues in contact with each other include residues 545-553, 584-591, 435-453, 477-488, and 524-536 of NS3.

HCV replicons carrying mutations in NS3 in some of these interface residues were created. The replicons also carried a drug-resistance gene, and when these were transformed into Huh-7 liver cells and transformants were selected for growth in the presence of the drug, an NS3 Δ543-545 deletion mutant and D543K/H545D/Q549A mutant both generated far fewer colonies. The colonies that did grow were much smaller than colonies of cells transformed with wild-type replicon. Replicon carrying an R587D/L588D/K589D/T591D NS3 mutant also supported fewer colonies than wild-type replicon. Despite the large biological effects produced by the NS3 proteins mutant in these residues, the D543K/H545D/Q549A and R587D/L588D/K589D/T591D mutant NS3 proteins had only modestly decreased ATPase and helicase activity in assay conditions measuring the activity of monomeric NS3. The decreases in activity were larger in assays depending on processivity of the NS3 enzyme on a single substrate molecule, which depends more on NS3-NS3 interactions.

These data show the importance of the 541-551 region of NS3 for interaction of NS3 monomers with each other and possibly biologically significant interactions with other proteins. A short peptide carrying the sequence of NS3 residues 541-551 coupled to a sequence that facilitates cell permeation was created. When Huh-7 cells carrying HCV replicon were exposed to this peptide, replication of the HCV was strongly inhibited.

Accordingly, one embodiment of the invention provides a method of inhibiting hepatitis C virus (HCV) replication in cells infected with HCV involving transforming the cells with a vector expressing a dominant-negative mutant NS3 gene, wherein the vector reduces replication of viral nucleic acid in the cells or spread of the virus to other cells.

One embodiment of the invention provides a method of inhibiting HCV replication in cells infected with HCV involving administering to the cells a dominant-negative mutant NS3 protein, wherein the protein reduces replication of viral nucleic acid in the cells or spread of the virus to other cells.

One embodiment of the invention provides a method of testing genetic therapy against hepatitis C virus involving: administering a vector expressing a dominant-negative mutant NS3 gene to a mammal infected with HCV; and monitoring replication of HCV in the mammal.

One embodiment of the invention provides a method of inhibiting hepatitis C virus (HCV) replication in cells infected with HCV involving: contacting the cells with an agent that inhibits NS3 enzyme activity by inhibiting NS3 oligomerization; wherein the agent reduces replication of viral nucleic acid in the cells or spread of virus to other cells.

One embodiment of the invention provides a peptide comprising at least 4 contiguous residues of HIDAHFLSQTK (SEQ ID NO:1, residues 541-551 of NS3); wherein the peptide has 100 or fewer amino acid residues; wherein the peptide inhibits hepatitis C virus replication, or inhibits NS3 enzyme activity by inhibiting NS3 oligomerization.

One embodiment of the invention provides a complex for inhibiting hepatitis C virus (HCV) replication containing: an inhibitory peptide comprising 4 or more contiguous residues of HIDAHFLSQTK (SEQ ID NO:1, residues 541-551 of NS3), complexed with a cell-entry vehicle; wherein the complex inhibits replication of HCV in mammalian cells.

One embodiment of the invention provides a compound of molecular weight 10,000 or less, wherein the compound interacts with NS3 to inhibit NS3 oligomerization and wherein the compound inhibits hepatitis C virus (HCV) replication.

Another embodiment of the invention provides a method of identifying a compound that inhibits hepatitis C virus (HCV) replication involving: (a) contacting a cell comprising an HCV replicon with a candidate compound; and (b) monitoring replication of the HCV replicon; wherein the candidate compound inhibits NS3 enzyme activity by inhibiting NS3 oligomerization.

Another embodiment of the invention provides a method of identifying a candidate compound to test for inhibiting HCV virus replication involving: (a) applying a 3-dimensional molecular modeling algorithm to spatial coordinates of a molecular interface of NS3; and (b) electronically screening stored spatial coordinates of a set of compounds against the spatial coordinates of the molecular interface of NS3 to identify at least one candidate compound that is expected to bind to the molecular interface of NS3.

Another embodiment of the invention provides a computer-assisted method for designing a candidate inhibitor compound for inhibiting hepatitis C virus (HCV) replication involving: (a) supplying to a computer modeling application a set of spatial coordinates of a molecular interface of NS3; (b) computationally building an agent represented by a set of structural coordinates; and (c) determining whether the agent is expected to bind to the molecular interface of NS3; wherein if the agent is expected to bind to the interface of NS3 it is a candidate inhibitor compound.

Another embodiment of the invention provides an isolated and purified viral vector comprising: a viral capsid; encasing viral nucleic acid comprising a dominant-negative NS3 gene operably linked to a promoter active in mammalian cells.

BRIEF DESCRIPTION OF THE DRAWINGS

FIG. 4 is a plot of luciferase activity of cells transformed with ATPase-deficient mutant HCV-Luc (mtrep) and increasing concentrations of plasmid expressing wt-NS3 or control cells transformed with wt HCV-Luc (wtrep).

DETAILED DESCRIPTION

Figure 1:
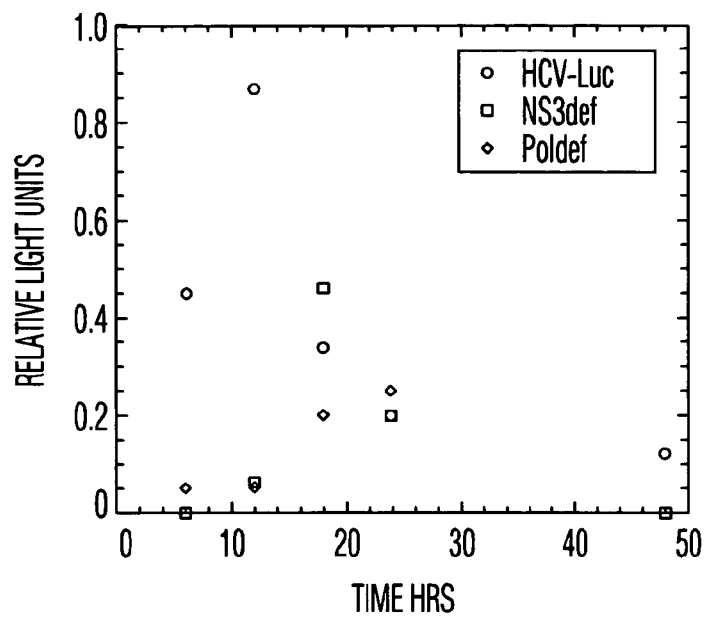
FIG. 1 shows a time course of luciferase activity in Huh-7 cells transfected with HCV-luciferase replicon.

Definitions:

The term "inhibiting" hepatitis C virus replication includes partial and complete inhibition of the replication.

The term "replication" of HCV refers to replication of copies of the virus or viral nucleic acid within a cell and/or spread of the virus or viral nucleic acid to other cells.

The term "hepatitis C virus" includes a wild type, mutant, or engineered hepatitis C virus (e.g., hepatitis C replicons, such as reported in references 17 and 18). Hepatitis C virus comprises a single-stranded RNA molecule, optionally encased in a capsid. If the virus is an engineered, truncated, or mutant form of the virus, the viral RNA is a substantial portion of the full-length viral RNA (e.g., at least 30%, preferably at least 50%, more preferably at least 70%, 80%, or 90% of the full-length viral RNA) and has in that portion at least 90%, more preferably at least 95%, most preferably at least 98% sequence identity with the wild-type viral RNA sequence (SEQ ID NO:6, genbank accession number AJ238799). Sequence identity is calculated using the default BLAST parameters for nucleotide sequence comparison at the PubMed website, www.ncbi.nlm.nih.gov/PubMed/.

"Cells infected with HCV" refers to cells harboring HCV nucleic acid. "HCV nucleic acid" refers to viral RNA or to DNA encoding and capable of being transcribed into viral RNA. The infected cells may be transformed with viral RNA either as naked RNA or encased in the capsid, or the cells may be transformed by DNA (e.g. a plasmid) encoding and capable of being transcribed into viral RNA.

A vector that is a "virus" refers to a viral nucleic acid encased in a capsid.

The term "NS3 gene" refers to any nucleic acid, whether cDNA, viral RNA, or other source, that encodes an NS3 protein.

"Wild-type NS3 gene" refers to a gene that encodes the NS3 protein having SEQ ID NO:3, or another natural source homologous NS3 protein from a hepatitis C virus found in nature. One wild-type NS3 gene is nucleotides 3079-4971 of SEQ ID NO:6.

A "dominant-negative mutant NS3 gene" is an NS3 gene that when expressed in cells harboring and expressing a wild-type NS3 gene reduces the activity of the wild-type NS3 protein. The mutant NS3 gene can express a truncated, full-length, or extended NS3 protein. At least a portion of the mutant NS3 protein is homologous to wild-type NS3 protein.

A mutant NS3 protein is "ATPase deficient" if it has ATPase activity that is statistically significantly lower than the activity of the wild-type NS3 protein. Activity can be assayed by any standard method, such as the spectrophotometric coupled ATPase assay (23). Lower activity includes a lower $k_{cat}$, a higher $K_M$, or a combination of both. In particular embodiments, the ATPase-deficient mutant NS3 has less than 75%, less than 50%, less than 10%, less than 5%, or less than 1% of the ATPase activity of the wild-type NS3.

The term "vector" as used herein refers to any nucleic acid capable of transforming target cells and expressing an inserted NS3 gene. The vector may be autonomously replicating or not, double-stranded or single-stranded, and encased in viral capsid or not. Vectors include viruses comprising capsid and nucleic acid, viral nucleic acid without capsid, DNA plasmids, linear DNA molecules, and linear or circular RNA molecules.

The term "monitoring replication of HCV" includes monitoring direct effects of HCV replication, such as health effects, e.g., development of hepatocellular carcinoma.

The term "peptide" refers to a peptide of 2 to 100 amino acid residues that, if derived from a naturally occurring protein, is shorter than the naturally occurring protein. A "peptide" as used herein may include amino acids that are L stereoisomers (the naturally occurring form) or D stereoisomers. Peptides may be linear, branched, or circular. Peptides may include amino acids other than the 20 common naturally occurring amino acids, such as β-alanine, ornithine, or methionine sulfoxide. The term "peptide" also includes peptides modified on one or more alpha-amino, alpha-carboxyl, or side-chain, e.g., by appendage of a methyl, formyl, acetyl, glycosyl, phosphoryl, and the like.

The term "transforming" refers to any method that results in nucleic acid being taken up into a cell. This includes, for instance, CaCl$_2$-mediated uptake of plasmid DNA, cellular uptake of naked viral RNA, or transfection of a cell with a virus.

The term "molecular interface" of NS3 refers to a surface of NS3 exposed to solvent or otherwise available to bind with an agent.

The term "complexed" in the context of a vector "complexed" with an agent for targeting to the liver includes covalent coupling of vector to the agent and a non-covalent interaction between the vector and the agent that is sufficiently stable to facilitate targeting to the liver.

A candidate compound for inhibiting HCV replication is "expected to bind" to a molecular interface of NS3 if a free energy calculation or computerized molecular modeling application, such as is provided by the program DOCK-5, calculates based on the docking of spatial coordinates of the compound with spatial coordinates of the molecular interface that the compound will bind to the molecular interface, or that the compound has an approximately equal or greater binding affinity than a known inhibitor of NS3 oligomerization, such as peptide SEQ ID NO:1 or SEQ ID NO:2.

Description:

One embodiment of the invention provides a method of inhibiting HCV replication in cells infected with HCV involving transforming cells with a vector expressing a dominant-negative mutant NS3 gene. In a particular embodiment of the invention, the dominant-negative mutant NS3 gene expresses an ATPase-deficient NS3 protein. For instance, an example of an ATPase-deficient NS3 protein is D290A NS3, a mutant NS3 protein in which aspartic acid residue 290 is changed to alanine. (The amino acid numbering in this case refers to the SEQ ID NO:3 NS3 protein with genbank accession number CAB4667, not to the polyprotein.)

In a particular embodiment, the dominant-negative mutant NS3 gene expresses a helicase-deficient NS3 protein. Helicase activity can be assayed, for instance, by the unwinding assay of reference 21.

In one embodiment, the dominant-negative mutant NS3 gene expresses a protease-deficient NS3 protein. Protease activity can be assayed, for instance, as described in reference 34.

In one embodiment of the invention, the mutant NS3 protein amino acid sequence is at least 90% identical to wild-type NS3. In one embodiment, the mutant NS3 protein amino acid sequence is at least 90% identical to wild-type NS3 and contains the D290A mutation. Sequence identity can be calculated using the default BLAST parameters for protein sequence comparison at the PubMed website, www.ncbi.nlm.nih.gov/PubMed/.

In one embodiment of the invention, the infected cells are liver cells.

In one embodiment, the liver cells are Huh-7 cells.

In one embodiment, the infected cells are in vitro. In one embodiment, the infected cells are in vivo in a mammal. In particular embodiments, the mammal is a mouse, rat, rabbit, goat, guinea pig, dog, pig, cat, or chimpanzee. The mouse and chimpanzee are particularly preferred model animals. In a particular embodiment, the mammal is a human.

The vector expressing the dominant-negative mutant NS3 gene can be any appropriate vector. For instance, it can be a plasmid, virus, or viral nucleic acid. It can be naked nucleic acid, e.g., a nucleic acid with or without an origin of replication. The vector, e.g., a naked nucleic acid, can be a transposon or include a transposon.

Where the vector is a virus or viral nucleic acid, the virus can be a retrovirus, e.g., a murine leukemia virus.

The vector can be targeted to the liver. One mechanism of doing this is to complex the vector with an agent for targeting to the liver, such as asialoorosomucoid. Methods of coupling vectors to asialoorosomucoid are reviewed in reference 31.

A method of coupling a vector to asialoorosomucoid and to adenovirus particles is disclosed in reference 30. The adenovirus particles enhance expression by efficiently lysing the endosomes following receptor-mediated endocytosis.

Preferably, the NS3 protein is expressed from the vector as a separate protein (i.e., not part of a polyprotein).

In one embodiment, the NS3 gene integrates into chromosomal DNA in the transformed cells.

In one embodiment, the vector is complexed with an endosomolytic peptide. This improves transformation efficiency by lysing the endosomes containing the vector following endocytosis of the vector. (See reference 30.)

The invention also provides a method of inhibiting HCV replication in cells infected with HCV involving administering to the cells a dominant-negative mutant NS3 protein.

In a particular embodiment of the method involving protein administration, the infected cells are liver cells (e.g., Huh-7 cells).

The infected cells can be in vitro or in vivo in a mammal. The mammal can be, for instance, a mouse, rat, rabbit, goat, guinea pig, dog, pig, cat, chimpanzee, or human. In specific preferred embodiments, the mammal is a mouse or chimpanzee. In another preferred embodiment, the mammal is a human.

The protein can be complexed with an agent for targeting to the liver, such as asialoorosomucoid.

A nucleic acid vector or mutant NS3 protein can also be targeted to the liver by surgical techniques, including intraportal injection, intra-vena cava injection, intra-bile duct injection and including tail vein injection in the mouse or rat. These methods are disclosed in reference 33.

Another embodiment of the invention provides a method of testing genetic therapy against HCV involving: administering a vector expressing a dominant-negative mutant NS3 gene to a mammal infected with HCV; and monitoring replication of HCV in the mammal. The monitoring could be by monitoring direct or indirect evidence of HCV replication. For instance, HCV nucleic acid replication in infected cells could be monitored, the number of infected cells could be monitored, or effects of HCV replication, such as development of hepatic carcinoma, could be monitored.

One embodiment of the invention provides a method of inhibiting hepatitis C virus (HCV) replication in cells infected with HCV involving: contacting the cells with an agent that inhibits NS3 enzyme activity by inhibiting NS3 oligomerization; wherein the agent reduces replication of viral nucleic acid in the cells or spread of virus to other cells.

In a particular embodiment of the method of inhibiting HCV replication, the agent includes a peptide comprising the sequence HIDAHFLSQTK (SEQ ID NO:1). In a particular embodiment, the agent is a peptide having the sequence HIDAHFLSQTKGGGYARAAARQARA (SEQ ID NO:2).

In some embodiments, the agent comprises a peptide comprising the reverse D analog of SEQ ID NO:1. This is the peptide having the reverse sequence of SEQ ID NO:1 (or a portion thereof, e.g., at least 4 contiguous residues), where the amino acids are D isomers instead of L isomers.

In another embodiment, the agent comprises an ATPase-deficient mutant NS3 protein.

The cells infected with HCV and contacted with the agent can be in vitro or in vivo in a mammal.

Another embodiment of the invention provides a complex for inhibiting hepatitis C virus (HCV) replication that includes: (a) an inhibitory peptide comprising 4 or more contiguous residues of SEQ ID NO:1; complexed with (b) a cell-entry vehicle; wherein the complex inhibits replication of HCV in mammalian cells.

The inhibitory peptide in other embodiments, contains 5, 6, 7, 8, 9, 10, or all 11 contiguous residues of SEQ ID NO:1.

In particular embodiments, the cell-entry vehicle is a cell-entry peptide, such as YARAAARQARA (SEQ ID NO:4), or an oligoarginine peptide (66, 67).

In a particular embodiment, the cell-entry vehicle is cholesterol. The cholesterol may be covalently attached to the inhibitor peptide, or may be non-covalently complexed with the inhibitor peptide.

In other particular embodiments, the cell-entry vehicle is a liposome.

In a particular embodiment, the complex comprises a liver-targeting entity. In a particular embodiment, the cell-entry vehicle is also a liver-targeting entity.

The liver-targeting entity may be, for instance, asialoorosomucoid.

Another embodiment of the invention provides a peptide comprising at least 4 contiguous residues of SEQ ID NO:1; wherein the peptide has 100 or fewer amino acid residues; wherein the peptide inhibits hepatitis C virus replication, or inhibits NS3 enzyme activity by inhibiting NS3 oligomerization.

Inhibiting NS3 enzyme activity by inhibiting NS3 oligomerization can be demonstrated by greater inhibition of the NS3 enzyme activities that depend more on NS3 oligomerization (NS3-NS3 contacts) than of the enzyme activities that are carried out more equally efficiently by NS3 monomers and NS3 oligomers. For instance, steady-state unwinding with an excess of double-stranded DNA substrate over NS3 enzyme reflects monomer activity because it is unlikely two molecules of NS3 bind to the same substrate molecule in the presence of a large excess of DNA. An assay is described in Example 3 with the results presented in FIG. 12. In contrast, ATP-independent unwinding under single-turnover conditions with excess enzyme is more dependent on NS3-NS3 interactions. An assay under these conditions is described in Example 3 and the results are shown in FIG. 13. Thus, if an agent inhibits NS3 activity by inhibiting NS3 oligomerization, it will inhibit ATP-independent DNA unwinding under single-turnover conditions with excess enzyme more efficiently than it will inhibit steady-state unwinding with an excess of DNA substrate.

The ATPase activity of NS3 is also dependent on NS3 concentration. It increases with increasing NS3 concentration, indicating that the enzyme activity is dependent on NS3 oligomerization (16). An agent that inhibits NS3 activity by inhibiting NS3 oligomerization will have a lower $K_1$ when assayed with low NS3 concentration than when assayed with a higher NS3 concentration.

In particular embodiments of the invention, the inhibitory peptide has 50 or fewer, or 30 or fewer, amino acid residues.

One embodiment of the invention provides a compound of molecular weight 10,000 or less, wherein the compound interacts with NS3 to inhibit NS3 oligomerization and wherein the compound inhibits hepatitis C virus (HCV) replication.

In particular embodiments, the structure of the compound fits a molecular interface of NS3 such that a free energy calculation (or molecular docking computer program) predicts the compound is expected to bind to the molecular interface of NS3.

That is, the compound has a structure that can be represented by spatial coordinates; wherein the spatial coordinates of the compound fit spatial coordinates of an interface of NS3 such that a free energy calculation predicts the compound binds to the interface of NS3.

In some embodiments, the molecular interface of NS3 which the compound fits includes at least one amino acid residue (preferably three or more residues) selected from residues 541-553, 584-591, 435-453, 477-488, and 524-536 of SEQ ID NO:3. A peptide comprising SEQ ID NO:1, residues 541-551 of NH3, was found to inhibit HCV replication. Residues 541-551 of chain B interact with a cleft formed by residues 477-481 and 452-453 of chain A in the crystal structure. Thus, in a particular embodiment, the interface of NS3 that the compound fits includes at least one (preferably all) of residues 477-481 and 452-453.

In particular embodiments, the compound has a molecular weight of 5,000 or less, 2,500 or less, or 1,000 or less.

One embodiment of the invention provides an isolated and purified viral vector comprising: a viral capsid; encasing viral nucleic acid comprising a dominant-negative NS3 gene operably linked to a promoter active in mammalian cells. The viral nucleic acid refers to nucleic acid of which more than 50% originates from a virus. The viral nucleic acid is typically recombinant. The viral nucleic acid can include heterologous segments from non-viral sources. In some embodiments, the viral nucleic acid may include the genes necessary for replication and spread of the virus to other cells. In some embodiments it may not include those genes.

In a particular embodiment, the viral nucleic acid is recombinant HCV nucleic acid.

In a particular embodiment, the viral capsid and viral nucleic acid are hepatitis C virus capsid and nucleic acid.

In a particular embodiment, the viral capsid and viral nucleic acid are not hepatitis C virus capsid and nucleic acid.

In a particular embodiment, the viral capsid and viral nucleic acid are adenovirus capsid and nucleic acid.

In a particular embodiment, the viral capsid and nucleic acid are adeno-associated virus capsid and nucleic acid or retroviral capsid and nucleic acid.

In a particular embodiment, the promoter is cauliflower mosaic virus promoter.

Computer-Assisted Methods of Identifying HCV Inhibitors

One subject of this invention is a computer-assisted method for identifying a potential inhibitor of NS3 oligomerization and thereby HCV replication. The method comprises providing a computer modeling application with a set of relative structural coordinates of NS3, or a molecular interface thereof; supplying the computer modeling application with a set of structural coordinates of a candidate inhibitor of NS3 oligomerization; comparing the two sets of coordinates and determining whether the candidate inhibitor is expected to bind to NS3 or to interfere with NS3 oligomerization. Binding to NS3, particularly on an interface involved in NS3 oligomerization, is indicative of inhibiting NS3 oligomerization and thereby inhibiting HCV replication. In most instances, determining whether the candidate inhibitor is expected to bind to a molecular interface of NS3 includes performing a fitting operation or comparison between the candidate inhibitor and NS3 or an NS3 molecular interface, followed by computational analysis of the outcome of the comparison in order to determine the association between the candidate inhibitor and the NS3 interface, or the interference of the candidate inhibitor with NS3-NS3 oligomerization. A candidate inhibitor identified by such methods is a candidate anti-HCV agent. Optionally, a candidate anti-HCV agent can be synthesized or otherwise obtained and further assessed (e.g., in vitro, in cells or in an appropriate animal model) for its ability to inhibit HCV replication.

Another embodiment of the invention provides a method of identifying a candidate compound to test for inhibiting HCV virus replication involving: (a) applying a 3-dimensional molecular modeling algorithm to spatial coordinates of a molecular interface of NS3; and (b) electronically screening stored spatial coordinates of a set of compounds against the spatial coordinates of the molecular interface of NS3 to identify at least one candidate compound that is expected to bind to the molecular interface of NS3. A suitable molecular modeling application is DOCK-5, available at http://dock.compbio.ucsf.edu.

In a particular embodiment, the molecular interface of NS3 comprises at least one amino acid residue (preferably at least three residues) selected from residues 541-553, 584-591, 435-453, 477-488, and 524-536 of SEQ ID NO:3.

In a particular embodiment, the molecular interface of NS3 comprises at least one amino acid residue selected from residues 477-481 and 452-453 of SEQ ID NO:3. In another embodiment, the molecular interface comprises residues 477-481 and 452-453 of SEQ ID NO:3.

In a particular embodiment, the method further involves comparing the spatial coordinates of the at least one compound to spatial coordinates of peptide SEQ ID NO:1 to determine whether the at least one compound is structurally similar to at least a portion of SEQ ID NO:1. The spatial coordinates of peptide SEQ ID NO:1 can be the spatial coordinates of the free peptide or of residues 541-551 of NS3, as is provided in Example 3 (chain B).

In a specific embodiment, the computer-assisted method of identifying a candidate inhibitor for inhibiting HCV replication that inhibits NS3 oligomerization comprises the steps of (1) supplying a computer modeling application the coordinates of a known agent that binds a molecular interface of NS3 (namely the peptide SEQ ID NO:1) and the coordinates of NS3 or an NS3 molecular interface; (2) quantifying the fit of the known agent to the NS3 molecular interface; (3) supplying the computer modeling application with a set of structural coordinates of an agent to be assessed to determine if it binds a molecular interface of NS3; (4) quantifying the fit of the test agent in the molecular interface using a fit function; (5) comparing the fit calculation for the known agent with that of the test agent; and (6) selecting a test agent that has a fit that is better than, or approximates the fit of the known agent.

Another embodiment of the invention provides a computer-assisted method for designing a candidate inhibitor compound for inhibiting hepatitis C virus (HCV) replication involving: (a) supplying to a computer modeling application a set of spatial coordinates of a molecular interface of NS3; (b) computationally building an agent represented by a set of structural coordinates; and (c) determining whether the agent is expected to bind to the molecular interface of NS3; wherein if the agent is expected to bind to the interface of NS3 it is a candidate inhibitor compound. A suitable molecular modeling application is DOCK-5, available at http://dock.compbio.ucsf.edu.

In particular embodiments, the molecular interface of NS3 includes at least one amino acid residue selected from residues 541-553, 584-591, 435-453, 477-488, and 524-536 of SEQ ID NO:3.

In a particular embodiment, the molecular interface of NS3 comprises at least one amino acid selected from residues 477-481 and 452-453 of SEQ ID NO:3. In another embodiment, the molecular interface comprises residues 477-481 and 452-453 of SEQ ID NO:3.

In a particular embodiment, the method further involves comparing the spatial coordinates of the at least one compound to spatial coordinates of peptide SEQ ID NO:1 to determine whether the at least one compound is structurally similar to at least a portion of SEQ ID NO:1. The spatial coordinates of peptide SEQ ID NO:1 can be the spatial coordinates of the free peptide or of residues 541-551 of NS3, as is provided in Example 3 (chain B).

One skilled in the art may use one of several methods to screen chemical entities or fragments for their ability to associate with a molecular interface of NS3, and more particularly with an interface involved in NS3-NS3 interactions. This process may begin, for example, by visual inspection of the molecular interface on the computer screen based on the NS3 atomic coordinates provided herein. Selected fragments or chemical entities may then be positioned relative to the interface of NS3. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include:

GRID (68) (available from Oxford University, Oxford, UK).

MCSS (69) (available from Molecular Simulations, Burlington, Mass.).

AUTODOCK (70) (available from Scripps Research Institute, La Jolla, Calif.).

DOCK (71) (available from University of California, San Francisco, Calif.).

A commercially available computer database for small molecular compounds includes Cambridge Structural Database and Fine Chemical Database. For a review see reference 72.

Once suitable chemical entities or fragments have been selected, they can be assembled into a single compound or inhibitor. Assembly may be proceeded by visual inspection of the relationship of the fragments to each other on the three-dimensional image displayed on a computer screen in relation to the structure coordinates of NS3. This would be followed by manual model building using software such as Quanta or Sybyl.

Useful programs to aid one of skill in the art in connecting the individual chemical entities or fragments include:

CAVEAT (73) (available from the University of California, Berkeley, Calif.).

3D Database systems such as MACCS-3D (MDL Information Systems, San Leandro, Calif.) This area is reviewed in reference 74.

HOOK (available from Molecular Simulations, Burlington, Mass.).

Instead of proceeding to build an inhibitor of NS3 oligomerization in a step-wise fashion one fragment or chemical entity at a time as described above, inhibitory or other type of binding compounds may be designed as a whole or "de novo" using either an empty active site or optionally including some portion(s) of a known inhibitor(s). Programs to execute these methods include:

LUDI (75) (available from Biosym Technologies, San Diego, Calif.).

LEGEND (76) (available from Molecular Simulations, Burlington, Mass.).

LeapFrog (available from Tripos Associates, St. Louis, Mo.).

Other molecular modeling techniques may also be employed to screen for inhibitors of NS3 oligomerization. See, e.g., references 77 and 78. For example, where the structures of test compounds are known, a model of the test compound may be superimposed over the model of the structure of the invention. Numerous methods and techniques are known in the art for performing this step. Any of these may be used. See, e.g., references 79-81, U.S. Pat. Nos. 5,331,573, and 5,500,807. The model building techniques and computer evaluation systems described herein are not a limitation on the present invention.

Medical Therapy and Pharmaceutical Compositions

Another embodiment of the invention provides a vector that expresses a dominant-negative mutant NS3 gene for use in medical therapy.

Another embodiment of the invention provides a use of a vector expressing a dominant-negative mutant NS3 gene to prepare a medicament effective to reduce replication of hepatitis C virus in a mammal such as a human.

Another embodiment of the invention provides a dominant-negative mutant NS3 protein for use in medical therapy. Another embodiment provides a use of a dominant-negative mutant NS3 protein to prepare a medicament effective to reduce replication of hepatitis C virus in a mammal such as a human.

Another embodiment of the invention provides an agent that inhibits HCV replication in cells infected with HCV and inhibits NS3 enzyme activity by inhibiting NS3 oligomerization for use in medical therapy. Another embodiment provides a use of an agent that inhibits NS3 enzyme activity by inhibiting NS3 oligomerization to prepare a medicament effective to reduce replication of HCV in a mammal, such as a human.

The invention also provides a pharmaceutical composition comprising an anti-HCV agent of the invention, or a pharmaceutically acceptable salt thereof, in combination with a pharmaceutically acceptable diluent. The anti-HCV agents of the invention include (1) a vector expressing a dominant-negative mutant NS3 gene, (2) an isolated and purified viral vector comprising a viral capsid encasing viral nucleic acid that comprises a dominant-negative NS3 gene operably linked to a promoter active in mammalian cells, (3) a dominant-negative mutant NS3 protein, (4) an agent that inhibits NS3 enzyme activity by inhibiting NS3 oligomerization, (5) a complex for inhibiting HCV replication comprising an inhibitory peptide comprising 4 or more contiguous residues of SEQ ID NO:1 complexed with a cell-entry vehicle, (6) a peptide comprising at least 4 contiguous residues of SEQ ID NO:1 wherein the peptide has 100 or fewer amino acid residues and inhibits hepatitis C virus replication, and (7) a compound of molecular weight 10,00 or less wherein the compound interacts with NS3 to inhibit NS3 oligomerization and inhibits HCV replication.

In cases where the anti-HCV agents are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present agents may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the agents may be combined with one or more excipients and used in the form of ingestible tablets, buccal tablets, troches, capsules, elixirs, suspensions, syrups, wafers, and the like. Such compositions and preparations should contain at least 0.1% of agent. The percentage of the compositions and preparations may, of course, be varied and may conveniently be between about 2 to about 60% of the weight of a given unit dosage form. The amount of the agent in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the agent may be incorporated into sustained-release preparations and devices.

The agents may also be administered intravenously or intraperitoneally by infusion or injection. Solutions of the agents can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present agents may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the agents of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the anti-HCV agents of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The invention will now be illustrated by the following non-limiting examples.

EXAMPLES

Example 1

ATPase-Deficient Mutant NS3 Protein Acts in a Dominant Negative Manner to Inhibit Wild-Type NS3 Activity and Inhibit Hepatitis C Virus Replication Experimental Procedures:

Plasmid Construction: DNA sequences encoding wild-type NS3 or mutant NS3 having an alanine in place of aspartic acid at position 290 of NS3 (position 1361 of the polyprotein) (designated D290A NS3 or mNS3) were PCR amplified from a pET-26b plasmid carrying the NS3 gene using Pfu turbo. The PCR-amplified sequences were incorporated into pBUDCE4.1 plasmid (Invitrogen) by blunt end ligation. These plasmids drive the expression of NS3 via a mammalian expression promoter (CMV promoter) and can be used in cell culture experiments. They were sequenced to confirm incorporation of the NS3 gene and named pwtNS3 and pmNS3 for the wild type and the mutant forms, respectively.

Site-directed mutagenesis was performed on a pUC-18-NS3 plasmid, which contains all the nucleotides of the wild-type NS3 gene and serves as the shuttle vector for mutation of the replicon plasmid using the QUIK CHANGE site-directed mutagenesis kit (Stratagene) to incorporate the D290A mutation in the NS3 region of the plasmid. This mutation was confirmed by sequencing and called pUC-mNS3. The mutated NS3 gene was cut out from this plasmid using PmeI and MluI restriction enzymes and incorporated into the replicon vector HCV rep1b BartMan/AvaII Luciferase replicon (19), cut with the same enzymes, by ligation. The ligation mix was transformed to give the mutant replicon.

RNA synthesis: The replicon DNA having the luciferase reporter gene was digested with ScaI for 3 hrs, followed by in-vitro transcription with the AMBION MEGASCRIPT kit according to the manufacturer's directions. The RNA was stored at −80° C.

HCV Replicon assays: Huh-7 cells were transiently transfected with replicon RNA having a firefly (*P. pyralis*) luciferase gene (0.2 µg/well), and with a control plasmid pRL (0.05 µg/well) having a *renilla* (*R. reniformis*) luciferase gene, using DMRIEC (Invitrogen) reagent as per the kit protocol (19). The specific additions of pmNS3, mutant replicon, pwt-NS3 etc were done concurrently. The cells were lysed after 48 hours, and luciferase activity detected using the DUAL LUCIFERASE assay kit (Promega) (24, 25).

Trans complementation assays: These assays were performed in the same manner as the regular replicon assays except that in the trans complementation assays two RNA's of different replicons (wild type and the mutant) were added along with a pRL plasmid to control for transfection efficiency.

Colony formation assays: Huh-7 cells stably transfected with S22041-mutant-containing replicon (2204 refers to the amino acid residue number in the polyprotein, genbank accession number AJ238799, SEQ ID NO:8) with a neomycin resistance gene were transfected with increasing concentration of pmNS3 and pwtNS3 and plated on 100 mm plates with 10 ml of DMEM media with 10% FBS and 1% non-essential amino acids (lipofection media) and allowed to grow for 24 hours. After 24 hours the media was changed to lipofection media containing G418 (Cellgro) at 500 µg/ml concentration. The cells were kept under the selection medium for 21 days for colony formation. At the end of 21 days the plates were washed with PBS and then stained with 0.1% crystal violet Excess stain was washed with PBS and colonies were observed.

Results:

Time course of HCV-Luc RNA transfection demonstrates that replication can be detected at 48 hours in Huh-7 cells: Huh-7 cells were plated in a 12-well plate at 70-80% confluency. Cells were transfected with HCV-Luc replicon, HCV-Luc replicon incorporating a mutation in NS3 rendering it ATPase deficient (NS3 def), and HCV-Luc replicon with a mutation in NS5b rendering it polymerase deficient (Pol def), as well as with a *renilla* luciferase plasmid that serves as an internal control. (FIG. 1.) Cells were lysed using passive lysis buffer (Promega) for 15 minutes on ice and a dual luciferase assay was done to test for replication activity.

Replicon with an ATPase-deficient NS3 (D290A of NS3, D1361A of the polyprotein) (16) and replicon with a polymerase-deficient NS5b (G317A, D318A, D319G triple mutant NS5b) are both inactive in replication after 48 hours. In contrast, the wild-type replicon is still active at 48 hours, showing a persistent level of RNA (FIG. 1). This time course allows us to look at effects on replication at 48 hrs.

NS3 protein is detectable in all the plasmid constructs: Cell lysates from cells transformed with the plasmid expressing ATPase-deficient mutant NS3 (mNS3) or wild-type NS3, as well as cells transfected with wild-type HCV-Luc replicon or the HCV-Luc replicon with the ATPase-deficient mutant NS3 were subjected to western blot analysis. Equal amounts of cell lysates were run on a 12% polyacrylamide gel, the proteins were then transferred onto a PVDF membrane (Osmonics) for an hour. The membrane was blocked in 5% non-fat dry milk containing TBS-Tween (0.1%) for 1 hour, followed by incubation of the membrane in primary antibody overnight at 4° C. The membrane was subjected to 5 washes of 5 minutes each with TBS-Tween, followed by 1 hour incubation in secondary antibody (goat anti-rabbit IgG-HRP) from Biolabs. This was followed by 5 washes of 5 minutes each with TBS-Tween. The protein was detected using ECL chemi-luminiscent kit (Amersham Pharmacia).

Figure 2:
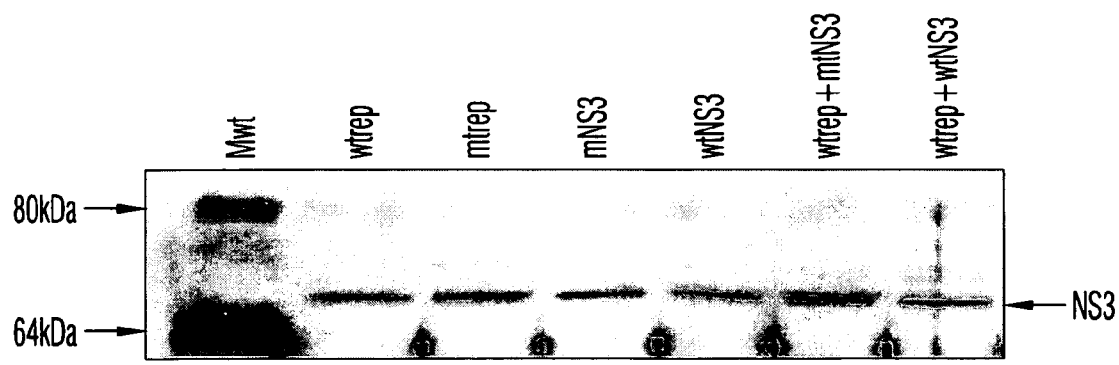
FIG. 2 is a western blot showing detection of NS3 protein in cell lysates from cells transfected with HCV replicon (wtrep and mrep) and NS3-expressing plasmids (mNS3 and wtNS3).

Western analysis of NS3 protein in both mutant and wild type form, as well as the two replicons demonstrates that NS3 protein is present in cell extracts at 48 hours post transfection (FIG. 2).

In vivo the dominant negative mNS3 (pmNS3) down regulates the activity of the HCV-Luc replicon: Huh-7 cells were plated in a 12-well plate at 0.1 million cells per well. The cells were grown to 70-80% confluency and then transfected with the replicon (HCV-Luc) RNA (0.2 µg/well), with *renilla* luciferase plasmid (internal control), and increasing concentrations of mutant NS3 plasmid under a mammalian expression promoter using DMRIEC reagent (Invitrogen). The cells were kept in serum-free and antibiotic-free conditions for 5 hours. Thereafter, the cells were kept under 10% FBS, 0.1% non-essential amino acids in DMEM (Cellgro). After 48 hours cells were lysed using passive lysis buffer from the DUAL LUCIFERASE kit (Promega). The DUAL LUCIFERASE assay was performed as per kit instructions.

Figure 3A:
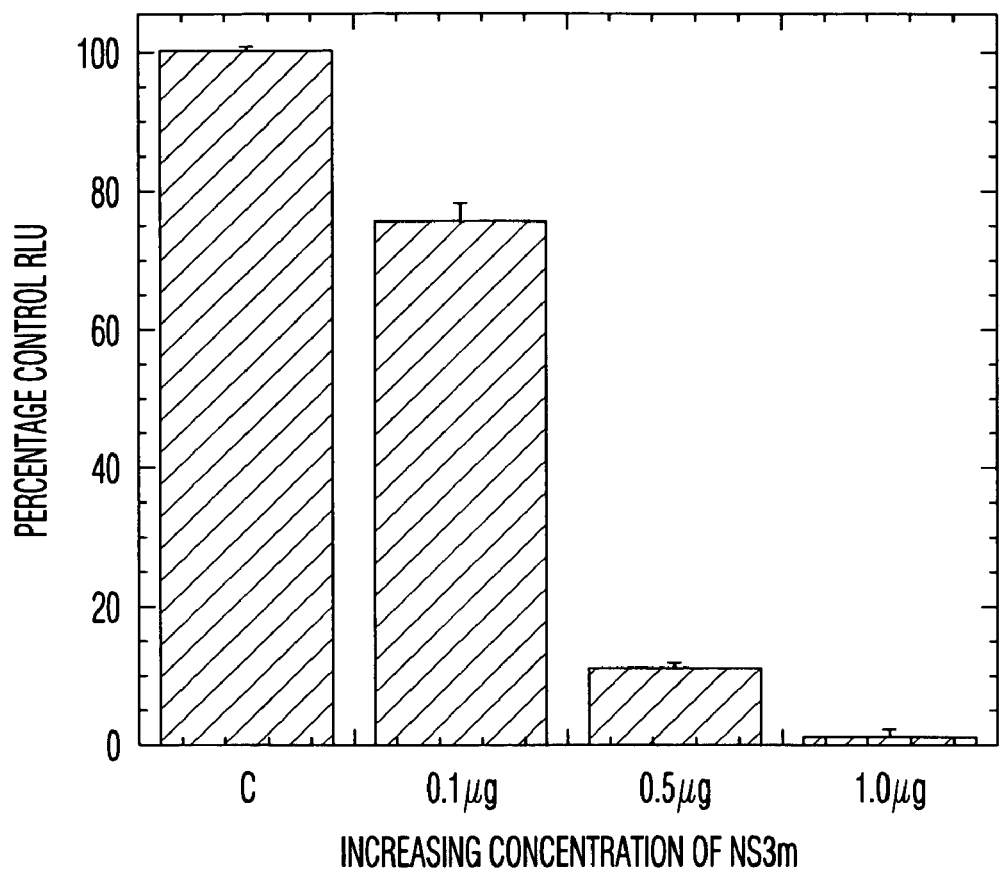
FIG. 3A is a plot of luciferase activity in cells transformed with HCV-Luc and increasing concentrations of plasmid expressing mutant NS3.
Figure 3B:
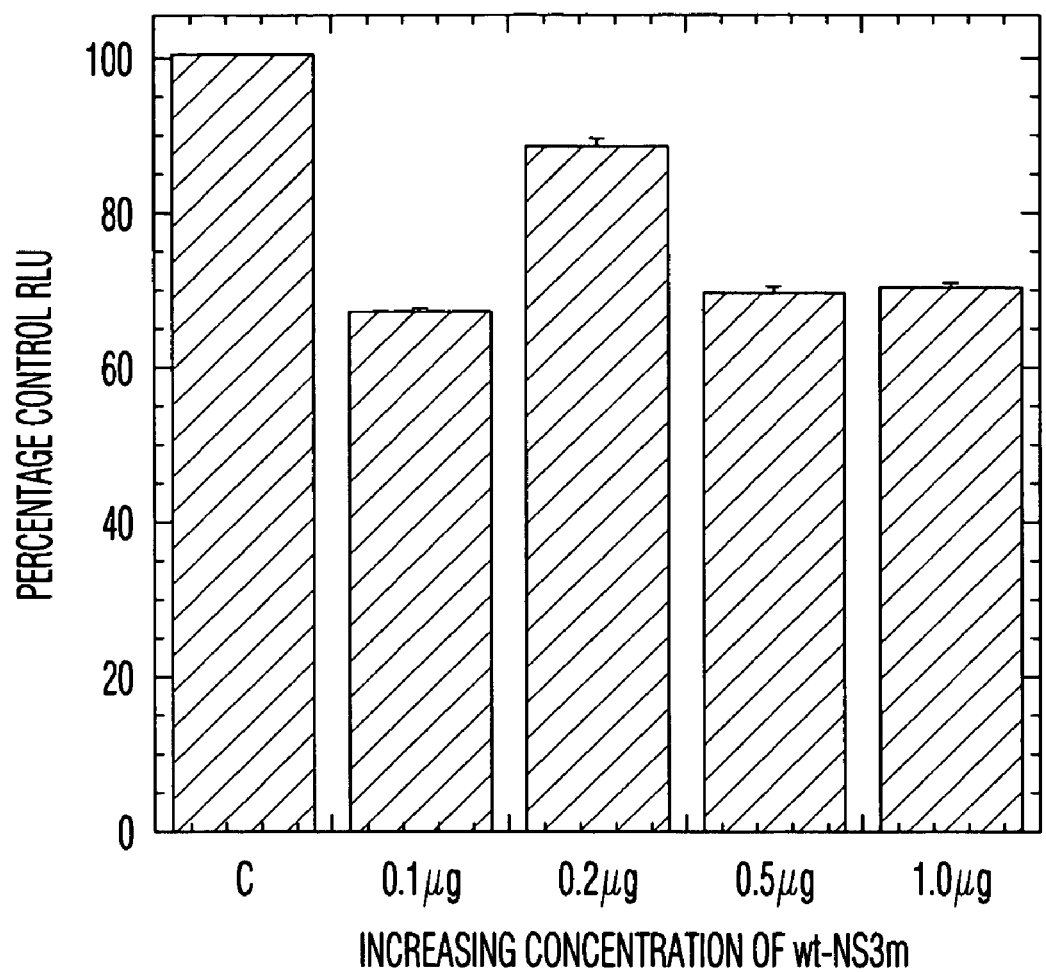
FIG. 3B is a plot of luciferase activity in cells transformed with HCV-Luc and increasing concentrations of plasmid expressing wild-type NS3.

There is a 9-fold reduction in activity of the replicon on addition of 0.5 µg of pmNS3 (FIG. 3A), while there is no appreciable reduction in the activity of the replicon on addition of exogenous wild-type NS3 (FIG. 3B)

Exogenous wt-NS3 is unable to rescue the activity of the mutant replicon: Huh-7 cells were transfected with HCV-Luc replicon encoding the ATPase-deficient mutant NS3 along with increasing concentration of wtNS3 plasmid and the *renilla* luciferase plasmid for transfection efficiency control. The cells were treated in conditions identical to those used in FIG. 3 and lysed using Promega's passive lysis buffer followed by luciferase assays at 48 hours.

Figure 4:
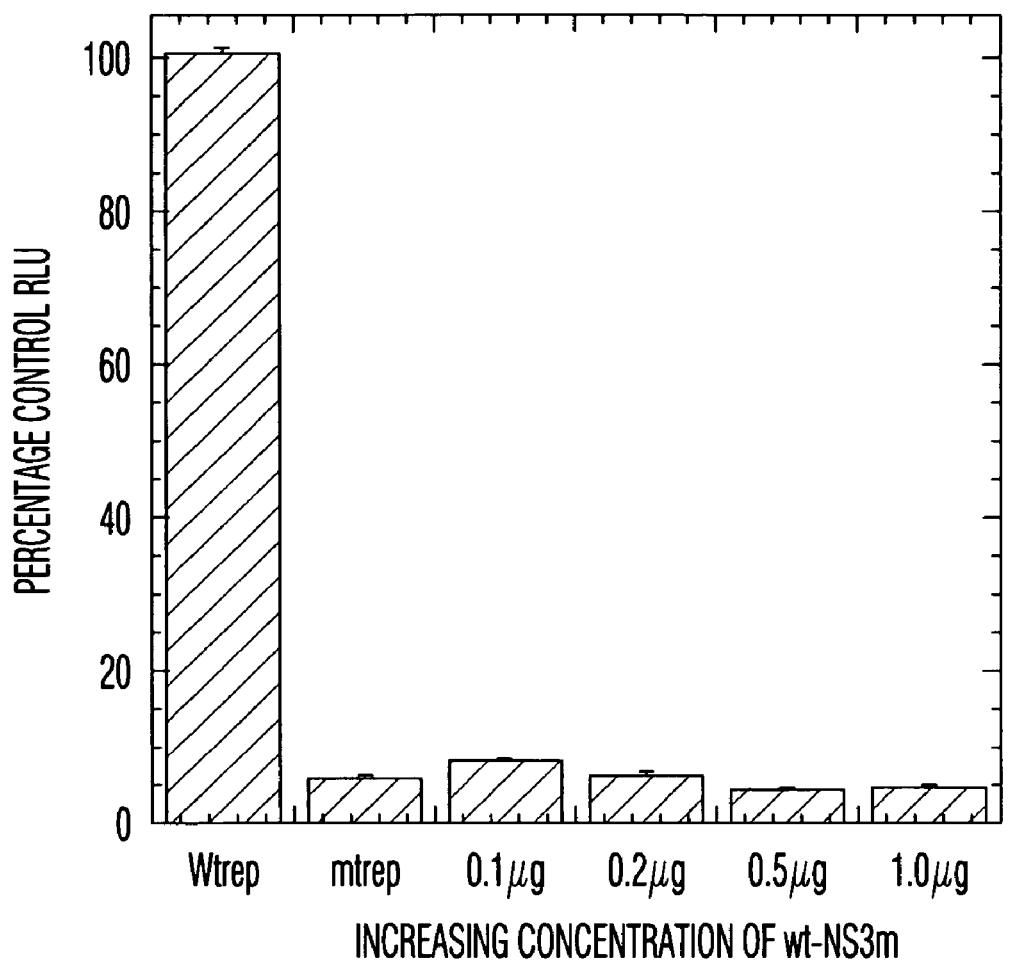

Co-transfection of increasing concentration of pwtNS3 plasmid along with mutant replicon did not change the activity of the replicon (FIG. 4).

Results of colony formation assay corroborate the effect seen using HCV-Luc replicon: Huh-7 cells stably transfected by S2204I replicon, which encodes an adaptive mutation allowing continuous replication in cells under G418 selection pressure, were transfected with increasing concentration of wtNS3 or mutant NS3 plasmids and plated onto 100 mm dishes at 1 million cells per dish. After 24 hours antibiotic-free lipofection media was replaced with DMEM with 10% FBS and G418 (500 µg/ml) for selection. The colonies were allowed to form over a period of 21 days. At the end of 21 days the plates were washed with PBS followed by staining with 0.1% crystal violet.

Figure 5:
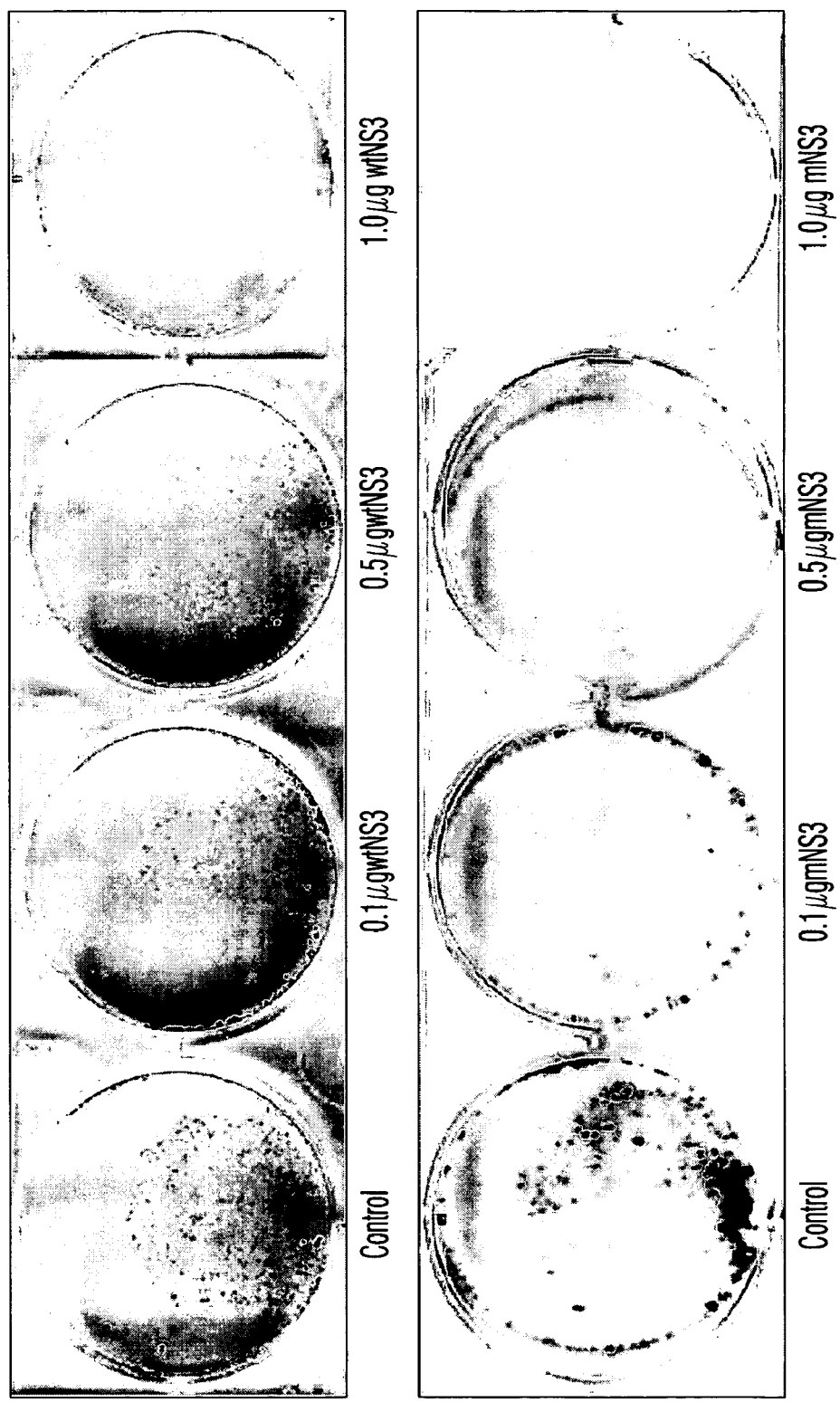
FIG. 5 shows plates of Huh-7 cells transformed with HCV S2204I replicon and varying concentrations of wild-type or mutant NS3 plasmid, and grown under G418 selection pressure and stained with crystal violet.

FIG. 5 shows the plates. Colony counts are in parentheses. The plates with addition of mNS3 plasmid showed a marked reduction in the number of colonies formed while the plates containing wtNS3 showed no significant difference in the number of colonies formed (FIG. 5). Therefore, we concluded that the ATPase-deficient form of NS3 inhibits the activity of the replicon in Huh-7 cells.

The dominant negative effect does not show up upon trans-complementation of wild-type replicon with mutant replicon: Huh-7 cells were plated in a 12-well plate at 70-80% confluency. Cells were transfected with the replicon (HCV-Luc) RNA with *renilla* luciferase plasmid (internal control) and increasing concentrations of D290A NS3 mutant replicon, using DMRIEC reagent (Invitrogen). The cells were kept in serum-free and antibiotic-free conditions for 5 hours. Thereafter, the cells were kept under 10% FBS, 0.1% non-essential amino acids in DMEM (Cellgro). After 48 hours cells were lysed using passive lysis buffer from DUAL LUCIFERASE kit (Promega). The DUAL LUCIFERASE assay was performed as per kit instructions.

Figure 6:
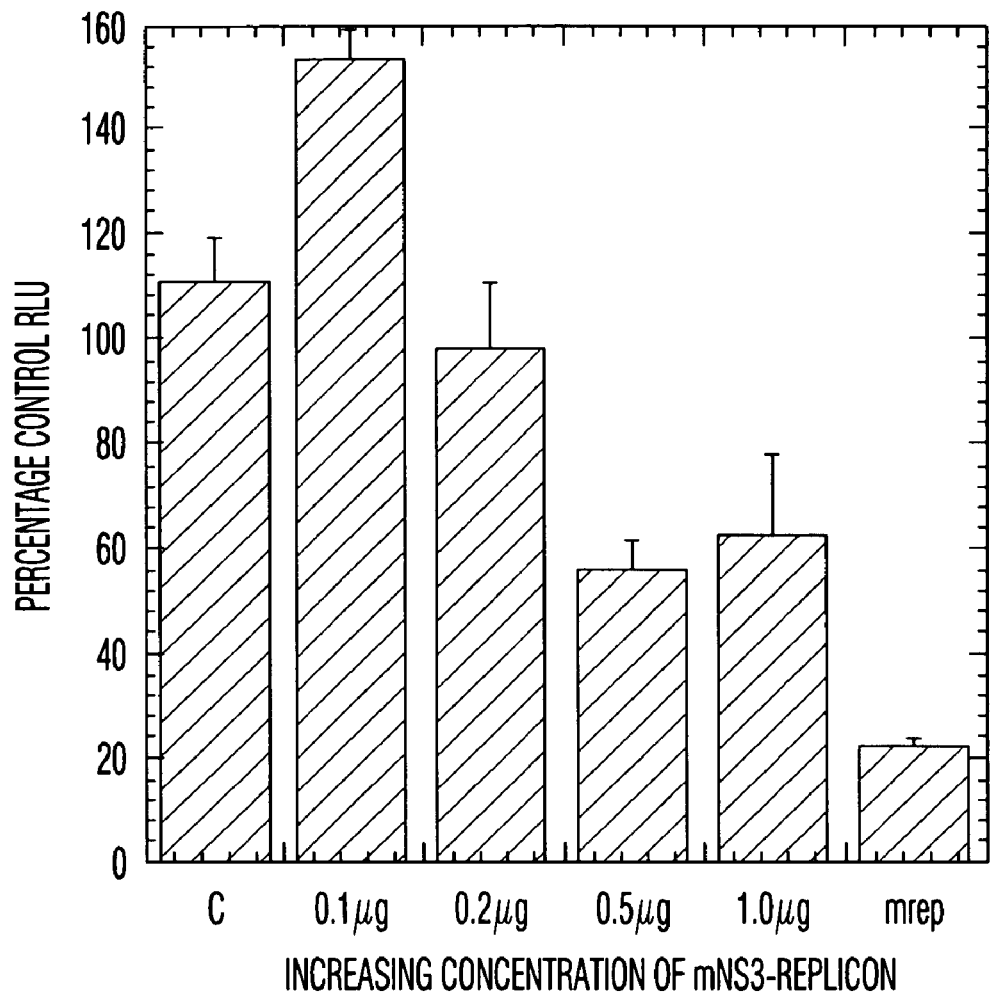
FIG. 6 is a plot showing luciferase activity of cells transfected with wt HCV-Luc replicon and increasing concentrations of mutant NS3 HCV-Luc replicon, or only the mutant replicon (mrep).

Upon co-transfection of cells with wild-type replicon (0.2 µg/well) and increasing concentration of mutant replicon we did not observe an appreciable effect on the activity of wt-replicon (FIG. 6). This led us to conclude that the dominant negative effect observed in the case of mutant NS3 does not occur at the polyprotein level.

Figure 7:
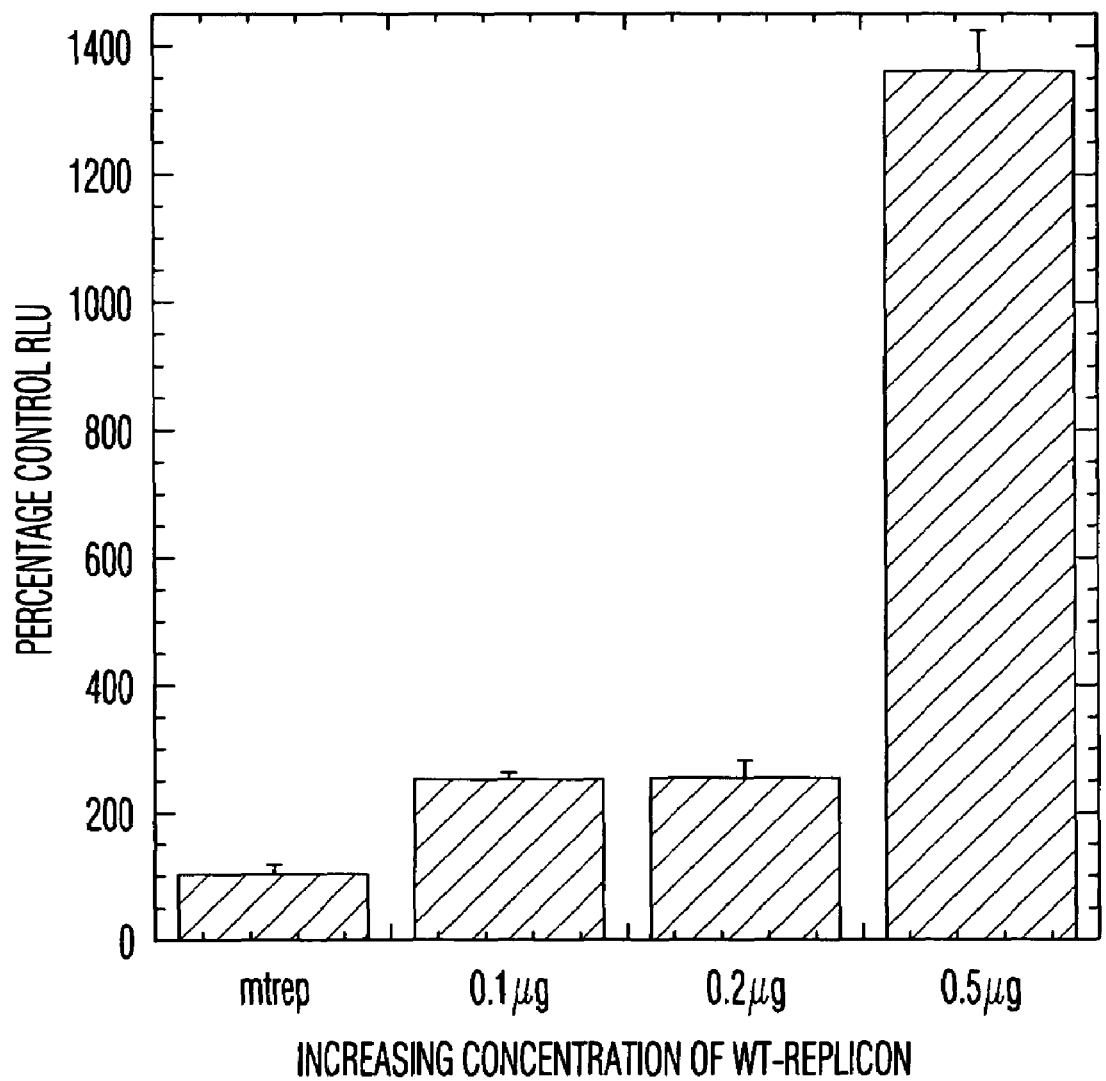
FIG. 7 is a plot of luciferase activity of Huh-7 cells transfected with mutant NS3 HCV-Luc replicon (mtrep) and increasing concentrations of wt HCV-Luc replicon.

Next, the conditions were reversed. Cells were transfected with the mutant replicon (0.2 µg/well) and increasing concentrations of wild-type replicon. Addition of increasing concentration of wt-replicon to the mutant replicon yielded an additive effect in replicon assays (FIG. 7). This also indicates that the dominant negative effect of mutant NS3 does not occur at the polyprotein level.

Discussion:

Previous studies have shown that the helicase domain of NS3 alone is viable as an oligomer but the oligomer is unstable (16). Also, there is evidence for subunit exchange and mixed oligomers of NS3 (16). However, the previous biochemical studies have been conducted under single-turn-over conditions, under which the concentration of the enzyme is higher than the concentration of the nucleic acid substrate.

The aim of this Example was to establish the effect of NS3 on hepatitis C virus in vivo. It has previously been shown that NS3 is required for replication of the virus (8). We decided to use the HCV replicon containing a luciferase gene (19, 26) as the model system to study the effect of exogenous ATPase-deficient mutant NS3 on the replication of HCV in vivo. Earlier studies have shown that the HCV replicon system is an excellent representation of HCV replication after infection. Two assays have been used to measure replication potential of the replicon: colony formation and luciferase activity. The two measurements have been shown to give results consistent with each other (19). We tested the system by conducting a time course study on the HCV-Luc replicon in comparison with replicons incorporating mutations that are known to inhibit replication of the virus, namely the D290A mutation in NS3, which obliterates the ATPase activity of NS3 and the G317A, D318A, D319G triple mutation in NS5b, which renders it polymerase deficient (16, 17, 19). The results showed that at 48 hours post-transfection, the luciferase activity accurately reports replication of HCV or the absence of replication (FIG. 1).

We then proceeded to demonstrate that hepatitis C virus NS3 protein is expressed in our cell culture system by both the replicon and the plasmids (pmNS3 and pwtNS3) encoding the NS3 gene driven by a CMV promoter, through western blotting using an antibody specific to NS3 (FIG. 2). Once the system was in place we transfected increasing quantities of pmNS3 and pwtNS3 plasmids along with the replicon RNA and showed that the addition of exogenous ATPase-deficient NS3 under a mammalian expression promoter (pmNS3) is able to reduce replication, while an identical amount of pwtNS3 has very little effect on the luciferase activity of the replicon (FIG. 3). These data demonstrate that the cleaved NS3 proteins interact with each other to form an active oligomer.

Independent confirmation of the results of the replicon assay was obtained by performing a colony formation assay. These data substantiated the finding that mNS3 functions in a dominant negative manner and is able to inhibit replication of the replicon, as evidenced by the reduction in number of colonies formed as a factor of increasing pmNS3 concentration (FIG. 5). As a control we showed that the addition of pwtNS3 in an identical manner did not alter the number of colonies formed as compared to the untransfected cells (FIG. 5).

It has been shown that HCV RNA translates into a polyprotein which is subsequently cleaved by proteases to yield mature independent proteins. To investigate the effect of expressing mutant polyprotein as opposed to mutant NS3 single protein, we performed trans-complementation assays in which we added increasing quantities of a replicon encoding an ATPase-deficient mutant NS3 to the wild-type HCV-Luc replicon. We found no effect with the addition of increasing concentration of the mutated replicon to the wt-HCV-Luc replicon (FIG. 6). Therefore, the mutant polyprotein does not have an effect on the replicative potential of the wild-type replicon, showing that mNS3 protein is interacting with the cleaved proteins and not the polyprotein to inhibit replication of the virus. It is also possible that the quantity of mutant NS3 protein produced by the replicon is insufficient to elicit the same response as when the protein is expressed from a plasmid. The addition of wild-type luciferase replicon has an additive effect on the activity of the replicon encoding the ATPase-deficient mutant NS3 (FIG. 7). That indicates the translation of replicon RNA is not limiting in these experiments.

This dominant negative effect of NS3 provides for an alternative mechanism of neutralizing the hepatitis C virus—by intervention with NS3 oligomerization by targeting the HCV-infected liver with mNS3 DNA or mNS3 protein.

Example 2

Helper-Dependent Adenovirus Vector for Targeting Mutant NS3 Expression to Liver

This Example describes preparation of a helper-dependent adenovirus vector, coupled to asialoorosomucoid for targeting to liver (28, 29). Helper-dependent (HD) adenovirus vectors have minimal adenovirus sequences and give more stable expression of the foreign DNA in the mammalian target cells than first generation adenoviruses, which retain almost all of the native adenovirus DNA. To replicate, helper-dependent adenoviruses require helper adenoviruses to provide necessary functions in trans (28).

A helper-dependent adenovirus vector is created containing 500 bp of cis-acting adenovirus sequences necessary for vector DNA replication (ITRs and packaging sequences), the ATPase-deficient NS3 gene under the control of a SV40 promoter, 400 bp of adenovirus sequence from the right end of the virus and containing the E4 promoter but not coding sequence (29, p. 1004-05), and stuffer sequence to bring the final vector size to 28-36 kb, preferably 28-31 kb. Stuffer DNA may be, for instance, noncoding human DNA lacking repetitive elements (29)

The helper virus is a first generation adenovirus with the E1 region deleted and with the virus packaging signal flanked by loxP sites (28, 29). An example is the H14 helper virus (29). A stuffer sequence is inserted into the E3 region to render any E1+recombinants too large to be packaged (28). Following infection of 293Cre cells, the helper virus genome is rendered unpackageable by excision of the packaging signal by Cre-mediated site-specific recombination between the loxP sites.

Low-passage 293 and 293Cre4 cells are maintained in 150-mm dishes and split 1 to 2 or 1 to 3 when they reach 90% confluency. 293Cre4 cells are maintained under 0.4 mg/ml G418 selection (28).

The HD vector is amplified by transfecting 293Cre4 cells with the HD vector plasmid in $CaCl_2$. After a 6-16 hour incubation, the cells are washed with fresh medium and then infected with helper virus at a multiplicity of infection (MOI) of 5 pfu/cell.

Complete cytopathic effect (>90% of the cells rounded up and detached from the dish) is observed by about 48 hours postinfection. The cells are scraped into the medium at that time. DNA is extracted from one ml for analysis to monitor vector amplification. The remainder is stored at −70° C. after adding sucrose to 4% w/v.

After thawing, 0.4 ml of the lysate is used to coinfect a 60-mm dish of 90%-confluent 293 Cre4 cells with helper virus at an MOI of 1 pfu/cell.

After complete cytopathic effect at about 48 hours, the cells are scraped into the medium, DNA is extracted from 1 ml for analysis, and 0.4 ml of the remainder is used for another round of amplification by cotransfection with helper virus at 1 pfu helper virus/cell.

The vector titer is quantified with each passage to determine the optimal number of passages—the number of passages after which the increase in HD vector titer slows substantially or the number of passages after which the lysate contains the maximal amount of HD vector with a low amount of helper virus.

For large-scale preparation, 150-mm dishes of 90% confluent 293Cre4 cells (seeded 1-2 days previously in nonselective complete medium) are coinfected with 1 ml of lysate from the passage previous to the optimum passage, and with helper virus at an MOI of 1 pfu/cell. At complete cytopathic effect, about 48 hours postinfection, cells are scraped and harvested, and the cell suspension is extracted for purification of the HD vector.

HD vector can be further purified by centrifugation in a CsCl step gradient using 1.25, 1.35, and 1.5 g/ml CsCl solutions. The vector should settle at the interface between the 1.25 and 1.35 g/ml layers.

The number of HD particles per ml can be calculated as follows:

$(OD_{260})(\text{dilution factor})(1.1 \times 10^{12})(36)/(\text{size of vector in kb})$ Coupling HD Adenovirus Vector to Asialoorosomucoid for Targeting to Liver Cell Receptors (30, 31)

The HD vector particles isolated above are dialzyed against 150 mM NaCl, 20 mM Hepes-NaOH, pH 7.4. In 4 ml, 5 mg asialoorosomucoid (AsOR) and 1.2 mg poly-L-lysine is dissolved with 1.4×10¹¹ HD particles, with the pH adjusted to 7.4. EDC (1-ethyl-3-(3-dimethylaminopropyl)carbodiimide) is added to 1 mM final concentration. After incubation on ice for 4 hours, the conjugated adenovirus-PLL-AsOR is separated from unreacted reagents by centrifugation (150,000×g) for 18 hours on a CsCl gradient at a CsCl concentration of 1.35 g/ml.

The adenovirus-PLL-AsOR conjugate is used to deliver adenovirus with high-specificity to liver cells in vitro or in vivo, by contacting the liver cells with the adenovirus conjugate cells (e.g., by intravenous administration of the adenovirus) at approximately $10^3$ adenovirus particles per liver cell.

Example 3

Identification of Surface Residues of Hepatitis C Virus Helicase Required for Optimal Replication Introduction Hepatitis C virus (HCV) is a 9.6 kb positive, single-stranded RNA virus. Many aspects of the HCV replication mechanism remain unknown, but it appears that at least five of the viral non-structural proteins are required for replication (6). Several non-structural protein-protein interactions have been identified (35, 36), and co-localization of non-structural proteins, including helicase (NS3) and polymerase (NS5B), on membrane structures within cells has been observed (37, 38), indicating formation of a multi-protein replication complex containing both polymerase and helicase enzymes. Understanding the mechanism of nucleic acid unwinding by NS3 is therefore a key step in characterizing the viral replication mechanism.

NS3 helicase (NS3h) has been expressed and purified independently of NS3 protease in a recombinant bacterial system and retains its in vitro unwinding activity (39). The NS3h structure consists of three distinct domains, with domains 1 and 2 containing all of the conserved motifs common to superfamily II helicase enzymes, including the DExH/D box motif (40, 41). ATP binds at the interface between domains 1 and 2, and nucleic acid binds within a cleft formed at the interface between domain 3 and domains 1 and 2 (41). Interactions between the protein and nucleic acid are not sequence-specific and primarily involve the phosphate backbone of the nucleic acid.

Despite extensive structural and biochemical characterization, the oligomeric state of the functional species of NS3 has not been determined conclusively. Biochemical studies have resulted in reports of monomeric (42), dimeric (43, 44), and oligomeric (16, 45) forms of the protein. Crystal structures of NS3h (40), NS3h bound to an 8-mer poly-dU substrate (41), and a full-length NS3/NS4A fusion protein (46) demonstrate that a single protein monomer can form crystals. However, none of these structures includes a substrate molecule of sufficient length to accommodate binding of multiple NS3h monomers. Crosslinking experiments indicate that NS3h can form oligomeric structures in solution (16). DNA unwinding activity of full-length NS3 is optimal at concentrations high enough to allow binding of multiple NS3h monomers to each nucleic acid molecule (unpublished data). However, no cooperative effect has been observed in binding studies (48), leaving open the possibility that NS3 is a non-processive monomer. A recently reported biochemical model suggests that monomeric NS3h is functional, but that multiple NS3h molecules are required for optimal processivity (49).

We have crystallized NS3h bound to a 16-mer poly-dU nucleic acid. The structure shows two NS3h molecules bound to a single DNA molecule and reveals an apparent interface between the two protein molecules. A mutational analysis of the protein interface region was performed in order to determine its importance for helicase activity and viral replication. We have identified several amino acid residues within this region that when mutated, result in reduced viral replication as measured in an HCV sub-genomic replicon. The biochemical activities of one of the mutant proteins are consistent with the dimeric structure in the x-ray crystal structure. However, the overall results from nucleic acid binding and helicase unwinding activity in vitro do not correlate with the biological results. These data indicate that NS3 helicase is likely to exhibit biological functions that are not reflected in the known biochemical activities.

Materials and Methods

Purification of NS3h

NS3h was purified according to published procedures (20).

Crystallization and Structural Determination of NS3h

Purified NS3h was concentrated to 32.2 mg/ml for crystallization. Examination of sample purity and determination of molecular weight were performed using SDS-PAGE on a PHAST GEL system (AP Biotech, NJ). The apparent molecular weight of the helicase was approximately 50 kDa. The $(dU)_{16}$ oligonucleotide was synthesized using an Expedite Nucleic Acid Synthesis System and purified by polyacrylamide gel electrophoresis to a final concentration of 4.6 mg/ml. Immediately before crystallization, NS3h was mixed with the $(dU)_{16}$ oligonucleotide at a 2:1 molar ratio. Crystals of diffraction quality were obtained by using the hanging drop method at room temperature with 4 μl of the mixture and 1 μl of reservoir solution (2.4 M $(NH_4)_2SO_4$, 0.1 M Tris hydrochloride, pH 8.5). Diffraction data were collected at 1.5418 Å by using a single crystal of 0.2 mm×0.4 mm×0.1 mm mounted in a thin-walled glass capillary at room temperature. The X-ray radiation was produced by an in-house Rigaku RU-H3RHB generator and focused by Osmic's Gutman multilayer mirrors (Woodland, Tex.). The diffraction pattern was recorded on the R-AXIS IV phosphor image plate detector. The diffraction data were reduced, integrated, and scaled with Denzo/Scalepack. Molecular replacement analysis was performed using AMORE software (49b), and structure refinements and model building/adjustment were done using CNS (50) and XTALVIEW (51) respectively.

The scaled data of resolution 3.3 Å indicated that the NS3h/$(dU)_{16}$ crystal belongs to the orthorhombic space group (Table 1). Space group assignment between $P2_12_12$ and $P2_12_12_1$ could not be made due to the absence of some (001) reflections. Matthews' Coefficient suggested the number of protein molecules in one asymmetric unit (ASU) could be 3 or 4, with solvent content being 67% or 50%, respectively.

TABLE 1

Data Collection and Refinement Statistics

| | |
|---|---|
| Data Collection | |
| Unit Cell | α = β = γ = 90° |
| A (Å) | 108.3 |
| B (Å) | 109.8 |
| C (Å) | 183.4 |
| Space group | $P2_12_12_1$ |
| Wavelength (Å) | 1.5418 |
| Resolution (Å) | 3.3 |
| Unique reflections | 33594 |
| Completeness (%) | 91.1 |

TABLE 1-continued

Data Collection and Refinement Statistics

| | |
|---|---|
| $R_{sym}{}^a$ (%) | 0.34 |
| <I/σ(I)> | 4.4 |
| Refinement | |
| Resolution (Å) | 30-3.3 |
| No. reflections[b] | 27936 (1673) |
| $R^{b,c}$(%) | 24.8 (27.4) |
| Avg. B-factors (Å) | 34.25 |
| Rmsd bond lengths (Å) | 0.010 |
| Rmsd bong angles (°) | 1.495 |

[a]$R_{sym} = \Sigma| I - <I> |/\Sigma I$; I, intensity.
[b]Value for $R_{free}$ set containing 5% of randomly chosen reflections.
[c]$R = \Sigma| F_{obs} - F_{calc} |/\Sigma F_{obs}$.

We completed the structure determination by molecular replacement (MR) using the published 1A1V structure (41) as an initial model. The 1A1V structure consists of an NS3h monomer bound to a $(dU)_8$ oligonucleotide. Prior to MR, the oligonucleotide was removed from the model. The MR results from space group $P2_12_12$ did not display any reasonable correlation among the individual solutions; however, the MR solutions in space group $P2_12_12_1$ showed strong correlation as well as realistic crystal packing (not shown).

A composite omit map was calculated using CNS (50) to identify any missing components. The resulting electron density map showed clearly the presence of the oligonucleotide at the nucleic acid binding sites of the protein molecules. The $(dU)_x$ fragments were inserted manually into the structure using XTALVIEW (51). The Maximum-Likelihood from Structure Factors (MLF) refinement on the model was done in CNS and is presented in Table 1.

Construction of Mutant Plasmids

Mutations were introduced into a pUC18-NS3 subclone containing nucleotides 1182-4918 from the HCV replicon sequence using the QUIKCHANGE Site-Directed Mutagenesis Kit (Stratagene). Mutant plasmids were transformed into SURE cells and purified from cultured cells with the QIAPREP Spin Miniprep Kit (QIAGEN). Mutant subcloned HCV sequences were then transferred into the replicon plasmid by digestion at Pme I and Mlu I restriction sites followed by ligation. Mutant NS3 sequences were transferred to pET26b-Ub expression plasmid by PCR followed by digestion at Sac II and EcoR I restriction sites and ligation. Quality of all final plasmid products was confirmed by sequencing.

Replicon RNA Synthesis

DNA template was prepared by digestion of replicon plasmid (10 μg) with Sca I restriction endonuclease at 37° C. for 4 hours. Complete linearization of plasmid was confirmed by agarose gel electrophoresis. RNA was synthesized in vitro by incubating 0.5 μg linear DNA template with 0.5 μg T7 RNA polymerase in 350 mM HEPES pH=7.5, 32 mM magnesium acetate, 40 mM DTT, 2 mM spermidine, and 28 mM NTPs at 37° C. for 3 hours. Template DNA was removed by incubation with 2 units Dnase I at 37° C. for 30 min. RNA was precipitated overnight in LiCl at −20° C. RNA purity and quality were verified by agarose gel electrophoresis.

Colony Formation Assays

HCV replicon RNA (1 μg) and Huh-7.5 cells ($2 \times 10^6$) were incubated with DMRIE-C lipofection reagent in serum-free medium at 37° C. for 60 min with gentle agitation. Transfected cells were centrifuged at 4000 rpm for 4 min, resuspended in 7.5 ml medium+10% fetal bovine serum, and transferred to a 10 cm culture plate. 0.5 mg/ml G418 was added 24 hours after transfection. Colony formation was monitored over a period of two to three weeks with replacement of growth medium every two days. Mature colonies were stained with 0.1% crystal violet.

Western Analysis

Huh-7.5 cells were transiently transfected with HCV RNA with TRANSMESSENGER Lipofectin Reagent (Qiagen) according to the manufacturer's instructions. Cells were lysed at 4 hours post-transfection in SDS-PAGE denaturing sample buffer. Lysate from $5 \times 10^5$ cells from each transfection was run on 10% SDS gel. Proteins were transferred from gel to PVDF membrane using a BioRad electrophoretic transfer cell at 100 V for 1 hour at 4° C. in transfer buffer (25 mM Tris, 192 mM glycine). Membranes were blocked in 5% dry milk/TBST for 1 hour, then washed three times for 5 min with TBST. Blocked membranes were exposed to rabbit polyclonal anti-NS3 (supplied by C.E.C.) in 5% BSA/TBST for 90 min, washed as described above, then exposed to HRP-conjugated goat anti-rabbit IgG (PerkinElmer) in 5% dry milk/TBST for 1 hour. Chemiluminescent detection was done by ECL western blotting analysis system (Amersham).

RNA Binding Assays

Varying concentrations of NS3h were incubated with 500 pM 5'-fluorescein-labeled $rU_{20}$ (Integrated DNA Technologies) in 50 mM MOPS-K+(pH 7.0), 10 mM NaCl, 50 μM EDTA, 0.1 mg/ml BSA for 5 minutes at 37° C. Binding was measured as a function of fluorescence polarization using a Beacon fluorescence polarization system. Data were fit to a hyperbola using Kaleidagraph software.

ATPase Assays

NS3h was incubated with 5 mM ATP in 50 mM HEPES (pH=7.5), 5 mM EDTA, 10 mM $MgCl_2$, 10 mM NaCl, 0.1 mg/ml BSA, 4 mM phosphoenolpyruvate, 10 U/ml pyruvate kinase/lactate dehydrogenase, and 0.7 mg/ml NADH. Absorbance of NADH at 380 nm was measured at 1 sec intervals for a period of 30 sec in the presence of the indicated concentrations of poly-U. Hydrolysis rates were calculated using an extinction coefficient of 1,210 $M^{-1}$ $cm^{-1}$ for NADH. Data were fit to a hyperbola using Kaleidagraph software.

Steady State DNA Unwinding Assays

The substrate used was a 45-mer/30-mer containing 30 base pairs of double-stranded DNA with a 15 base 3' single-stranded overhang. One strand was radiolabeled by incubation with $\gamma$-$^{32}$P-ATP and T4 polynucleotide kinase at 37° C. for 60 min. Unincorporated ATP was removed by SEPHADEX G-25 filtration. Equimolar amounts of labeled and complementary unlabeled strands were combined, heated to 95° C. for 10 min, and cooled slowly to room temperature to generate the final substrate. For steady state unwinding experiments, 100 nM NS3h was incubated with 250 nM substrate in 25 mM HEPES (pH=7.5), 0.5 mM EDTA, 10 mM $MgCl_2$, 10 mM NaCl, 0.1 mg/ml BSA. Reactions were initiated by addition of 5 mM ATP. Aliquots were taken at specific time points and the reaction was quenched by addition of 200 mM EDTA, 0.7% SDS. Substrate and product were separated by native polyacrylamide gel electrophoresis and detected and quantified by phosphorimaging analysis.

ATP-Independent DNA Unwinding Assays

NS3h or NS3h mutant enzymes (500 nM) were mixed with 2 nM DNA substrate (described in steady state section) in 25 mM MOPS (pH 7.0), 10 mM NaCl, 0.1 mM EDTA (pH 8.0), 2 mM βME, and 0.1 mg/mL BSA at 37° C. Aliquots were transferred to a 'quench solution' containing 200 mM EDTA, 0.7% SDS, 5 mM ATP, 10 mM $MgCl_2$, 60 nM annealing trap, and 100 μM poly-dT protein trap. Double- and single-stranded DNA were resolved on a native 20% polyacrylamide gel. The radiolabeled substrate and product were detected using a PHOSPHORIMAGER (Molecular Dynamics, Sunnyvale, Calif.); quantitation was performed with IMAGEQUANT software. The ratio of single- to double-stranded DNA was determined and plotted as a function of time.

Single Turnover DNA Unwinding Assay

Unwinding assays were carried out using a Quench-Flow apparatus (RQF-3, KinTek Instruments, Austin, Tex.) with a two-step mixing protocol (49). Reactions were carried out in 25 mM MOPS (pH 7.0), 10 mM NaCl, 0.1 mM EDTA (pH 8.0), 2 mM βME, and 0.1 mg/mL BSA at 37° C.; all concentrations are post-mixing. NS3h (500 nM) was mixed with 2 nM DNA substrate (described in steady state section) for 10 seconds before adding 5 mM ATP, 10 mM $MgCl_2$, 60 nM annealing trap (complementary to the displaced strand), and 100 μM poly-dT protein trap. The reaction was quenched after 0.1-15 seconds by ejection into a tube containing 200 mM EDTA, 0.7% SDS. Double- and single-stranded DNA were resolved on a native 20% polyacrylamide gel. The radiolabeled substrate and product were detected using a PHOSPHORIMAGER (Molecular Dynamics, Sunnyvale, Calif.); quantitation was performed with IMAGEQUANT software. The ratio of single- to double-stranded DNA was determined and plotted as a function of time. Data were fit to Equation 1, using KALEIDAGRAPH (Synergy Software, Reading, Pa.). This equation describes a 5-step mechanism for DNA unwinding that is necessary to fit the substantial lag phase associated with unwinding of the substrate (49, 52, 53).

$$A\{1-[1+k_{obs}t+1/2\,(k_{obs}t)^2+1/6\,(k_{obs}t)^3+1/24(k_{obs}t)^4]\,e^{-k_{obs}t}\}$$  Eq. 1

Results

Crystallization and Structural Analysis of NS3h Bound to $(dU)_{16}$

The crystals of NS3h in the presence of $(dU)_{16}$ oligonucleotide belonged to space group $P2_12_12_1$ with unit cell dimensions a=108.3 Å, b=109.8 Å, and c=183.4 Å (Table 1). We determined the structure by the molecular replacement method (MR) using 1A1V.pdb (41) as an initial model, in which its $(dU)_8$ fragment was manually removed prior to the rotational function search. We identified three helicase molecules (chains A, B, and C) per asymmetric unit (ASU) in our structure, with two helicase molecules bound to a single (dU)$_{16}$ molecule. The final atomic model shows no major unfavorable steric interactions between the helicase molecules, and the crystal packing shows no conflicts between the protein molecules in adjacent ASUs. We found no apparent non-crystallographic symmetric operations among the three monomers in this helicase model, nor did we observe any dramatic differences among the monomers. All three helicase molecules retain the basic Y shape characteristic of previously reported structures, with minor conformational differences at the surface loop regions.

The atomic coordinates of the helicase molecules A, B, and C in the final atomic model are provided in Table 2.

Chains A and B of the complex are bound to a 13-nucleotide span of one $(dU)_{16}$ molecule, with chain B rotated 90 degrees relative to chain A. The binding mode of both chains is consistent with that of the 1A1V structure, with the binding cleft at the interface of domains 1 and 2 with domain 3 in each protein molecule. Chain C appears to be independent of the dimer-oligonucleotide complex. The nucleic acid binding cleft of chain C faces away from the dimer structure and is occupied by a second oligonucleotide molecule. Chain C does not have any evident structural or mechanistic relationship with the other two protein molecules, and there appear to be no suitable contacts between chains B and C to indicate a functional interaction between these two molecules.

To determine the degree of similarity between chains A and B, we superimposed the two using domain 1 (the NTPase domain) as an anchor (the backbone RMSD for residues 190-324 was 0.7 Å). We observed only minor conformational differences between the two chains in each of the three domains. However, it appears that the relative orientation of domain 2 with respect to the anchored domain 1 is slightly different between chains A and B with a small but detectable tilting angle resulting in a slight widening of the nucleic acid binding groove in chain B. This flexibility of domain 2 relative to domain 1 is consistent with the proposed ratchet mechanism for nucleic acid translocation (41). Domain 3 displays a small degree of rotation between chains A and B, but is otherwise similar.

To assess the relationship of the apparent dimer structure to that of the monomeric NS3/oligo complex (41), we independently aligned each of the two monomer structures (chains A and B) with the 1A1V structure (data not shown). Both chains of the dimer structure align well with 1A1V, with chain A being a slightly better fit than chain B (overall RMSD ~0.9 Å and ~1.3 Å, respectively). Aside from the slight widening of the groove between domains 2 and 3 in chain B of our structure, no significant structural differences exist between the structure of 1A1V and the structures of our A and B chains.

In the dimer structure, the oligonucleotide is bound to each NS3h molecule within the groove formed at the interface of domains 1 and 2 with domain 3. The DNA interactions with chain A are virtually identical to those observed in the 1A1V structure. In the region between chains A and B, the DNA appears to be bent by nearly 90 degrees. It is possible that this bend is stabilized by the apparent base stacking between nucleotides $dU_8$ and $dU_{10}$. However, the electron density in this region is weak, and although structure validation by WHAT_CHECK (54) suggested that the bent conformation of the DNA is allowable (55), we accept the possibility that the bend may indeed exist in another conformation. Comparisons of the 3' binding regions in both chains A and B to 1A1V exhibited high similarity in nucleotide binding, suggesting that the binding mode of the oligonucleotide between chains A and B is likely to exist as presented. The overall DNA binding mode with respect to chain B is similar to that with respect to chain A. However, due to the displacement of domain 2 in chain B, domains 2 and 3 are farther apart than in chain A. In turn, the binding groove of chain B is slightly wider and causes the oligonucleotide to tilt toward domain 2, allowing domain 1 and the oligonucleotide backbone to retain the same interactions observed in chain A. The domain displacement, however, does not dramatically alter the interactions of oligonucleotide with domains 1 and 3. For example, the Trp501 side chain retains its ring-to-ring stacking position, and Thr269 remains in position to allow hydrogen bonding with the phosphate backbone of the DNA at $dU_{11}$. The DNA fragment in chain B is pushed slightly out of the binding groove and shifted away from the α-helical domain. As a result, the electron density for this fragment is less clear than that in chain A.

There are numerous close interactions between chains A and B involving multiple sets of amino acid residues, including H545-A553 and C584-T591 of chain B, and T435-Q453, T477-S488, and V524-Q536 of chain A. In addition, Thr450 of chain A and Gln549 of chain B appear to be in position to allow hydrogen bond formation between the two monomers at the dimeric interface. Chain B residues 541-551 interact with a chain A cleft formed by residues 477-481 and 452-453.

To assess the strength of interaction between chains A and B, we calculated the extent of buried surface area ($S_{AB}$) at the interaction site using WHATIF molecular modeling software (55b). This value is defined as $S_{AB}=A_A+A_B-A_{AB}$, where A is the total surface area of the folded polypeptide molecule. The surface areas of chains A and B are 5883 Å$^2$ and 5839 Å$^2$, respectively. The total surface area calculated for the dimer is approximately 11279 Å$^2$, leaving a difference of 443 Å$^2$ buried at the interface. This area is not sufficient to support independent dimer formation in the absence of nucleic acid, which is consistent with the observed monomeric behavior of NS3h in size exclusion chromatography (Raney and C. Chen, unpublished observations).

Biological Analysis of Surface Residues

To assess the importance of the protein-protein interface region observed in the crystal structure, we performed a mutational analysis involving two clusters of residues (Asp543/His545/Gln549 and Arg587/Leu588/Lys589/Thr591) in domain 3. These residues are situated at the interface of the two NS3h molecules and appear to be of particular importance in the protein-protein interaction. We did not introduce mutations at the domain 2 interface site because of its proximity to the conserved helicase motifs. Amino acid residues 543-545 were deleted (Δ543-545), and two sets of substitution mutations (D543K/H545D/Q549A and R587D/L588D/K589D/T591D) were introduced independently into the HCV-neo-I377/NS3-3'UTR replicon (26) containing an S2204I adaptive mutation (56).

Figure 8:
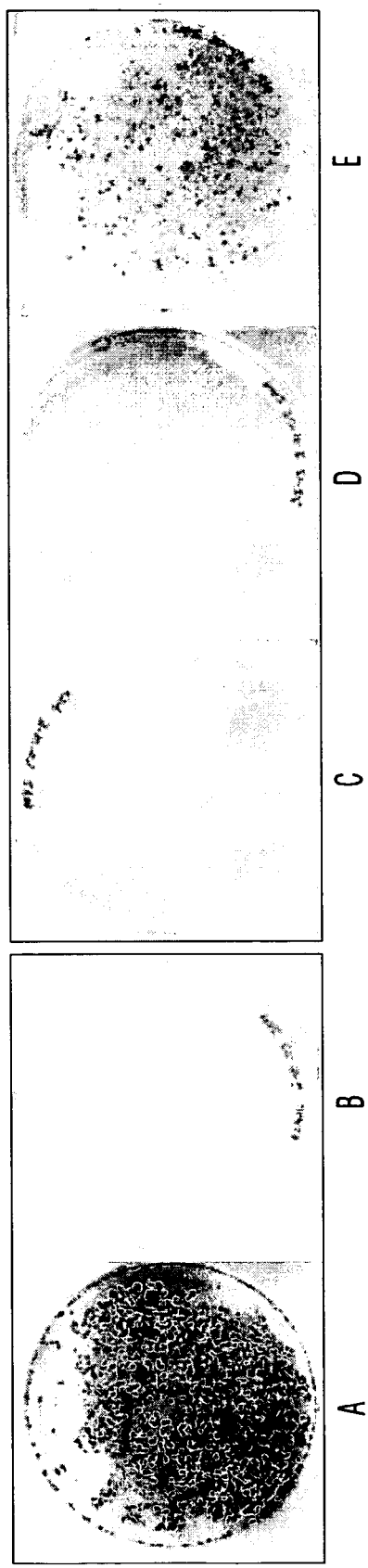
FIG. 8. Growth of Huh-7 cells after transfection with wild type and mutant forms of the HCV replicon. Colony formation of Huh-7 cells was monitored over a period of two weeks following transfection by HCV replicon RNA. Colonies were stained with 0.1% crystal violet. A) S22041 RNA. B) no RNA. C) Δ543-546 mutant RNA. D) D543K/H545D/Q549A mutant RNA. E) R587D/L588D/K589D/T591D mutant RNA.

We transfected Huh-7 human hepatoma cells with mutant HCV RNA, and monitored the cells for replication-dependent growth. Cells transfected with S2204I HCV RNA formed large, densely spaced colonies after two to three weeks of growth (FIG. 8A). Cells transfected with the mutant HCV RNA showed significantly reduced colony formation, indicating that the targeted NS3 surface region is important for efficient viral replication. The Δ543-545 and D543K/H545D/Q549A (NS3h KDA) mutants were of particular interest, as they supported very little cell growth (FIGS. 8C and D). Only pinpoint colonies were visible at two weeks post-transfection, and no cells remained at three weeks post-transfection. The R587D/L588D/K589D/T591D mutation (NS3h DDDD), at a different site within the protein interface than the Δ543-545 and NS3h KDA mutations, had a visible but less dramatic effect on growth (FIG. 8E). Colonies were less densely spaced than in the S2204I transfection, but those that formed grew to approximately the same size as wild type colonies.

Figure 9:
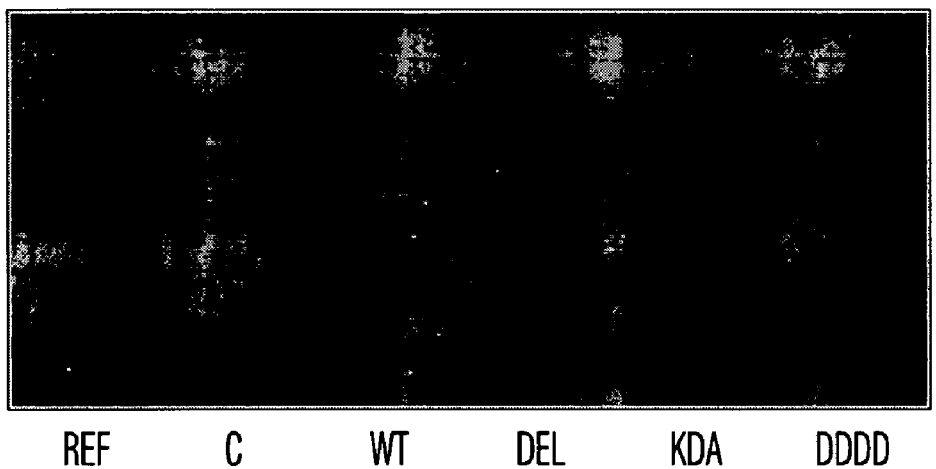
FIG. 9. Western analysis of HCV-trasfected Huh-7.5 cell lysates. $5 \times 10^5$ cells from each lysate were loaded on a 10% polyacrylamide gel. The gel was blotted onto a PVDF membrane and the blot was incubated with rabbit anti-NS3. Primary antibody binding was detected by chemiluminescence with HRP-conjugated anti-rabbit IgG. The lane marked "REF" is purified NS3h. The lane marked "C" is the control transfection with no HCV RNA.

We performed a western analysis with NS3 antibody on transfected cell lysates in order to determine whether NS3 protein expression was affected by any of the mutations (FIG. 9). The Δ543-545 mutant NS3 protein was present at significantly lower concentration than observed in S2204I transfected cells. However, no impairment of translation was observed for either of the two substitution mutants.

Biochemical Analysis of NS3h Mutants

Figure 10A:
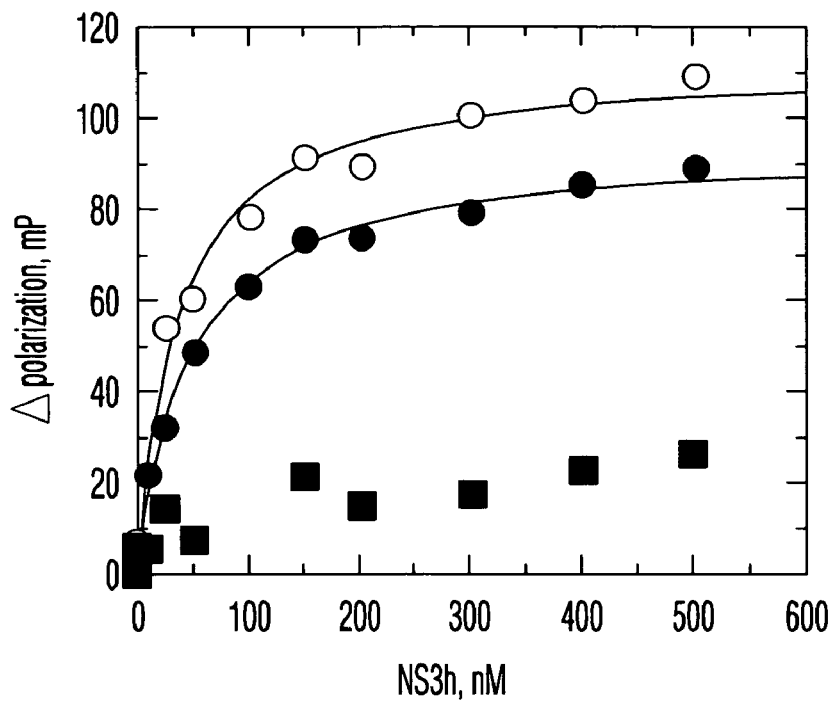
FIGS. 10A and B. Binding of mutant NS3h to fluorescein-labeled $U_{20}$ RNA (FIG. 10A) or $dT_{15}$ DNA (FIG. 10B). Nucleic acid binding was determined by measuring fluorescence polarization following incubation of protein and nucleic acid at 37° C. Data were fit to a hyperbola using Kaleidagraph software. (A) NS3h wild type (●) bound to RNA with a $K_D$ of 47±5 nM and NS3h KDA (○) bound to RNA with a $K_D$ of 38±4 nM. NS3h DDDD (■) did not bind with high enough affinity to determine a binding constant under these conditions. (B) Binding to the $dT_{15}$ by NS3h wild type (●) resulted in a $K_D$ of 5.9±1.4 nM whereas the NS3h KDA mutant (○) bound with a $K_D$ of 2.6±0.8 nM.
Figure 10B:
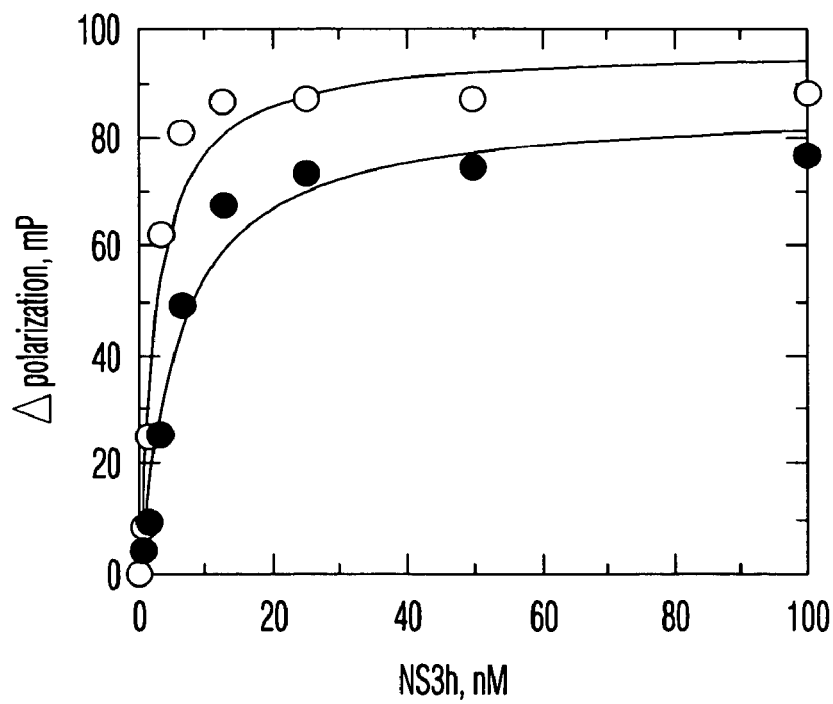
Figure 11:
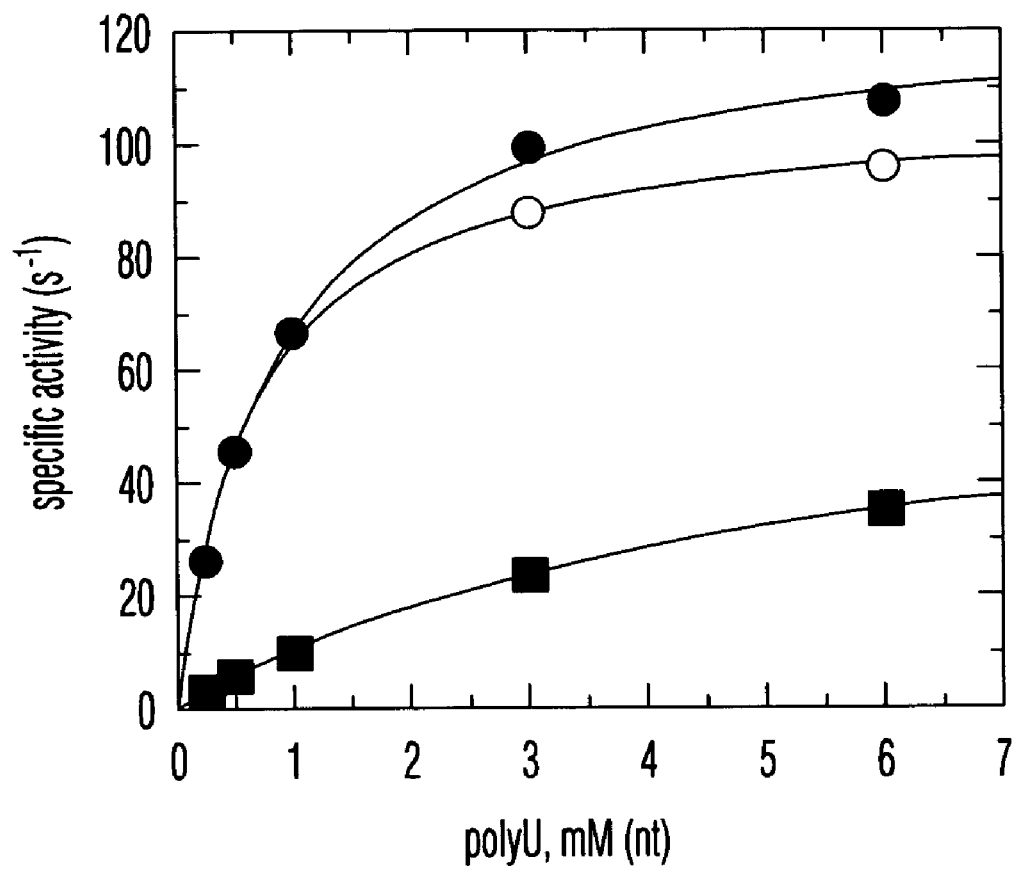
FIG. 11. ATPase activity of mutant NS3h was measured as a function of NADH concentration in a coupled assay at varying concentrations of polyU. Data were fit to a hyperbola using Kaleidagraph software. Specific activity of NS3h wild type (●) and NS3h KDA (○) were comparable at 126 s$^{-1}$ and 108 s⁻¹, respectively, in the presence of saturating polyU. Specific activity of NS3h DDDD (■) was lower.

In order to determine the effects of the surface mutations on the biochemical activities of NS3h, we over-expressed and purified NS3h KDA and NS3h DDDD in a prokaryotic expression system and compared the binding and enzymatic activities of the mutant NS3h proteins to those of wild type. We measured the RNA and DNA binding affinities of the mutant and wild type enzymes using fluorescein-labeled, oligonucleotide substrates (FIG. 10). The NS3h KDA mutation did not impair binding to RNA or DNA, but the NS3h DDDD mutation severely reduced binding affinity as measured by fluorescence polarization. Binding to the DNA oligonucleotide was around ten-fold tighter than to the RNA oligonucleotide. Poly-U stimulated ATP hydrolysis of the mutant and wild type enzymes was measured and no significant differences were observed between the activities of the wild type and NS3h KDA mutant (FIG. 1). The activity of the NS3h DDDD mutant was severely impaired, probably as a consequence of its reduced nucleic acid binding affinity.

Figure 12A:
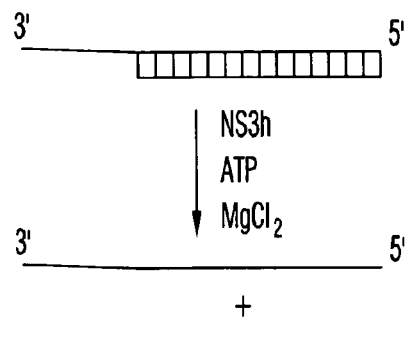
FIGS. 12A-C. Steady state unwinding activity of mutant versus wild type NS3h. A) The assay for measuring helicase unwinding activity is depicted. A partially duplexed substrate containing 30 bp and 15 nt of ss overhang (45:30mer) was incubated with NS3h in the presence of ATP and Mg$^{+2}$ leading to unwinding of the duplex. B) Comparison of unwinding of DNA and RNA substrates by NS3h. Otherwise identical 250 nM duplexed DNA and RNA substrates were incubated with 100 nM NS3h. Reactions were initiated by addition of 5 mM ATP and 10 mM MgCl$_2$ and quenched by addition of 200 mM EDTA/0.7% SDS. C) Unwinding of 250 nM substrate under steady state conditions. Unwinding by 100 nM NS3h (●), NS3h KDA (○), and NS3h DDDD (■) occurred at rates of 5.3 nM min⁻¹, 5.7 nM min⁻¹, and 4.1 nM min⁻¹, respectively.
Figure 12B:
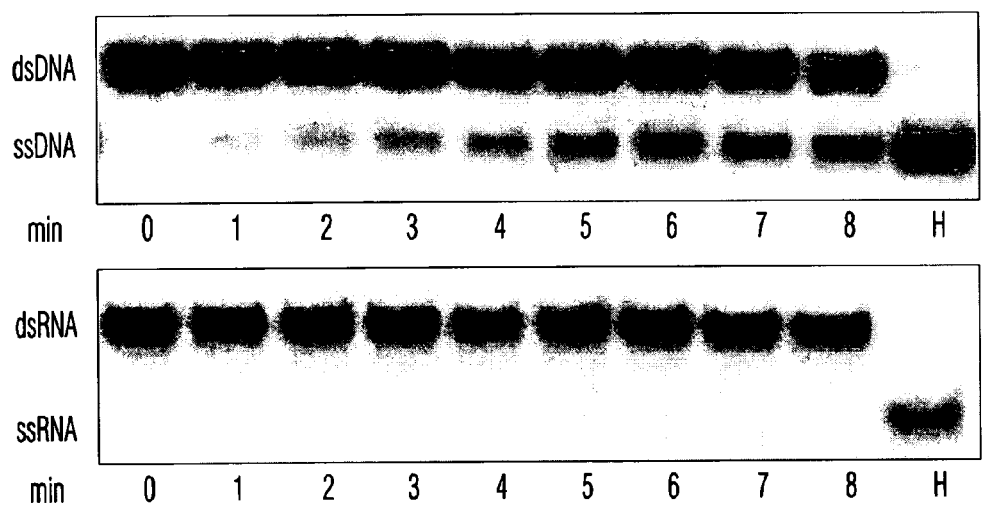
Figure 12C:
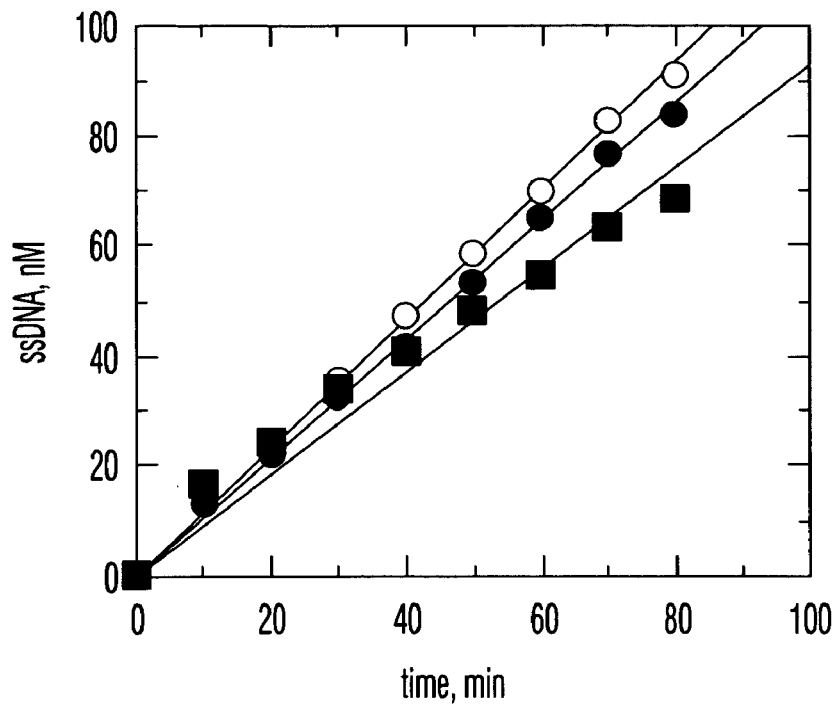
Figure 13:
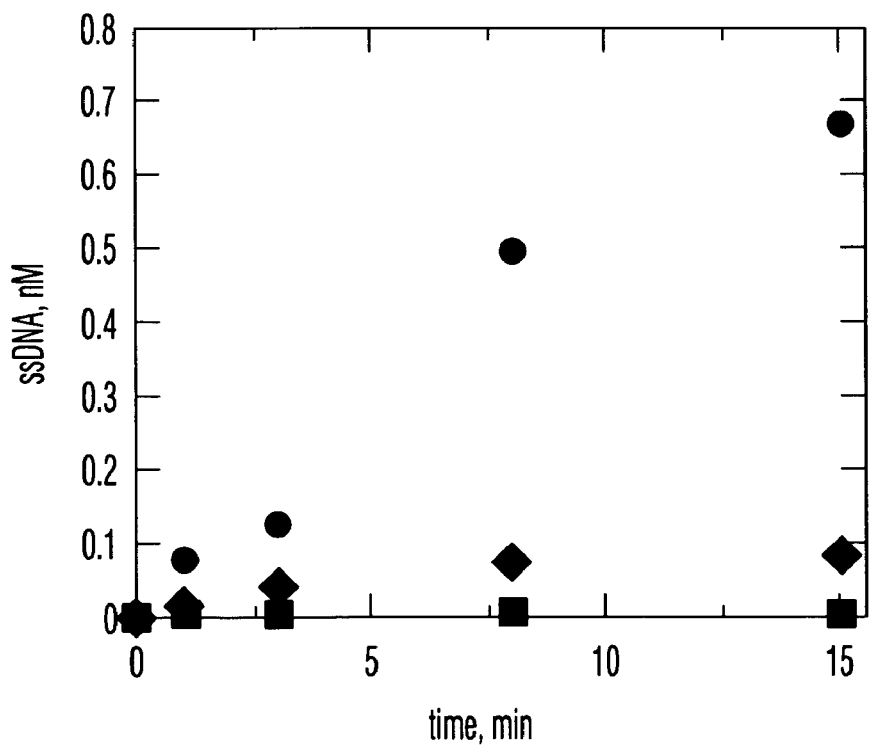
FIG. 13. Graph showing ATP-independent unwinding activity of NS3h wild-type, NS3h KDA, and NS3h DDDD. NS3h, 500 nM, was incubated with a partial duplex DNA substrate containing 15 nt of single stranded DNA and 30 base pairs at 37° C. Aliquots were quenched by addition of 100 μM poly dT and 60 nM of a 30mer oligonucleotide that served to prevent reannealing. ssDNA was separated from dsDNA by native polyacrylamide electrophoresis and the resulting fractions were quantified by using IMAGEQUANT software. DNA melting is shown for NS3h (●), NS3h KDA (♦), and NS3h DDDD (■).

Unwinding of nucleic acid was measured by using a standard helicase assay (FIG. 12A). A substrate (45:30mer) containing 30 base pairs with a 15 nt 3' single-stranded overhang was prepared by annealing appropriate oligonucleotides. We observed very little unwinding of an RNA substrate by NS3h, consistent with a recent report describing the lack of RNA unwinding activity of NS3h (FIG. 12B) (45). Therefore, we measured unwinding rates using a DNA substrate. NS3h and the two mutant enzymes unwound the 45:30mer DNA at approximately 1 nM/min under steady state conditions (FIG. 12C). The conditions used in this assay are likely to favor a monomeric form of NS3h because it is highly unlikely that two molecules bind to the same substrate molecule in the presence of a large excess of DNA. This observation further confirms that NS3h KDA monomer is not functionally impaired. NS3h DDDD unwinds DNA almost as well as NS3h wild type under steady state conditions, despite its reduced binding affinity for nucleic acid. Steady state unwinding rates reflect a number of possible steps in the reaction, including association, dissociation, and DNA unwinding, so it is not possible to state that NS3h DDDD unwinding is the same as the wild type NS3h based solely on this experiment. However, the result with NS3h DDDD does indicate that it can unwind the substrate.

The uncertainties associated with measuring unwinding under steady state conditions can be overcome by measuring unwinding under single turnover conditions in the presence of excess enzyme (43, 49). Initial attempts to perform single turnover experiments were hampered by substantial ATP-independent unwinding with wild type NS3h (data not shown), consistent with previous reports (57). To compare the ATP-independent unwinding activity of the mutant and wild type forms of NS3h, excess enzyme was incubated with substrate in the absence of ATP, and the reaction was stopped by addition of excess poly dT to trap the enzyme. Interestingly, NS3h exhibited much greater ATP-independent unwinding than NS3h KDA or NS3h DDDD (FIG. 13). This result may reflect reduced protein-protein interactions in the case of NS3h KDA, because the nucleic acid binding affinity of this mutant is the same as the wild type NS3h (FIG. 10).

Figure 14:
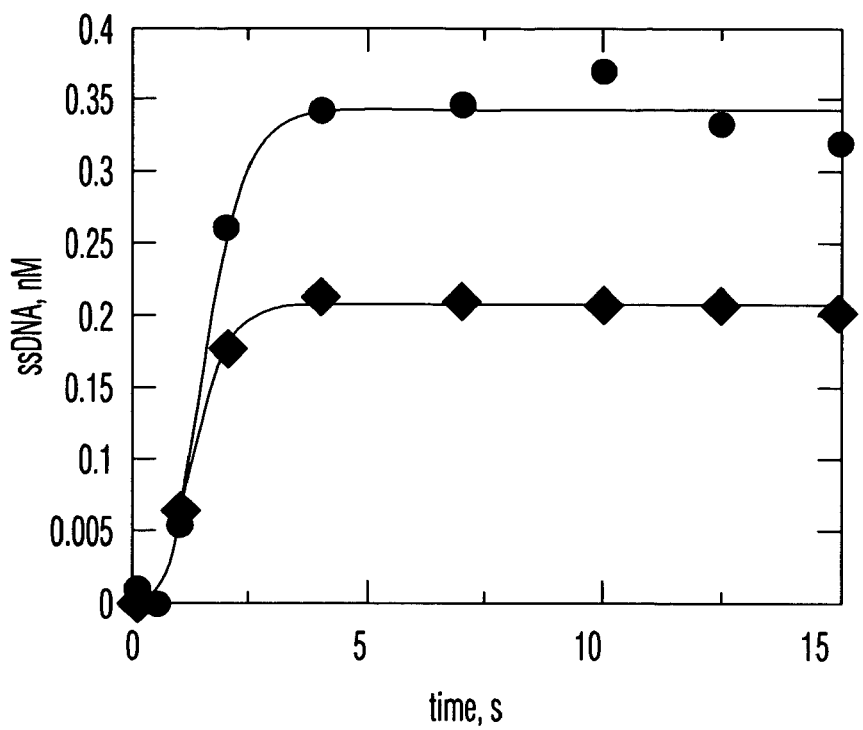
FIG. 14. Single turnover DNA unwinding by NS3h and NS3h mutant enzymes. A two-step mixing technique was used to measure single-turnover unwinding in the presence of excess NS3h. NS3h (500 nM) or mutant enzyme was rapidly mixed with substrate followed by a 10-second incubation. A second, rapid mixing step followed in which ATP, Mg$^{+2}$, and protein trap (poly dT) was added. Data were fit according to equation 1 resulting in unwinding rates of 3.1±0.1 s⁻¹ and 3.7±0.1 s−1 for NS3h (●) and NS3h KDA (♦), respectively. The amplitudes for unwinding were 0.35±0.01 nM and 0.21±0.01 nM for NS3h and NS3h KDA, respectively.

A different experimental protocol was required to measure the unwinding activity under single turnover conditions in the presence of excess enzyme due to the ATP-independent unwinding activity of NS3h. NS3h was rapidly mixed with substrate and incubated for a 10 s interval, followed by a second rapid mixing step in which ATP and Mg$^{+2}$ were introduced (FIG. 14). The initial 10 s incubation time was too short for ATP-independent unwinding to occur. The Kintek Chemical Quench-Flow instrument is designed to readily perform such a 'double-mixing' experiment which was recently used by Levin et al. to measure NS3h unwinding activity (49). Under these conditions, NS3h exhibited a lag phase very similar to that observed previously for a substrate of similar length (49). The lag phase represents multiple steps that are believed to occur prior to complete unwinding of the duplex (52, 53, 58). No unwinding was observed for NS3h DDDD under single turnover conditions (not shown). However, NS3h KDA unwound the substrate with a similar lag phase as the wild type enzyme, but significantly lower amplitude (FIG. 14). The amplitude for unwinding reflects the degree of processivity of the enzyme (49, 59); therefore NS3h KDA has lower processivity than NS3h.

Discussion

We describe here the first x-ray crystal structure of NS3 helicase bound to a DNA molecule of sufficient length to accommodate binding of two molecules of enzyme. Our structure shows a nucleic acid binding site for each monomer that is consistent with a published crystal structure of a single monomer bound to a shorter DNA molecule (41). In each case, the DNA binds to a cleft between domains 1 and 2 on one side and domain 3 on the other. DNA binding is non-sequence specific, with the majority of protein-DNA contacts involving the phosphate backbone. The structure also reveals a protein-protein interface between two DNA-bound helicase monomers. The protein-protein contacts are mostly hydrophobic and involve domain 2 of one subunit (chain A) and domain 3 of the second subunit (chain B). The two nucleic acid binding sites of the dimer are therefore aligned in such a way as to force a significant bend in the bound DNA that appears to induce a base stacking motif in the oligonucleotide.

The structure and function HCV helicase have been investigated extensively. Important amino acid sequence motifs that play critical roles in biochemical function have been identified on both domains 1 and 2. The function of domain 3 has been less well characterized, presumably due to the facts that in superfamily II helicases, domain 3 is less conserved compared to domains 1 and 2 and that among the helicase superfamilies, there is no apparent homology in domain 3 (60). In the structure reported here, surface regions on domain 3 interact with domain 2 of the second molecule. Biological studies demonstrate that mutations in these surface regions interfere with viral replication in cell culture. This indicates that, besides its critical role in substrate binding, domain 3 also plays a role in mediating the formation of protein-protein complexes between NS3 monomers or between NS3 and other protein partners to ensure viral survival and growth.

NS3h exhibits relatively weak protein-protein interactions whereas full-length NS3 appears to interact with itself much more strongly (Raney and Chen, in preparation), which may account for some of the differences in activities observed between the two forms of the enzyme. For example, NS3h unwound only 17% of the 45:30mer whereas full-length NS3 unwound greater than 80% of the same substrate under the same conditions (unpublished data). Therefore, NS3h exhibits lower processivity in DNA unwinding than the full-length protein, which may reflect the relative strength of protein-protein interactions. Monomeric helicases are generally associated with low processivity; meaning that these enzymes can unwind only a few base pairs prior to dissociating from the DNA. Moderately processive helicases such as hexameric helicase DnaB (58) are able to unwinding hundreds of base pairs prior to dissociating from the DNA, although the replicative helicases are much more processive when associated with the replication complex. One highly processive helicase, RecBCD, has two helicase motors, one for each DNA strand, which leads to very high processivity (61, 62). The Rep helicase reportedly is unable to unwind DNA as a monomer, but readily melts the duplex as a dimer (63). The mutations at the interface of the putative dimer were designed to disrupt protein-protein interactions. These mutations would not be expected to disrupt the biochemical activities of monomeric NS3h. Indeed, NS3h KDA exhibits activities that mirror the wild-type enzyme in terms of nucleic acid binding, ATPase activity, and steady state DNA unwinding. The only biochemical activities of NS3h KDA that are reduced are processivity and ATP-independent unwinding, each of which would be expected to rely more heavily on protein-protein interactions. Thus, enzymatic activities of NS3h KDA are consistent with the biochemical relevance of the dimeric structure reported here. However, the reduction in amplitude for unwinding under single turnover conditions is less than two-fold, which would seem unlikely to be responsible for the dramatic reduction in HCV replicative capacity exhibited with the NS3h KDA mutations. Hence, the biochemical results are not sufficient to explain the biological results. The results with NS3h DDDD emphasize this point. NS3h DDDD has much lower affinity for nucleic acid than wild-type NS3h, resulting in essentially no product formation under single turnover unwinding conditions. However, the replicative capacity of the HCV replicon containing the DDDD mutation is greater than the HCV replicon containing KDA mutation. Thus, the biochemical activities of NS3h do not appear to reflect all of the biological activities of this enzyme. It remains a strong possibility that the protein surface implicated in formation of a dimeric helicase in vitro mediates additional interactions in vivo that are required for formation of a multi-protein viral replication complex.

By solving the x-ray crystal structure of two molecules of NS3 helicase domain bound to the same oligonucleotide, we have identified a region on the surface of the HCV NS3 helicase that is required for efficient viral replication. The amino residues in this region are highly conserved amongst isolates of HCV. The surface region appears to be capable of mediating protein-protein interactions, but does not appear to be essential in the nucleic acid binding or known enzymatic activities of NS3h. These data illustrate that NS3 has additional biochemical activities and/or protein-protein interactions in vivo that are not revealed by the known biochemical assays.

Conclusions

The hepatitis C virus non-structural protein 3 is a multi-functional enzyme with serine protease and DExD/H-box helicase domains. The helicase domain was crystallized in the presence of a single-stranded oligonucleotide long enough to accommodate binding of two molecules of enzyme. Several amino acid residues at the interface of the two helicase molecules appear to mediate a protein-protein interaction between domains 2 and 3 of adjacent molecules. Mutations introduced into domain 3 to disrupt the interface dramatically reduced replication capacity in a subgenomic replicon system. Purified mutant helicase exhibited lower processivity during DNA unwinding, consistent with the outcome predicted by the x-ray crystal structure. However, the overall biochemical activities of the mutant enzyme do not reflect the large reduction in HCV replication capacity seen in the biological experiment. Hence, the surface residues identified here, in addition to being essential for NS3-NS3 interactions that increase NS3 helicase activity, are probably required for a biological function of the helicase domain unrelated to known biochemical activities.

Example 4

A Peptide Inhibitor of NS3-NS3 Interactions Inhibits Hepatitis C Virus Replication The data from the structural, biological, and biochemical data indicated the importance of domain 3 and in particular, the amino acid sequence from His541 through Lys551. This region of the protein adopts an alpha helical structure that appears to mediate protein-protein interactions (Example 3). We designed a peptide that mimicked this sequence in order to determine whether such a peptide could substitute for the alpha helix and thereby disrupt protein-protein interactions that are required for HCV replication. The peptide was 25 amino acids in length and contained the following amino acid sequence: HIDAHFLSQTK-GGG-YARAAARQARA (SEQ ID NO:2). The amino terminal region of this peptide (HIDAHFLSQTK, SEQ ID NO:1) is identical to the sequence of residues 541-551 of the NS3 helicase (SEQ ID NO:3). This region is the 'inhibitor' region of the peptide. The three glycines served as a linker between the inhibitor and a peptide sequence that has been shown to be able to improve the uptake of peptides in cells. The c-terminal domain (YARAAARQARA, SEQ ID NO:4) is referred to as the peptide transduction domain of the HCV inhibitor peptide. This sequence can be likely be substituted with other sequences.

Figure 15:
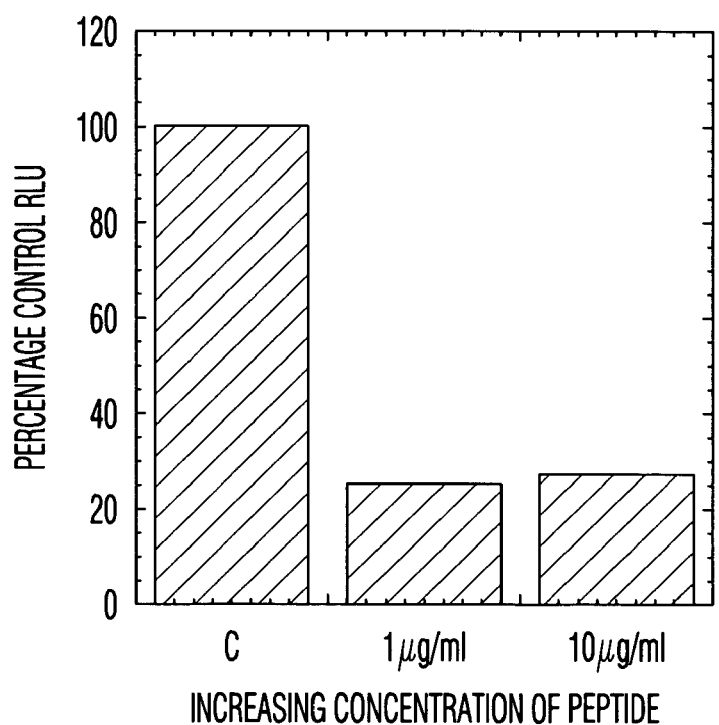
FIG. 15 shows the effect of the HCV inhibitor peptide on replication of the HCV-Luc replicon. HCV inhibitor peptide was added to Huh-7 cells containing the HCV luciferase replicon. Luciferase activity was measured after 48 hours. The bar labeled C is the control containing HCV luciferase replicon with no peptide.

The peptide was introduced into Huh-7 cells containing the HCV luciferase replicon. 48 hours after introduction of the peptide, luciferase activity was measured. The peptide strongly reduced the luciferase activity, indicating that HCV replication was strongly reduced (FIG. 15). These results indicate that it is possible to design small molecule inhibitors of protein-protein interactions that will reduce HCV replication. Such small molecules can be used for the treatment of HCV infection. Small molecules that are designed to mimic the activity of the peptide at sequence His541 through Lys551 should act similarly to the observed activity of the HCV inhibitor peptide.

Example 5

An Adenoviral Vector for Genetic Therapy Using Mutant NS3 Expression in Vitro

A DNA encoding the D290A ATPase-deficient NS3 is cloned for expression in an adenovirus vector for gene therapy of HCV infection. Adenoviral vectors are a well characterized method of gene transfer in both cell culture and in vivo. Two advantages to the use of adenoviral vectors are (i) efficient transfer to multiple cell types and lines, and (ii) efficient transfer to cells that are not actively replicating.

Vector Production

The adenoviral vectors are produced using commercially available methods and materials, including the pAdEasy-1 vector system from Stratagene (La Jolla, Calif.) (64, 65). The D290A NS3 DNA is cloned behind the cauliflower mosaic virus (CMV) promoter in pShuttle-CMV (64) (SEQ ID NO:5) in *E. coli*. The CMV promoter is nucleotides 345-932 of SEQ ID NO:5. The resultant vector is linearized by PmeI and cotransformed into *E. coli* strain BJ5183 with the adenoviral backbone plasmid pAdEasy-1 (SEQ ID NO:7), which lacks the E1 and E3 genes, making it replication defective without those functions being provided in trans. The shuttle vector recombines into pAdEasy-1 by homologous recombination in vivo in *E. coli*. The recombinant vector carries a kanamycin resistance cassette. The pAdEasy-1 vector carries an ampicillin-resistance cassette that is lost in the recombination. *E. coli* colonies resistant to kanamycin are selected, followed by purification of plasmid. Recombinant adenoviral plasmids are screened by restriction digestion with PacI, resulting in fragments of 30 kb and approximately 3-4.5 kb. Non-recombinant plasmids have only the 30 kb fragment.

Once recombinant adenoviral plasmid clones are identified, they are digested with PacI and transfected into HEK293 cells. HEK293 cells are human embryonic kidney cells that have been transformed with sheared Ad5 DNA. They express the transforming genes of Ad5, including E1. The cells produce recombinant viral particles that can be used to transform other cells. Titer is determined by protocols of the product literature.

Cellular Assay

Similar to the assay of Example 1, Huh-7 cells harboring subgenomic HCV replicon are exposed to a concentration series of recombinant mutant-NS3-expressing adenoviral particles. Luciferase activity is measured after 48 hours, as described above. Green fluorescent protein (GFP) is encoded in the adenovirus vector and is used to determine the efficiency of transfection. To verify that the NS3 construct is being expressed, Huh-7 cells that do not contain HCV replicon will also be exposed to viral vectors. These cells are lysed at 48 hours post-transfection, and western blots are performed on the lysate.

Replication of the HCV replicon is monitored by the luciferase assay described in Example 1 to show that adenovirus expressing ATPase-deficient NS3 inhibits HCV replication.

REFERENCE LIST

1. Choo, Q. L., Kuo, G., Weiner, A. J., Overby, L. R., Bradley, D. W., and Houghton, M. (1989) *Science* 244, 359-362
2. Blanchard, E., Brand, D., Trassard, S., Goudeau, A., and Roingeard, P. (2002) *J. Virol.* 76, 4073-4079
3. Tan, S. L., Pause, A., Shi, Y., and Sonenberg, N. (2002) *Nat. Rev. Drug Discov.* 1, 867-881
4. Shimotohno, K. (2000) *Semin. Cancer Biol.* 10, 233-240
5. Terrault, N. A. (2002) *Hepatology* 36, S99-105
6. Blight K J, Kolykhalov A A, Reed K E, Agapov E V, Rice C M (1998) Molecular virology of hepatitis C virus: an update with respect to potential antiviral targets. *Antivir Ther* 3: 71-81
7. Reed, K. E., Grakoui, A., and Rice, C. M. (1995) *J. Virol.* 69, 4127-4136
8. Rosenberg, S. (2001) *J. Mol. Biol.* 313, 451-464
9. Xu, Z., Choi, J., Yen, T. S., Lu, W., Strohecker, A., Govindarajan, S., Chien, D., Selby, M. J., and Ou, J. (2001) *EMBO J.* 20, 3840-3848
10. Caruthers, J. M., and McKay, D. B. (2002) *Current Opinion in Structural Biology* 12, 123-133
11. Kwong, A. D., Kim, J. L., and Lin, C. (2000) *Curr. Top. Microbiol. Immunol.* 242, 171-196
12. Cho, Y. G., Yang, S. H., and Sung, Y. C. (1998) *J. Virol. Methods* 72, 109-115
13. Porter, D. J. (1998) *J. Biol. Chem.* 273, 14247-14253
14. Porter, D. J. (1998) *J. Biol. Chem.* 273, 7390-7396
15. Khu, Y. L., Koh, E., Lim, S. P., Tan, Y. H., Brenner, S., Lim, S. G., Hong, W. J., and Goh, P. Y. (2001) *J. Virol.* 75, 205-214
16. Levin, M. K. and Patel, S. S. (1999) The helicase from hepatitis C virus is active as an oligomer. *J. Biol. Chem.* 274, 31839-31846
17. Bartenschlager, R. (2002) *Virus Res.* 82, 25-32
18. Blight, K. J., McKeating, J. A., and Rice, C. M. (2002) *J. Virol.* 76, 13001-13014
19. Krieger, N., Lohmann, V., and Bartenschlager, R. (2001) *J. Virol.* 75, 4614-4624
20. Tackett, A. J., Wei, L., Cameron, C. E., and Raney, K. D. (2001) Unwinding of nucleic acids by HCV NS3 helicase is sensitive to the structure of the duplex. *Nucleic Acids Res.* 29, 565-572

21. Morris, P. D., Tackett, A. J., Babb, K., Nanduri, B., Chick, C., Scott, J., and Raney, K. D. (2001) *J. Biol. Chem.* 276, 19691-19698
22. Piccininni, S., Varaklioti, A., Nardelli, M., Dave, B., Raney, K. D., and McCarthy, J. E. (2002) Modulation of the hepatitis C virus RNA-dependent RNA polymerase activity by the non-structural (NS) 3 helicase and the NS4B membrane protein. *J. Biol. Chem.* 277, 45670-45679
23. Raney, K. D. and Benkovic, S. J. (1995) *J. Biol. Chem.* 270, 22236-22242
24. He, Y., Yan, W., Coito, C., Li, Y., Gale, M., Jr., and Katze, M. G. (2003) *J. Gen. Virol.* 84, 535-543
25. He, Y., Yan, W., Coito, C., Li, Y., Gale, M., Jr., and Katze, M. G. (2003) *J. Gen. Virol.* 84, 535-543
26. Lohmann, V., Korner, F., Koch, J., Herian, U., Theilmann, L., and Bartenschlager, R. (1999) Replication of subgenomic hepatitis C virus RNAs in a hepatoma cell line. *Science* 285, 110-113
27. Goregaoker, S. P. and Culver, J. N. (2003) *J. Virol.* 77, 3549-3556
28. Ng, P., Parks, R. J., and Graham, F. L. (2002) Preparation of helper-dependent adenoviral vectors, pp. 371-388 in *Gene Therapy Protocols*, J. R. Morgan ed., Humana Press, Totowa, N.J.
29. Sandig, V., et al. (2000) *Proc. Nat'l Acad. Sci. USA* 97, 1002-1007
30. Cristiano, R. J. et al. (1993) *Proc. Nat'l. Acad. Sci. USA* 90, 11548-11552
31. Wu, C. H., Walton, C. M., and Wu, G. Y. (2002) Targeted gene transfer to liver using protein-DNA complexes, pp. 15-23 in *Gene Therapy Protocols*, J. R. Morgan ed., Humana Press, Totowa, N.J.
32. Templeton, N. S., and Lasic, D. D., eds., (2000) *Gene Therapy: Therapeutic Mechanisms and Strategies*, Marcel Dekker, Inc., New York.
33. Zhang, G., et al. (2002) *Meth. Enzymol.* 346,125
34. Bianchi et al. (1996) Anal. Biochem. 237, 239-244
35. Lin C, Thomson J A, Rice C M (1995) A central region in the hepatitis C virus NS4A protein allows formation of an active NS3-NS4A serine proteinase complex in vivo and in vitro. *J Virol* 69: 4373-4380
36. Qin W, Luo H, Nomura T, Hayashi N, Yamashita T, Murakami S (2002) Oligomeric interaction of hepatitis C virus NS5B is critical for catalytic activity of RNA-dependent RNA polymerase. *J Biol Chem* 277: 2132-2137
37. Mottola G, Cardinali G, Ceccacci A, Trozzi C, Bartholomew L, Torrisi M R, Pedrazzini E, Bonatti S, Migliaccio G (2002) Hepatitis C virus nonstructural proteins are localized in a modified endoplasmic reticulum of cells expressing viral subgenomic replicons. *Virology* 293: 31-43
38. Shi S T, Lee K J, Aizaki H, Hwang S B, Lai M M (2003) Hepatitis C virus RNA replication occurs on a detergent-resistant membrane that cofractionates with caveolin-2. *J Virol* 77: 4160-4168
39. Kim D W, Gwack Y, Han J H, Choe J (1995) C-terminal domain of the hepatitis C virus NS3 protein contains an RNA helicase activity. *Biochem Biophys Res Commun* 215: 160-166
40. Cho H S, Ha N C, Kang L W, Chung K M, Back S H, Jang S K, Oh B H (1998) Crystal structure of RNA helicase from genotype 1b hepatitis C virus. A feasible mechanism of unwinding duplex RNA. *J Biol Chem* 273: 15045-15052
41. Kim J L, Morgenstern K A, Griffith J P, Dwyer M D, Thomson J A, Murcko M A, Lin C, Caron P R (1998) Hepatitis C virus NS3 RNA helicase domain with a bound oligonucleotide: the crystal structure provides insights into the mode of unwinding. *Structure* 6: 89-100
42. Gallinari P, Brennan D, Nardi C, Brunetti M, Tomei L, Steinkuhler C, De Francesco R (1998) Multiple enzymatic activities associated with recombinant NS3 protein of hepatitis C virus. *J Virol* 72: 6758-6769
43. Serebrov V, Pyle A M (2004) Periodic cycles of RNA unwinding and pausing by hepatitis C virus NS3 helicase. *Nature* 430: 476-480
44. Locatelli G A, Spadari S, Maga G (2002) Hepatitis C virus NS3 ATPase/helicase: an ATP switch regulates the cooperativity among the different substrate binding sites. *Biochemistry* 41: 10332-10342
45. Frick D N, Rypma R S, Lam A M, Gu B (2004) The nonstructural protein 3 protease/helicase requires an intact protease domain to unwind duplex RNA efficiently. *J Biol Chem* 279: 1269-1280
46. Yao N, Reichert P, Taremi S S, Prosise W W, Weber P C (1999) Molecular views of viral polyprotein processing revealed by the crystal structure of the hepatitis C virus bifunctional protease-helicase. *Structure Fold Des* 7: 1353-1363
48. Levin M K, Patel S S (2002) Helicase from hepatitis C virus, energetics of DNA binding. *J Biol Chem* 277: 29377-29385
49. Levin M K, Wang Y H, Patel S S (2004) The functional interaction of the hepatitis C virus helicase molecules is responsible for unwinding processivity. *J. Biol Chem* 279: 26005-26012
49b. Navaza J (2001) Implementation of molecular replacement in AMoRe. *Acta Crystallogr D Biol Crystallogr* 57: 1367-1372
50. Brunger A T, Adams P D, Clore G M, DeLano W L, Gros P, Grosse-Kunstleve R W, Jiang J S, Kuszewski J, Nilges M, Pannu N S, Read R J, Rice L M, Simonson T, Warren G L (1998) Crystallography & NMR system: A new software suite for macromolecular structure determination. *Acta Crystallogr D Biol Crystallogr* 54 (Pt 5): 905-921
51. McRee D E (1999) XtalView/Xfit—A versatile program for manipulating atomic coordinates and electron density. *J Struct Biol* 125: 156-165
52. Ali J A, Lohman T M (1997) Kinetic Measurement of the Step Size of DNA Unwinding by *Escherichia coli* UvrD Helicase. *Science* 275: 377-380
53. Lucius A L, Maluf N K, Fischer C J, Lohman T M (2003) General methods for analysis of sequential "n-step" kinetic mechanisms: application to single turnover kinetics of helicase-catalyzed DNA unwinding. *Biophys J* 85: 2224-39
54. Hooft R W, Vriend G, Sander C, Abola E E (1996) Errors in protein structures. *Nature* 381: 272-
55. Parkinson G (1996) New Parameters for the Refinement of Nucleic Acid-Containing Structures. *Acta Crystallographica* D52: 57-64
55b. Vriend G (1990) WHAT IF: a molecular modeling and drug design program. *J Mol Graph* 8: 52-6, 29
56. Blight K J, Kolykhalov A A, Rice C M (2000) Efficient initiation of HCV RNA replication in cell culture. *Science* 290: 1972-1974
57. Porter D J, Preugschat F (2000) Strand-separating activity of hepatitis C virus helicase in the absence of ATP. *Biochemistry* 39: 5166-5173
58. Galletto R, Jezewska M J, Bujalowski W (2004) Unzipping mechanism of the double-stranded DNA unwinding by a hexameric helicase: quantitative analysis of the rate of the dsDNA unwinding, processivity and kinetic step-size of the *Escherichia coli* DnaB helicase using rapid quench-flow method. *J Mol Biol* 343: 83-99

59. Pang P S, Jankowsky E, Planet P J, Pyle A M (2002) The hepatitis C viral NS3 protein is a processive DNA helicase with cofactor enhanced RNA unwinding. *EMBO J* 21: 1168-1176
60. Singleton M R, Wigley D B (2002) Modularity and specialization in superfamily 1 and 2 helicases. *J Bacteriol* 184: 1819-1826
61. Dillingham M S, Spies M, Kowalczykowski S C (2003) RecBCD enzyme is a bipolar DNA helicase. *Nature* 423: 893-897
62. Singleton M R, Dillingham M S, Gaudier M, Kowalczykowski S C, Wigley D B (2004) Crystal structure of RecBCD enzyme reveals a machine for processing DNA breaks. *Nature* 432: 187-193
63. Ha T, Rasnik I, Cheng W, Babcock H P, Gauss G H, Lohman T M, Chu S (2002) Initiation and re-initiation of DNA unwinding by the *Escherichia coli* Rep helicase. *Nature* 419: 638-41
64. Hosfield T and Eldrige L, Generate adenovirus vectors in *E. coli* by homologous recombination with the AdEasy adenoviral vector system. Strategies 13: 100-102
65. He T-C, Zho S, Da Costa L T, Yu J, Kinzler K W, and Vogelstein B (1998) A simplified system for generating recombinant adenovirus. Proc. Natl. Acad. Sci. USA 95: 2509-14
66. Thoren P E, Persson D, Lincoln P, and Norden B (2005) Membrane destabilizing properties of cell-penetrating peptides. *Biophys. Chem.* 114: 169-179
67. Thoren P E, Persson D, Isakson P, Goksor M, Onfelt A, and Norden B (2003) Uptake of analogs of pentratin, Tat (48-60) and oligoarginine in live cells. Biochem. Biophys. Res. Commun. 307: 100-107
68. Goodford P J (1985) A Computational Procedure for Determining Energetically Favorable Binding Sites on Biologically Important Macromolecules. *J. Med. Chem.* 28: 849-857
69. Miranker A and Karplus M (1991) Functionality Maps of Binding Sites: A Multiple Copy Simultaneous Search Method. *Proteins: Structure. Function and Genetics* 11: 29-34
70. Goodsell D S and Olsen A J (1990) Automated Docking of Substrates to *Proteins by Simulated Annealing. Proteins: Structure. Function and Genetics* 8: 195-202
71. Kuntz I D et al. (1982) A Geometric Approach to Macromolecule-Ligand Interactions. *J. Mol. Biol.* 161: 269-288
72. Rusinko A (1993) *Chem. Des. Auto. News* 8: 44-47
73. Bartlett P A et al (1989) CAVEAT: A Program to Facilitate the Structure-Derived Design of Biologically Active Molecules, in *Molecular Recognition in Chemical and Biological Problems*, Special Pub., Royal Chem. Soc. 78: 182-196
74. Martin Y C (1992) 3D Database Searching in Drug Design. *J. Med. Chem.* 35: 2145-2154
75. Bohm H-J (1992) The Computer Program LUDI: A New Method for the De Novo Design of Enzyme Inhibitors. *J. Comp. Aid. Molec. Design* 6: 61-78
76. Nishibata Y and Itai A (1991) *Tetrahedron* 47: 8985
77. Cohen N C et al. (1990) Molecular Modeling Software and Methods for Medicinal Chemistry. *J. Med. Chem.* 33: 883-894
78. Navia M A and Murcko M A (1992) The Use of Structural Information in Drug Design. *Current Opinions in Structural Biology* 2: 202-210
79. Farmer P S (1980) *Drug Design*, Ariens, E. J., ed., Vol. 10, pp 119-143 (Academic Press, New York, 1980).
80. Verlinde C (1994) *Structure* 2: 577-587
81. Kuntz I D (1992) *Science* 257: 1078-1082

All patents, patent-related documents, and references cited herein are hereby incorporated by reference.

We claim:

1. A method of inhibiting hepatitis C virus (HCV) replication in cells infected with HCV comprising:

contacting the cells with an agent that inhibits NS3 enzyme activity by inhibiting NS3 oligomerization; wherein the agent reduces replication of viral nucleic acid in the cells or spread of virus to other cells;

wherein the agent is a vector expressing a dominant-negative mutant NS3 gene that expresses an ATPase-deficient NS3 protein that is 90% identical to SEQ ID NO:3 and the step of contacting the agent comprises transforming the cells with the vector;

wherein the ATPase-deficient NS3 protein comprises a D290A mutation; and wherein the cells are in vitro.

2. A method of inhibiting hepatitis C virus (HCV) replication in cells infected with HCV comprising:

contacting the cells with an agent that inhibits NS3 enzyme activity by inhibiting NS3 oligomerization; wherein the agent reduces replication of viral nucleic acid in the cells or spread of virus to other cells;

wherein the agent is a peptide of 4 to 100 residues comprising at least 4 contiguous residues of HIDAHFLSQTK (SEQ ID NO:1) or at least 4 contiguous residues of reverse D sequence of SEQ ID NO:1.

3. The method of claim 2 wherein the agent comprises a peptide comprising the sequence HIDAHFLSQTK (SEQ ID NO:1).

4. The method of claim 3 wherein the agent is the peptide having the sequence HIDAHFLSQTKGGGYARAAARQARA (SEQ ID NO:2).

5. The method of claim 2 wherein the cells are in vitro.

6. The method of claim 2 wherein the agent is a peptide comprising the reverse D sequence of SEQ ID NO:1.

* * * * *